ns(12) United States Patent
Atsumi et al.

(10) Patent No.: US 10,174,348 B2
(45) Date of Patent: Jan. 8, 2019

(54) BACTERIA ENGINEERED FOR ESTER PRODUCTION

(71) Applicant: The Regents of the University of California, Oakland, CA (US)

(72) Inventors: Shota Atsumi, Davis, CA (US); Gabriel Rodriguez, Davis, CA (US); Yohei Tashiro, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 264 days.

(21) Appl. No.: 14/915,099

(22) PCT Filed: Aug. 29, 2014

(86) PCT No.: PCT/US2014/053587
§ 371 (c)(1),
(2) Date: Feb. 26, 2016

(87) PCT Pub. No.: WO2015/031859
PCT Pub. Date: Mar. 5, 2015

(65) Prior Publication Data
US 2016/0208294 A1   Jul. 21, 2016

Related U.S. Application Data

(60) Provisional application No. 61/871,799, filed on Aug. 29, 2013.

(51) Int. Cl.
| | |
|---|---|
| *C12P 7/62* | (2006.01) |
| *C12N 9/10* | (2006.01) |
| *C12N 15/52* | (2006.01) |
| *C12N 9/00* | (2006.01) |
| *C12N 9/88* | (2006.01) |
| *C12N 9/04* | (2006.01) |
| *C12N 9/02* | (2006.01) |

(52) U.S. Cl.
CPC .............. *C12P 7/62* (2013.01); *C12N 9/0006* (2013.01); *C12N 9/0008* (2013.01); *C12N 9/1022* (2013.01); *C12N 9/1029* (2013.01); *C12N 9/88* (2013.01); *C12N 15/52* (2013.01); *C12Y 101/01001* (2013.01); *C12Y 101/01086* (2013.01); *C12Y 102/0101* (2013.01); *C12Y 102/01025* (2013.01); *C12Y 202/01006* (2013.01); *C12Y 203/01084* (2013.01); *C12Y 401/01074* (2013.01); *C12Y 402/01009* (2013.01)

(58) Field of Classification Search
None
See application file for complete search history.

(56) References Cited

U.S. PATENT DOCUMENTS

| | | |
|---|---|---|
| 9,701,948 B2 | 7/2017 | Atsumi et al. |
| 2008/0274526 A1 | 11/2008 | Bramucci et al. |
| 2010/0209986 A1 | 8/2010 | Liao et al. |

FOREIGN PATENT DOCUMENTS

| | | |
|---|---|---|
| EP | 1006190 A1 | 6/2000 |
| WO | 2001/18195 A2 | 3/2001 |
| WO | 2010/071851 A1 | 6/2010 |
| WO | 2012/061653 A2 | 5/2012 |
| WO | 2012/135789 A2 | 10/2012 |
| WO | 2012/173658 A1 | 12/2012 |
| WO | 2015/031859 A1 | 3/2015 |

OTHER PUBLICATIONS

Atsumi et al., "Engineering the Isobutanol Biosynthetic Pathway in *Escherichia coli* by Comparison of Three Aldehyde Reductase/Alcohol Dehydrogenase Genes", Applied Microbiology and Biotechnology, vol. 85, 2010, pp. 651-657.
Atsumi et al., "Non-Fermentative Pathways for Synthesis of Branched-Chain Higher Alcohols as Biofuels", Nature, vol. 451, Jan. 3, 2008, pp. 86-89.
Darracq et al., "Removal of Hydrophobic Volatile Organic Compounds in an Integrated Process Coupling Absorption and Biodegradation—Selection of an Organic Liquid Phase", Water, Air, & Soil Pollution, vol. 223, 2012, pp. 4969-4997.
International Preliminary Report on Patentability received for PCT Patent Application No. PCT/US2014/053587, dated Mar. 10, 2016, 11 pages.
International Search Report and Written Opinion received for PCT Application No. PCT/US2014/053587, dated Dec. 19, 2014, 13 pages.
Rabinovitch-Deere et al., "Synthetic Biology and Metabolic Engineering Approaches to Produce Biofuels", Chemical Reviews, vol. 113, 2013, pp. 4611-4632.
Rodriguez et al., "Isobutyraldehyde Production from *Escherichia coli* by Removing Aldehyde Reductase Activity", Microbial Cell Factories, vol. 11, No. 90, 2012, pp. 1-11.
Rodriguez et al., "Toward Aldehyde and Alkane Production by Removing Aldehyde Reductase Activity in *Escherichia coli*", Metabolic Engineering, vol. 25, Sep. 2014, pp. 227-237.
Tashiro et al., "Two-Dimensional Isobutyl Acetate Production Pathways to Improve Carbon Yield", Nature communications, vol. 6, No. 7488, 2015, pp. 1-9.

*Primary Examiner* — Suzanne M Noakes
(74) *Attorney, Agent, or Firm* — Morrison & Foerster LLP

(57) ABSTRACT

The present disclosure provides recombinant bacteria with elevated 2-keto acid decarboxylase and alcohol transferase activities. Some recombinant bacteria further have elevated aldehyde dehydrogenase activity. Some recombinant bacteria further have reduced alcohol dehydrogenase and/or aldehyde reductase activity. Methods for the production of the recombinant bacteria, as well as for use thereof for production of various esters are also provided.

24 Claims, 23 Drawing Sheets
Specification includes a Sequence Listing.

SEQUENCE LISTING

```
<160> NUMBER OF SEQ ID NOS: 37

<210> SEQ ID NO 1
<211> LENGTH: 1578
<212> TYPE: DNA
<213> ORGANISM: S. cerevisiae

<400> SEQUENCE: 1
atgaacgaaa tcgacgaaaa gaatcaagcc ccggtccaac aagaatgcct gaaagaaatg     60
atccagaatg gtcacgcccg ccgtatgggc tcagtggaag acctgtatgt tgcactgaac    120
cgtcagaatc tgtaccgcaa tttttgcacc tatggtgaac tgtcggacta ctgtacgcgt    180
gatcaactga ccctggctct gcgcgaaatc tgcctgaaaa acccgacgct gctgcatatt    240
gtgctgccga cccgttggcc gaaccacgaa aactactacc gtagctctga atactacagt    300
cgcccgcatc cggttcacga ttatattagt gtcctgcaag aactgaaact gtccggcgtg    360
gttctgaatg aacagccgga atacagcgcg gttatgaagc aaatcctgga agaatttaaa    420
aacagcaagg gttcttacac ggccaaaatc tttaagctga ccacgaccct gacgattccg    480
tacttcggtc cgaccggtcc gagctggcgc ctgatctgcc tgccggaaga acataccgaa    540
aagtggaaga agttcatctt cgtgtcaaac cactgtatgt cggatggccg tagttccatc    600
catttctttc acgacctgcg cgatgaactg aacaatatca agacccgcc gaaaaagctg    660 gactacatct tcaagtacga agaagattac cagctgctgc gtaagctgcc ggaaccgatt    720
gaaaaagtga tcgatttcg tccgccgtac ctgtttatcc cgaaaagtct gctgtccggc    780
```

```
tttatttaca atcatctgcg tttctcatcg aagggtgtgt gcatgcgcat ggatgacgtt      840
gaaaaaacgg atgacgtcgt gaccgaaatt atcaacatta gcccgaccga atttcaggcg      900
atcaaggcca acatcaagtc taacatccaa ggcaaatgca cgatcacccc gtttctgcat      960
gtctgttggt tcgtgagcct gcacaaatgg ggcaagtttt tcaaaccgct gaactttgaa     1020
tggctgacgg acattttcat cccggcggat tgtcgttctc agctgccgga tgacgatgaa     1080
atgcgtcaaa tgtatcgcta cggcgccaat gtgggtttta tcgatttcac cccgtggatt     1140
agtgaatttg acatgaacga taacaaggaa aacttctggc cgctgatcga acattatcac     1200
gaagttattt ccgaagcgct gcgtaacaaa aagcatctgc acggcctggg tttcaacatc     1260
cagggtttcg ttcaaaagta cgtcaacatc gacaaagtca tgtgtgatcg cgccattggc     1320
aaacgtcgtg gcggcaccct gctgtccaac gttggtctgt ttaatcagct ggaagaaccg     1380
gacgcaaaat attcaatttg cgatctggct tttggccagt ccaaggttc gtggcatcag     1440 gcattcagcc tgggcgtctg ttctacgaac gtgaagggta tgaatattgt tgtcgcttct     1500
accaaaaatg tggttggtag ccaagaatcg ctggaagaac tgtgtagtat ctataaggca     1560
ctgctgctgg gtccgtaa                                                   1578

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct

<400> SEQUENCE: 2
tctagaggca tcaaataaaa cgaaa                                             25

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gtgacctttc tcctgcatgc                                                   20

<210> SEQ ID NO 4
<211> LENGTH: 47
<212> TYPE: DNA
<213> ORGANISM: Artificial Sequence
<220> FEATURE:
<223> OTHER INFORMATION: Synthetic Construct

<400> SEQUENCE: 4
gcatgcagga gaaaggtcac atgagtaagc gtaaagtcgc cattatc                     47

<210> SEQ ID NO 5
<211> LENGTH: 28
<212> TYPE: DNA
<213> ORGANISM: Artificial Sequence
<220> FEATURE:
<223> OTHER INFORMATION: Synthetic Construct

<400> SEQUENCE: 5
tctagaggca tcaaataaaa cgaaaggc                                          28

<210> SEQ ID NO 6
<211> LENGTH: 29
```

```
<212> TYPE: DNA
<213> ORGANISM: Artificial Sequence
<220> FEATURE:
<223> OTHER INFORMATION: Synthetic Construct

<400> SEQUENCE: 6
ggtacctttc tcctctttaa tgaattcgg                                      29

<210> SEQ ID NO 7
<211> LENGTH: 41
<212> TYPE: DNA
<213> ORGANISM: Artificial Sequence
<220> FEATURE:
<223> OTHER INFORMATION: Synthetic Construct

<400> SEQUENCE: 7
ttttatttga tgcctctaga tcatgccgct tctcctgcct t                        41

<210> SEQ ID NO 8
<211> LENGTH: 48
<212> TYPE: DNA
<213> ORGANISM: Artificial Sequence
<220> FEATURE:
<223> OTHER INFORMATION: Synthetic Construct

<400> SEQUENCE: 8
gcatgcagga gaaggtcac atgaacgaaa tcgacgaaaa gaatcaag                  48

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
ttttatttga tgcctctaga ttacggaccc agcagcagtg                          40

<210> SEQ ID NO 10
<211> LENGTH: 41
<212> TYPE: DNA
<213> ORGANISM: Artificial Sequence
<220> FEATURE:
<223> OTHER INFORMATION: Synthetic Construct

<400> SEQUENCE: 10
ttaaagagga gaaaggtacc atgaacgagt acgccccct g                         41

<210> SEQ ID NO 11
<211> LENGTH: 40
<212> TYPE: DNA
<213> ORGANISM: Artificial Sequence
<220> FEATURE:
<223> OTHER INFORMATION: Synthetic Construct

<400> SEQUENCE: 11
ttttatttga tgcctctaga tcagatatgc aaggcgtggc                          40

<210> SEQ ID NO 12
<211> LENGTH: 35
<212> TYPE: DNA
<213> ORGANISM: Artificial Sequence
<220> FEATURE:
<223> OTHER INFORMATION: Synthetic Construct

<400> SEQUENCE: 12
```
gaacgccgta cgcgagcggt atcagctcac tcaaa                             35

<210> SEQ ID NO 13
<211> LENGTH: 33
<212> TYPE: DNA
<213> ORGANISM: Artificial Sequence
<220> FEATURE:
<223> OTHER INFORMATION: Synthetic Construct

<400> SEQUENCE: 13
gcctcgtcct aggtctaggg cggcggattt gtc                               33

<210> SEQ ID NO 14
<211> LENGTH: 45
<212> TYPE: DNA
<213> ORGANISM: Artificial Sequence
<220> FEATURE:
<223> OTHER INFORMATION: Synthetic Construct

<400> SEQUENCE: 14
cgccgcccta gacctaggac gaggcccttt cgtcttcacc tcgag                  45

<210> SEQ ID NO 15
<211> LENGTH: 45
<212> TYPE: DNA
<213> ORGANISM: Artificial Sequence
<220> FEATURE:
<223> OTHER INFORMATION: Synthetic Construct

<400> SEQUENCE: 15
gagctgatac cgctcgcgta cggcgttcac cgacaaacaa cagat                  45

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16
taaacgcgtg ctagaggcat caaat                                        25

<210> SEQ ID NO 17
<211> LENGTH: 35
<212> TYPE: DNA
<213> ORGANISM: Artificial Sequence
<220> FEATURE:
<223> OTHER INFORMATION: Synthetic Construct

<400> SEQUENCE: 17
catggtacct ttctcctctt taatgaattc ggtca                             35

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
cattgtacct ttctcctctt taatgaattc                                   30

<210> SEQ ID NO 19
<211> LENGTH: 35
<212> TYPE: DNA
<213> ORGANISM: Artificial Sequence
<220> FEATURE:
<223> OTHER INFORMATION: Synthetic Construct

<400> SEQUENCE: 19
cattaaagag gagaaaggta ccatggcttc ctccg                                35

<210> SEQ ID NO 20
<211> LENGTH: 39
<212> TYPE: DNA
<213> ORGANISM: Artificial Sequence
<220> FEATURE:
<223> OTHER INFORMATION: Synthetic Construct

<400> SEQUENCE: 20
ttatttgatg cctctagagt cattaagcac cggtggagt                            39

<210> SEQ ID NO 21
<211> LENGTH: 52
<212> TYPE: DNA
<213> ORGANISM: Artificial Sequence
<220> FEATURE:
<223> OTHER INFORMATION: Synthetic Construct

<400> SEQUENCE: 21
cattaaagag gagaaaggta caatggaaaa acacttacct ttaataataa at             52

<210> SEQ ID NO 22
<211> LENGTH: 38
<212> TYPE: DNA
<213> ORGANISM: Artificial Sequence
<220> FEATURE:
<223> OTHER INFORMATION: Synthetic Construct

<400> SEQUENCE: 22
atcgtttaaa cgaacatttc cttatttgtt ggtattac                             38

<210> SEQ ID NO 23
<211> LENGTH: 31
<212> TYPE: DNA
<213> ORGANISM: Artificial Sequence
<220> FEATURE:
<223> OTHER INFORMATION: Synthetic Construct

<400> SEQUENCE: 23
taaggaaatg ttcgtttaaa cgatgctgaa g                                    31

<210> SEQ ID NO 24
<211> LENGTH: 45
<212> TYPE: DNA
<213> ORGANISM: Artificial Sequence
<220> FEATURE:
<223> OTHER INFORMATION: Synthetic Construct

<400> SEQUENCE: 24
atttgatgcc tctagcacgc gtttagttgc ctccttcatt cttag                     45

<210> SEQ ID NO 25
<211> LENGTH: 48
<212> TYPE: DNA
<213> ORGANISM: Artificial Sequence
<220> FEATURE:
<223> OTHER INFORMATION: Synthetic Construct

<400> SEQUENCE: 25
cattaaagag gagaaaggta caatgtttcg ctcgggttac tatccaac                  48

<210> SEQ ID NO 26
<211> LENGTH: 54
<212> TYPE: DNA
<213> ORGANISM: Artificial Sequence
<220> FEATURE:
<223> OTHER INFORMATION: Synthetic Construct

<400> SEQUENCE: 26
atttgatgcc tctagcacgc gtttataaaa ctaactcatc aaagctgccc aaga     54

<210> SEQ ID NO 27
<211> LENGTH: 47
<212> TYPE: DNA
<213> ORGANISM: Artificial Sequence
<220> FEATURE:
<223> OTHER INFORMATION: Synthetic Construct

<400> SEQUENCE: 27
cattaaagag gagaaaggta caatgtcaga agtttccaaa tggccag              47

<210> SEQ ID NO 28
<211> LENGTH: 60
<212> TYPE: DNA
<213> ORGANISM: Artificial Sequence
<220> FEATURE:
<223> OTHER INFORMATION: Synthetic Construct

<400> SEQUENCE: 28
tttgatgcct ctagcacgcg tttatacgac taattcatca aacttagtga aaaattctgc    60

<210> SEQ ID NO 29
<211> LENGTH: 50
<212> TYPE: DNA
<213> ORGANISM: Artificial Sequence
<220> FEATURE:
<223> OTHER INFORMATION: Synthetic Construct

<400> SEQUENCE: 29
cattaaagag gagaaaggta caatgaacga atcgacgaa aagaatcaag              50

<210> SEQ ID NO 30
<211> LENGTH: 42
<212> TYPE: DNA
<213> ORGANISM: Artificial Sequence
<220> FEATURE:
<223> OTHER INFORMATION: Synthetic Construct

<400> SEQUENCE: 30
atttgatgcc tctagcacgc gtttacggac ccagcagcag tg                    42

<210> SEQ ID NO 31
<211> LENGTH: 52
<212> TYPE: DNA
<213> ORGANISM: Artificial Sequence
<220> FEATURE:
<223> OTHER INFORMATION: Synthetic Construct

<400> SEQUENCE: 31
tctcaccaat aaaaaacgcc cggcgaattg tgagcggata acaattgaca tt         52

<210> SEQ ID NO 32
<211> LENGTH: 55
<212> TYPE: DNA
<213> ORGANISM: Artificial Sequence
<220> FEATURE:
<223> OTHER INFORMATION: Synthetic Construct

```
<400> SEQUENCE: 32
ggatttgttc agaacgctcg gttgcctagc acgcgtttat acgactaatt catca        55

<210> SEQ ID NO 33
<211> LENGTH: 24
<212> TYPE: DNA
<213> ORGANISM: Artificial Sequence
<220> FEATURE:
<223> OTHER INFORMATION: Synthetic Construct

<400> SEQUENCE: 33
gcaaccgagc gttctgaaca aatc                                          24

<210> SEQ ID NO 34
<211> LENGTH: 21
<212> TYPE: DNA
<213> ORGANISM: Artificial Sequence
<220> FEATURE:
<223> OTHER INFORMATION: Synthetic Construct

<400> SEQUENCE: 34
cgccgggcgt tttttattgg t                                             21

<210> SEQ ID NO 35
<211> LENGTH: 58
<212> TYPE: DNA
<213> ORGANISM: Artificial Sequence
<220> FEATURE:
<223> OTHER INFORMATION: Synthetic Construct

<400> SEQUENCE: 35
gaattcatta aagaggagaa aggtacaatg gagaaaaaaa tcactggata taccaccg     58

<210> SEQ ID NO 36
<211> LENGTH: 38
<212> TYPE: DNA
<213> ORGANISM: Artificial Sequence
<220> FEATURE:
<223> OTHER INFORMATION: Synthetic Construct

<400> SEQUENCE: 36
atttgatgcc tctagcacgc gtttacgccc cgccctgc                           38

<210> SEQ ID NO 37
<211> LENGTH: 45
<212> TYPE: DNA
<213> ORGANISM: Artificial Sequence
<220> FEATURE:
<223> OTHER INFORMATION: Synthetic Construct

<400> SEQUENCE: 37
ggatttgttc agaacgctcg gttgcctagc acgcgtttac gcccc                   45
```

BACTERIA ENGINEERED FOR ESTER PRODUCTION

CROSS-REFERENCE TO RELATED APPLICATIONS

This application is a U.S. National Stage of PCT/US2014/053587, filed Aug. 29, 2014, which claims the benefit of U.S. Provisional Application No. 61/871,799, filed Aug. 29, 2013, which are incorporated herein by reference in their entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 514112007100SEQLISTING.TXT, date recorded: Sep. 9, 2018, size: 9 KB).

FIELD OF THE INVENTION

The present disclosure provides recombinant bacteria with elevated 2-keto acid decarboxylase and alcohol transferase activities. Some recombinant bacteria further have elevated aldehyde dehydrogenase activity. Some recombinant bacteria further have reduced alcohol dehydrogenase and/or isobutyraldehyde reductase activity. Methods for the production of the recombinant bacteria, as well as for use thereof for production of various esters are also provided.

BACKGROUND OF THE INVENTION

Long term economic and environmental concerns with the current petroleum-based economy have driven the development of approaches that convert renewable sources to organic chemicals to replace those derived from petroleum feed stocks. Production of biofuels, such as ethanol or butanol, through microorganisms has been a research focus in recent years, and significant progress has been made in this area. At the same time, there remains a great need for development of biorefining processes that utilize microorganisms to convert renewable sources into industrially useful chemicals.

Esters, in particular, are in great demand for a variety of industrial and cosmetic applications. Isobutyl isobutyrate is a popular retarder solvent for a variety of lacquers and thinners, and it can be found in numerous painted coatings. It is also used as an insect repellant. The estimated United States annual production of isobutyl isobutyrate is approximately four thousand metric tons. Isobutyl acetate, ethyl isobutyrate, isoamyl acetate, and phenethyl acetate are also used as lacquer solvents. In addition to their industrial uses, acetate and isobutyrate esters are naturally found in plants, and they are used in various cosmetics, fragrances, and food products for their fruity and/or floral aromas. For example, isobutyl isobutyrate smells like pineapple, and isoamyl acetate has a strong, banana-like odor.

The current method of producing these esters involves individually producing the constituent alcohols and carboxylic acids, then esterifying them through chemical synthesis or enzymatic reactions. This two-step process requires individual production and purification steps to generate each constituent and further processing and purification steps to yield the final ester. Much of the production of the constituent alcohols and carboxylic acids depends heavily upon petroleum, which is increasingly expensive and associated with global health and environmental concerns.

In view of these facts and the growing global demand for acetate and isobutyrate esters, a significant need exists for esters produced from renewable sources. Specifically, recombinant bacteria are needed for cost-efficient biosynthesis of acetate and isobutyrate esters.

BRIEF SUMMARY OF THE INVENTION

The present disclosure provides recombinant bacteria with elevated 2-keto acid decarboxylase and alcohol transferase activities. Some recombinant bacteria further have elevated aldehyde dehydrogenase activity. Some recombinant bacteria further have reduced alcohol dehydrogenase and/or aldehyde reductase activity. Methods for the production of the recombinant bacteria, as well as for use thereof for production of various esters are also provided.

In particular, the present disclosure provides bacteria comprising a recombinant polynucleotide encoding an alcohol transferase (ATF) and either a 2-keto acid decarboxylase (KDC) or a 2-ketoisovalerate dehydrogenase enzyme complex (KIVDH), wherein expression of the ATF and either the KDC or the KIVDH results in an increase in production of an ester as compared to corresponding bacteria (e.g., same genus and species) lacking the recombinant polynucleotide. In some embodiments, the recombinant polynucleotide further encodes an aldehyde dehydrogenase (ALDH), wherein expression of the ALDH, the ATF, and either the KDC or the KIVDH results in an increase in production of an ester as compared to corresponding bacteria (e.g., same genus and species) lacking the recombinant polynucleotides. In some embodiments, the recombinant polynucleotide comprises one, two or three recombinant polynucleotides. In some embodiments, the ATF is ATF1. In other embodiments, the ATF is a homolog of ATF1 having at least 85%, at least 90% or at least 95% sequence identity to ATF1 encoded by ATF1 of S. cerevisiae. In some embodiments, the ester comprises an acetate ester. In some embodiments, the acetate ester comprises one or more of ethyl acetate, isobutyl acetate, isoamyl acetate, propyl acetate, amyl acetate, and 2-pheneethyl acetate. In specific embodiments, the acetate ester comprises one or more of ethyl acetate, isobutyl acetate, and isoamyl acetate. In specific embodiments, the acetate ester comprises one or more of propyl acetate, amyl acetate, and 2-pheneethyl acetate. In some embodiments, the ATF is EHT1. In other embodiments, the ATF is a homolog of EHT1 having at least 85%, at least 90% or at least 95% sequence identity to ATF encoded by EHT1 of S. cerevisiae. In some embodiments, the ester comprises an isobutyrate ester. In some embodiments, the isobutyrate ester comprises one or more of ethyl isobutyrate, isobutyl isobutyrate, 3-methylbutyl isobutyrate, and phenethyl isobutyrate. In specific embodiments, the isobutyrate ester comprises one or more of ethyl isobutyrate and isobutyl isobutyrate. In specific embodiments, the isobutyrate ester comprises one or both of 3-methylbutyl isobutyrate, and phenethyl isobutyrate. In some embodiments, the ester is a butyrate ester. In a specific embodiments, the butyrate ester comprises butyl butyrate. In some embodiments, the KDC is Kivd. In other embodiments, the KDC is a homolog of Kivd having at least 85%, at least 90% or at least 95% sequence identity to Kivd encoded by kivd of L. lactis. In some embodiments, the KIVDH is Kivdh. In other embodiments, the KIVDH is a homolog of Kivdh having at least 85%, at least 90% or at least 95% sequence identity to Kivdh encoded by kivdh of P. putida. In some embodiments, the ALDH is MhpF. In other embodiments, the ALDH is a homolog of MhpF having at least 85%, at least 90% or at least 95% sequence identity to MhpF encoded by mhpF of *E. coli*. In some embodiments, the bacteria comprises a further recombinant polynucleotide encoding an acetolactate synthase (ALS), an acetohydroxy acid isomeroreductase (AHIR), and a dihydroxy acid dehydratase (DHAD), wherein expression of the ALS, AHIR and DHAD results in an increase in production of isobutyraldehyde as compared to corresponding bacteria (e.g., same genus and species) lacking the further recombinant polynucleotide. In some embodiments, the ALS is AlsS. In other embodiments, the ALS is a homolog of AlsS having at least 85%, at least 90% or at least 95% sequence identity to AlsS encoded by alsS of *L. lactis*. In some embodiments, the AHIR is IlvC. In other embodiments, the AHIR is a homolog of IlvC having at least 85%, at least 90% or at least 95% sequence identity to IlvC encoded by ilvC of *E. coli*. In some embodiments, the DHAD is IlvD. In other embodiments, the DHAD is a homolog of IlvD having at least 85%, at least 90% or at least 95% sequence identity to IlvD encoded by ilvD of *E. coli*. In some embodiment, the further recombinant polynucleotide further encodes an alcohol dehydrogenase and wherein expression of the alcohol dehydrogenase along with the ALS, AHIR and DHAD results in an increase in production of the ester as compared to a corresponding bacterium lacking the recombinant polynucleotide and the further recombinant polynucleotide. In some embodiments, the bacteria further comprise a mutation in an alcohol dehydrogenase gene, wherein the mutation reduces alcohol dehydrogenase (ALD) activity of a product of the gene. In specific embodiments, the alcohol dehydrogenase gene comprises adhE. In some embodiments, the bacteria further comprise a mutation in an isobutyraldehyde reductase gene, wherein the mutation reduces isobutyraldehyde reductase (IBR) activity of the product of the gene. In specific embodiments, the isobutryaldehyde reductase gene comprises one or any combination of the yqhD, adhP, eutG, yjgB, and fucO genes. In some embodiments, the mutation is a functional deletion of each of adhE, yqhD, adhP, eutG, yiaY, yjgB, betA, and fucO genes. In one aspect, the bacterium further comprises a functional deletion in each of fnr, ldhA, frdBC, pflB, and pta genes. In yet other embodiments, the bacteria further comprise a functional deletion in each of eutE, yahK, ybbO, gldA, dkgAlyqhE, and yghA genes. In one aspect, one or both of the recombinant polynucleotide and the further recombinant polynucleotide are stably integrated into the genome of the bacteria. In some embodiments, the bacteria is *E. coli*. In other embodiments, the bacteria is an enterobacterium. In yet other embodiments, the bacteria is an *Escherichia* sp. The present disclosure also provides bacteria comprising a recombinant polynucleotide encoding an alcohol transferase (ATF) and a LuxCDE enzyme system, wherein expression of the ATF and the LuxCDE enzyme system results in an increase in production of an ester as compared to a corresponding bacterium lacking the recombinant polynucleotide. In further embodiments, the present disclosure provides bacteria comprising a recombinant polynucleotide encoding an acetyl transferase (AcTF) and either a 2-keto acid decarboxylase (KDC) or a 2-ketoisovalerate dehydrogenase enzyme complex (KIVDH), wherein expression of the AcTF and either the KDC or the KIVDH results in an increase in production of an ester as compared to a corresponding bacterium lacking the recombinant polynucleotide. Additionally, the present disclosure provides bacteria comprising a recombinant polynucleotide encoding a) an alcohol transferase (ATF) or acetyl transferase (AcTF); b) a 2-keto acid decarboxylase (KDC) or a 2-ketoisovalerate dehydrogenase enzyme complex (KIVDH); and c) an acetolactate synthase (ALS), an acetohydroxy acid isomeroreductase (AHIR), and a dihydroxy acid dehydratase (DHAD), wherein expression of the ATF or the AcTF, the KDC or the KIVDH, and the ALS, AHIR and DHAD results in an increase in production of an ester as compared to a corresponding bacterium lacking the recombinant polynucleotide. Moreover, the present disclosure provides bacteria comprising a recombinant polynucleotide encoding acetate kinase A (AckA) and phosphate acetyltransferase (Pta), wherein expression of AckA and Pta permits the bacterium to grow in culture medium comprising acetate. In some embodiments, the bacterium further comprises a mutation in a pyruvate dehydrogenase complex (PDHC) gene, wherein said mutation reduces pyruvate dehydrogenase activity of a product of said gene.

In addition, the disclosure provides methods for producing an ester. The methods include a) providing the bacteria as described in the preceding paragraph; and b) culturing the bacteria of (a) in culture medium comprising a substrate under conditions suitable for the conversion of the substrate to an ester, wherein expression of the ATF and either the KDC or the KIVDH results in an increase in production of the ester as compared to corresponding bacteria (e.g., same genus and species) lacking the recombinant polynucleotide, when cultured under the same conditions. In some embodiments, the methods further include substantially purifying the ester. In some embodiments, the ester is substantially purified by gas stripping. In other embodiments, the ester is substantially purified by siphoning. In yet other embodiments, the ester is substantially purified by organic extraction followed by distillation. In some embodiments, the ester comprises one or both of an acetate ester and an isobutyrate ester. The method of claim 27, wherein the substrate comprises one or more of the group consisting of glucose, a 2-keto acid and a C2-C10 straight chain alcohol. In some embodiments, step (b) comprises use of an alkane hydrocarbon to remove the ester produced by the bacterium. In specific embodiments, the ester is an acetate ester comprising isobutyl acetate, and step (b) comprises use of hexadecane to remove the isobutyl acetate produced by the bacterium.

A bacterium comprising a recombinant polynucleotide encoding an alcohol transferase (ATF) and a LuxCDE enzyme system, wherein expression of the ATF and the LuxCDE enzyme system results in an increase in production of an ester as compared to a corresponding bacterium lacking the recombinant polynucleotide.

A bacterium comprising a recombinant polynucleotide encoding an acetyl transferase (AcTF) and either a 2-keto acid decarboxylase (KDC) or a 2-ketoisovalerate dehydrogenase enzyme complex (KIVDH), wherein expression of the AcTF and either the KDC or the KIVDH results in an increase in production of an ester as compared to a corresponding bacterium lacking the recombinant polynucleotide.

A bacterium comprising a recombinant polynucleotide encoding
a) an alcohol transferase (ATF) or acetyl transferase (AcTF);
b) a 2-keto acid decarboxylase (KDC) or a 2-ketoisovalerate dehydrogenase enzyme complex (KIVDH); and
c) an acetolactate synthase (ALS), an acetohydroxy acid isomeroreductase (AHIR), and a dihydroxy acid dehydratase (DHAD),
wherein expression of the ATF or the AcTF, the KDC or the KIVDH, and the ALS, AHIR and DHAD results in an increase in production of an ester as compared to a corresponding bacterium lacking the recombinant polynucleotide.

A bacterium comprising a recombinant polynucleotide encoding acetate kinase A (AckA) and phosphate acetyltransferase (Pta), wherein expression of AckA and Pta permits the bacterium to grow in culture medium comprising acetate.

Wherein the bacterium the bacterium further comprises a mutation in a pyruvate dehydrogenase complex (PDHC) gene, wherein said mutation reduces pyruvate dehydrogenase activity of a product of said gene.

Furthermore the present disclosure provides methods for producing isobutyl isobutyrate. The methods include a) providing bacteria encoding an alcohol transferase (ATF) and a 2-ketoisovalerate dehydrogenase enzyme complex (KIVDH); and b) culturing the bacterium of (a) in culture medium comprising isobutanol under conditions suitable for the conversion of the isobutanol to isobutyl isobutyrate, wherein expression of the ATF and the KIVDH results in an increase in production of isobutyl isobutyrate as compared to corresponding bacteria (e.g., same genus and species) lacking the recombinant polynucleotide, when cultured under the same conditions. In some embodiments, the ATF is ATF1. In other embodiments, the ATF is a homolog of ATF1 having at least 85%, at least 90% or at least 95% sequence identity to ATF1 encoded by ATF1 of *S. cerevisiae*. In some embodiments, the ATF is EHT1. In other embodiments, the ATF is a homolog of EHT1 having at least 85%, at least 90% or at least 95% sequence identity to ATF encoded by EHT1 of *S. cerevisiae*. In some embodiments, the KIVDH is Kivdh. In other embodiments, the KIVDH is a homolog of Kivdh having at least 85%, at least 90% or at least 95% sequence identity to Kivdh encoded by kivdh of *P. putida*.

BRIEF DESCRIPTION OF THE DRAWINGS

FIG. 20A shows a diagram of three acetate assimilating pathways. FIG. 20B shows growth of recombinant bacteria in the presence of glucose, while FIG. 20C shows growth of recombinant bacteria in the presence of acetate. Overnight cultures of JCL260 were grown in 3 mL Luria Broth containing appropriate antibiotics. The overnight cultures were inoculated 1% in 5 mL M9 minimal media (containing appropriate antibiotics and 1 mM IPTG) with 10 g/L glucose or 10 g/L acetate in 15-ml screw-cap tubes. Cells were grown at 37° C. on a rotary shaker (250 rpm), and $OD_{600}$ of these cultures was measured.

DETAILED DESCRIPTION OF THE INVENTION

Figure 1:
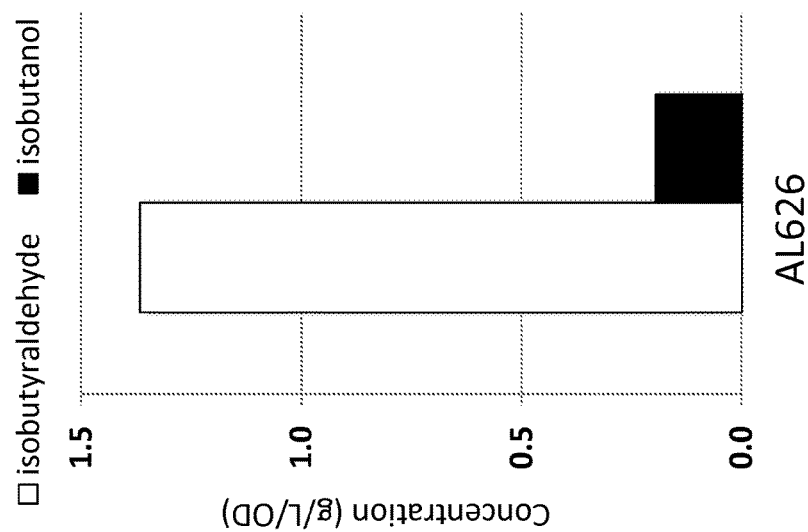
FIG. 1 demonstrates the production of isobutyraldehyde and isobutanol, by the recombinant *E. coli* strain AL626 (JCL16 with ΔadhE Δfnr-ΔldhA ΔfrdBC ΔpflB Δpta ΔyqhD ΔadhP ΔeutG ΔyiaY ΔyjgB ΔbetA ΔfucO).

The present disclosure provides recombinant bacteria with elevated 2-keto acid decarboxylase and alcohol transferase activities. Some recombinant bacteria further have elevated aldehyde dehydrogenase activity. Some recombinant bacteria further have reduced alcohol dehydrogenase and/or aldehyde reductase activity. Methods for the production of the recombinant bacteria, as well as for use thereof for production of various esters are also provided.

In particular, the present disclosure provides cost-effective and environmentally-friendly approaches for producing esters. Ester production is ideally suited for microbial production because of the hydrophobic nature of these molecules. Due to the limited water solubility of esters, when recombinant bacteria cultured in an aqueous medium produce an appreciable quantity, the esters separate from the medium forming a bilayer. This allows for continuous ester production with limited toxicity to the host cells, and further simplifies ester purification.

Bacteria Engineered for Ester Production

The present disclosure provides recombinant bacteria for use in the production of an ester (e.g., acetate and/or isobutyrate esters). The bacteria contain a recombinant polynucleotide encoding an alcohol transferase (ATF) and either a 2-keto acid decarboxylase (KDC) or a 2-ketoisovalerate dehydrogenase enzyme complex (KIVDH). Expression of the ATF and either the KDC or the KIVDH results in an increase in production of an ester by the bacteria as compared to corresponding bacteria lacking the polynucleotide (e.g., same genus and species) when cultured under the same conditions. In some bacteria, the recombinant polynucleotide further encodes an aldehyde dehydrogenase (ALDH), and expression of ALDH along with the ATF and either the KDC or the KIVDH results in an increase in production of an ester by the bacteria as compared to corresponding bacteria lacking the polynucleotide (e.g., same genus and species). In some embodiments, the recombinant polynucleotide comprises one, two or three polynucleotides, each encoding at least one of the ATF, either the KDC or the KIVDH, and optionally the ALDH. In some preferred embodiments, the bacteria contain a further recombinant polynucleotide encoding an acetolactate synthase (ALS), an acetohydroxy acid isomeroreductase (AHIR), and a dihydroxy acid dehydratase (DHAD). Expression of the ALS, the AHIR and the DHAD results in an increase in production of isobutyraldehyde by the bacteria as compared to corresponding bacteria lacking the further recombinant polynucleotide. Some bacteria further have a mutation (e.g., functional deletion) in a gene encoding an alcohol dehydrogenase (ADH) and/or an isobutyraldehyde reductase (IBR), which decreases activity of the ADH and/or the IBR, respectively.

Also provided are recombinant vectors, expression cassettes and polynucleotides comprising coding sequences of one or more of the ATF, the KDC or the KIVDH, and the ALDH. In some embodiments, the nucleic acid constructs are used to produce recombinant bacteria for biosynthetic production of an ester.

Enzymes

Table 1 provides accession numbers of genes that have been mutated (physically or functionally deleted) from various recombinant bacteria of the present disclosure, while Table II provides accession numbers of the genes that have been inserted in various recombinant bacteria of the present disclosure.

TABLE I

Mutated Genes

| Mutated Gene(s) | EcoGene No. | Enzyme NCBI No. | IBR |
|---|---|---|---|
| ldhA (htpH, hslF, hslI) | EG13186 | NP_415898 | − |
| frdABCD | EG10330 | YP_492299.1 | − |
|  | EG10331 | YP_492298.1 |  |
|  | EG10332 | YP_492297.1 |  |
|  | EG10333 | YP_492296.1 |  |
| pta | EG20173 | YP_490539.1 | − |
| fnr (frdB, nirA, nirR, ossA, oxrA) | EG10325 | YP_489604.1 | − |
| pflB (pfl) | EG10701 | YP_489175.1 | − |
| adhE (adhC, ana) | EG10031 | NP_415757 | − |
| yqhD | EG13014 | NP_417484 | + |
| adhP (yddN) | EG12622 | NP_415995 | + |
| eutG (yffV) | EG14183 | NP_416948 | + |
| yiaY | EG12293 | YP_026233 | − |
| yjgB (ahr) | EG11436 | NP_418257 | + |
| beta | EG10109 | NP_414845 | − |
| fucO | EG10351 | NP_417279 | + |
| eutE (yffX) | EG14185 | NP_416950 | − |
| yahK | EG13595 | NP_414859 | + |
| ybbO | EG13262 | NP_415026 | + |
| dkgA (yqhE, AKR5C2) | EG13015 | NP_417485 | + |
| gldA | EG11904 | NP_418380 | + |
| yghA | EG11292 | NP_417476 | + |
| aceE | EG10024 | NP_414656 |  |
| aceF | EG10025 | NP_414657 |  |
| lpd | EG10543 | NP_414658 |  |

TABLE II

Inserted Genes

| Inserted Gene | Source | EcoGene No. | Enzyme NCBI No. |
|---|---|---|---|
| kivd | L. lactis | — | CAG34226.1 |
| mhpF | E. coli | EG13625 | NP_414885 |
| ATF1 | S. cerevisiae | — | NP_015022.3 |
| alsS | B. subtilis | — | CAB07802.1 |
| ilvC | E. coli | EG10495 | NP_418222 |
| ilvD | E. coli | EG10496 | YP_026248 |
| leuA | E. coli | EG11226 | YP_488380.1 |
| leuCD | E. coli | EG11576 | YP_488378.1 |
|  |  | EG11575 | YP_488377.1 |
| leuB | E. coli | EG11577 | YP_488379.1 |
| ilvA | E. coli | EG10493 | YP_491666.1 |
| pheA | E. coli | EG10707 | YP_490822.1 |
| tyrA | E. coli | EG11039 | YP_490823.1 |
| kivdh (KDHC) (BCKD Complex): | P. putida F1 | — |  |
| Pput_1450 (bkdA1) |  |  | YP_001266792.1 |
| Pput_1451 (bkdA2) |  |  | YP_001266793.1 |
| Pput_1452 (bkdB) |  |  | YP_001266794.1 |
| Pput_1453 (lpdV) |  |  | YP_001266795.1 |
| EEB | S. cerevisiae |  | NP_015230.1 |
| EHT1 | S. cerevisiae |  | NP_009736.3 |

TABLE II-continued

Inserted Genes

| Inserted Gene | Source | EcoGene No. | Enzyme NCBI No. |
|---|---|---|---|
| mrfp | Discosoma sp. | — | AAM54544.1 |
| adhA | L. lactis | — | WP_003130326.1 |
| luxC | V. harveyi | — | ABX76844.1 |
| luxD | V. harveyi | — | ABX76845.1 |
| luxE | V. harveyi | — | ABX76848.1 |
| cmR | C. scindens | — | WP_002361567.1 |
| ackA | E. coli | EG10027 |  |
| pta | E. coli | EG20173 | YP_490539.1 |
| aldB | E. coli | EG12292 |  |
| edgE | L. monocytogenes | — | NP_464704.1 |

Several classification schemes exist to enable one of skill to identify homologous genes, or proteins with homologous functions or enzymatic properties, across various bacterial species. Enzymatic reactions can be classified according to their Enzyme Commission (EC) number. The EC number associated with a given enzyme specifies the classification of the type of enzymatic reaction that a given enzyme is capable of catalyzing. EC numbers do not specify identities of enzymes, but instead specify the identity of the chemical reaction that a given enzyme catalyzes. Similarly, proteins can also be assigned Gene Ontology (GO) terms. GO terms attempt to further define the given role and/or function of a protein in a living organism by specifying protein function in terms of a cellular component, a biological process, and/or a molecular function. For example, two enzymes from two different species of organisms that catalyze the same chemical reaction could be assigned the same EC classification and GO term annotation, despite that the respective enzymes are endogenous to different organisms. EC and GO term classifications are helpful to those skilled in the art in identifying the molecular function and/or activity of a given protein outside of knowing its unique identifying classification with regard to the organism it came from, such as its NCBI (National Council for Biotechnology) identifier. EC and GO term classifications may encompass broad or very narrow enzymatic activities and functions, and many proteins are classified under several often overlapping EC and GO terms. The classifications listed in this disclosure are included to describe enzymes and genes that could be utilized in certain embodiments. They are provided to help those skilled in the art understand the enzymatic activity or class of interest and are not meant to limit or restrict choice of enzymes in the embodiments.

Enzymes for Ester Production 2-keto acid decarboxylase (KDC) activity converts 2-ketoisovalerate to isobutyraldehyde and also generates the precursors for branched chain alcohols (including isobutanol, isoamyl alcohol, and phenyl ethanol). Aldehyde dehydrogenase (ALDH) activity converts isobutyraldehyde into isobutyryl-CoA. Similarly, 2-ketoisovalerate dehydrogenase (KIVDH) activity converts 2-ketoisovalerate into isobutyryl-CoA. Alcohol transferase (ATF) activity combines various alcohols (including branched chain alcohols) with acetyl-CoA or isobutyryl-CoA to yield the corresponding esters. Thus these enzymatic activities catalyze sequential chemical reactions that ultimately convert 2-ketoisovalerate into esters. While certain microbes are able to generate a few acetate esters, these esters are produced as side products only in trace amounts (and therefore unsuitable for industrial production). For example, during beer brewing, various yeasts are known to produce ethyl, isoamyl, and phenethyl acetate, but only up to an approximate concentration of 60 ppm, or 0.0062% (Smart, Brewing Yeast Fermentation Performance, 2$^{nd}$ ed. Hoboken: Wiley-Blackwell; 2002). The expression of an ATF and either a KDC or a KIVDH in bacteria confer the ability to produce high titers of acetate esters. Further expression of an ALDH in bacteria confer the ability to produce high titers of isoamyl acetate. Likewise, the expression of an ATF and a KIVDH in bacteria confer the ability to produce high titers of isobutyrate esters. Thus in some embodiments, bacteria having elevated 2-ketoisovalerate dehydrogenase (KIVDH) and alcohol transferase (ATF) activities are provided. In other embodiments, bacteria having elevated 2-keto acid decarboxylase (KDC), aldehyde dehydrogenase (ALDH), and alcohol transferase (ATF) activities are provided.

In some embodiments, the 2-keto-acid decarboxylase (KDC) is encoded by a polynucleotide comprising a kivd gene from *Lactococcus lactis*, or homolog thereof. Kivd belongs to a class of enzymes called 2-keto acid, or branched chain alpha-ketoacid, decarboxylases. Specifically, Kivd is a non-oxidative thiamin disphosphate (ThDP)-dependent 2-keto acid decarboxylase (de la Plaza et al., FEMS Microbiol Lett 238: 367-74, 2004). 2-keto acid decarboxylases catalyze the chemical conversion of a 2-keto carboxylate into a corresponding aldehyde and carbon dioxide. This enzymatic reaction belongs to the classifications EC 4.1.1.1, EC 4.1.1.72, or EC 4.1.1.74. 2-keto acid decarboxylases share the molecular function of GO term IDs GO: 0016831 (decarboxylase activity) and/or GO: 0004737 (2-keto-acid decarboxylase activity). Any protein characterized with these EC classifications and/or GO terms may possess catalytic 2-keto-acid decarboxylase activity. Other KDCs known in the art include but are not limited to:
gi|428770248|ref|YP_007162038.1| pyruvate decarboxylase [*Cyanobacterium aponinum*];
gi|470462934|ref|YP_007629245.1| pyruvate decarboxylase [*Edwardsiella tarda* C07-087];
gi|325106918|ref|YP_004267986.1| pyruvate decarboxylase [*Planctomyces brasiliensis*];
gi|20385191|gb|AAM21208.1|AF368435_1 pyruvate decarboxylase [*Acetobacter pasteurianus*];
gi|506381688|ref|WP_015901407.1| pyruvate decarboxylase [*Staphylococcus carnosus*];
gi|475988405|gb|EMU49652.1| pyruvate decarboxylase [*Acinetobacter baumannii* ABNIH24];
gi|167374781|gb|ABZ79223.1|pyruvate decarboxylase [*Prunus armeniaca*];
gi|453062165|gb|EMF03157.1| pyruvate decarboxylase [*Serratia marcescens* VGH107];
gi|496457580|ref|WP_009166425.1| pyruvate decarboxylase [*Lactobacillus florum*]; and
gi|493981100|ref|WP_006924020.1| pyruvate decarboxylase [*Bacillus* sp. GeD10].

In some embodiments, the 2-ketoisovalerate dehydrogenase enzyme complex (KIVDH) is encoded by a polynucleotide comprising a bckd gene complex from *P. putida*, or a homolog thereof. KIVDH complexes refer to multienzyme complexes that catalyze the oxidative decarboxylation of branched chain or 2-oxo keto acids. The terms branched-chain α-ketoacid dehydrogenase complex (BCKD or BCKDC) and 2-oxo acid dehydrogenase complex may be used interchangeably. Generally, these complexes may include enzymes belonging to three functional classes: an E1 oxoglutarate dehydrogenase (belonging to the classification EC 1.2.4.2 and the molecular function of GO term ID GO: 0004591), an E2 dihydrolipoamide succinyltransferase (belonging to the classification EC 2.3.1.61 and the molecular function of GO term ID GO: 0004149), and an E3 lipoamide dehydrogenase (belonging to the classification EC 1.8.1.4 and the molecular function of GO term ID GO: 0004148). Any complex characterized with these EC classifications and/or GO terms may possess catalytic KIVDH activity. KIVDH complexes catalyze the reaction converting a branched chain α-ketoacid and a coenzyme A moiety into an acid-CoA thioester, generating carbon dioxide and NADH. KIVDH complexes may be found in many types of organisms, including bacteria, plants, and animals, and they participate in many biochemical pathways, including for example the catabolism of branched chain amino acids and the synthesis of branched hydrocarbons and branched long chain fatty acids.

Many KIVDH complexes contain four types of subunits: E1α, E1β, E2, and E3. In some embodiments, the KIVDH complex is encoded by individual polynucleotides taken from the same species of origin. In other embodiments, the KIVDH complex is encoded by individual polynucleotides taken from different species of origin. Genes encoding the subunits of a KIVDH complex may be part of the same polynucleotide controlled by the same regulatory sequence (as with a bacterial operon), or they may be encoded by separate polynucleotides and/or controlled by different regulatory sequences. The bckd gene complex in *Pseudomonas putida* includes the genes bkdA (encoding an E1α subunit), bkdA2 (encoding an E1β subunit), bkdB (encoding an E2 subunit), and bkdC (encoding an E3 subunit).

Other E1 subunits known in the art include but are not limited to:
gi|5600208|ref|NP_253702.1| pyruvate dehydrogenase subunit E1 [*Pseudomonas aeruginosa*];
gi|31618030|emb|CAD94141.1|(Alpha-ketoglutarate dehydrogenase) [*Mycobacterium bovis*];
gi|218896295|ref|YP_002444706.1|2-oxoglutarate dehydrogenase E1 [*Bacillus cereus* G9842];
gi|26246693|ref|NP_752733.1|2-oxoglutarate dehydrogenase E1 [*Escherichia coli* CFT073];
gi|255985847|ref|YP_354049.3|2-oxoglutarate dehydrogenase E1 [*Rhodobacter sphaeroides*];
and gi|32895136|ref|YP_004368696.1|2-oxoglutarate dehydrogenase, E1 [*Marinithermus hydrothermalis* DSM 14884].

Other E2 subunits known in the art include but are not limited to:
gi|16128702|ref|NP_415255.1| dihydrolipoyltranssuccinase [*Escherichia coli* K-12, MG1655];
gi|15892149|ref|NP_359863.1| dihydrolipoamide succinyltransferase [*Rickettsia conorii*];
gi|332659867|gb|AEE85267.1| dihydrolipoamide succinyltransferase [*Arabidopsis thaliana*];
gi|21220655|ref|NP_626434.1| dihydrolipoamide succinyltransferase [*Streptomyces coelicolor*];
and gi|339468289|gb|EGP83390.1| dihydrolipoamide succinyltransferase [*Zymoseptoria tritici*].

Other E3 subunits known in the art include but are not limited to:
gi|255767526|ref|NP_390286.2| dihydrolipoamide dehydrogenase [*Bacillus subtilis*];
gi|488605715|ref|YP_007921292.1| dihydrolipoyl dehydrogenase [*Burkholderia thailandensis*];
gi|428683469|gb|AFZ52936.1|Dihydrolipoyl dehydrogenase [*Cyanobacterium aponinum*];
gi|427988196|gb|AFY68451.1|Dihydrolipoyl dehydrogenase [*Pseudanabaena* sp. PCC 7367];
and gi|332658304|gb|AEE83704.1| dihydrolipoyl dehydrogenase [*Arabidopsis thaliana*].

In some embodiments, the aldehyde dehydrogenase (ALDH) is encoded by a polynucleotide comprising a mhpF gene from *E. coli*, or homolog thereof. MhpF belongs to a class of enzymes known as acylating acetaldehyde dehydrogenases. Acylating acetaldehyde dehydrogenases catalyze the chemical conversion of an aldehyde and a coenzyme A moiety into a corresponding acid-CoA thioester (for example, acetyl-CoA or isobutyryl-CoA), using NAD+ as a cofactor. This enzymatic reaction belongs to the classification EC 1.2.1.10. Acylating acetaldehyde dehydrogenases share the molecular function of GO term ID GO: 0008774 (acetaldehyde dehydrogenase (acetylating) activity). Any protein characterized with these EC classifications and/or GO terms may possess catalytic aldehyde dehydrogenase activity. One endogenous function of mhpF in *E. coli* is participating in the meta-cleavage pathway for the catabolism of aromatic compounds, including phenols. Other acylating acetaldehyde dehydrogenases known in the art include but are not limited to:

gi|445966456|ref|WP_000044311.1| acetaldehyde dehydrogenase [*Shigella boydii*];

gi|489927591|ref|WP_003830924.1|acetaldehyde dehydrogenase [*Citrobacter freundii*];

gi|493736596|ref|WP_006685798.1|acetaldehyde dehydrogenase [*Citrobacter youngae*];

gi|491266892|ref|WP_005125029.1|acetaldehyde dehydrogenase [*Shigella flexneri*];

gi|481848664|ref|YP_007873104.1|acetaldehyde dehydrogenase [*Raoultella ornithinolytica* B6];

gi|490220834|ref|WP_004119206.1|acetaldehyde dehydrogenase [*Klebsiella oxytoca*];

gi|490308019|ref|WP_004203053.1|acetaldehyde dehydrogenase [*Klebsiella pneumoniae*]; and gi|495204152|ref|WP_007928933.1|acetaldehyde dehydrogenase [*Pseudomonas* sp. GM 17].

Some embodiments include the use of a polynucleotide encoding an alcohol transferase (ATF). In some embodiments, the alcohol transferase (ATF) is encoded by a polynucleotide comprising an ATF1 gene from *S. cerevisiae*, or homolog thereof. ATF1 belongs to a class of enzymes known as alcohol O-acetyltransferases. Alcohol O-acetyltransferases catalyze the chemical conversion of an acid-CoA thioester (for example, acetyl-CoA or isobutyryl-CoA) and an alcohol into a corresponding ester. This enzymatic reaction belongs to the classification EC 2.3.1.84. Alcohol O-acetyltransferases share the molecular function of GO term ID GO: 0004026 (alcohol O-acetyltransferase activity). Any protein characterized with these EC classifications and/or GO terms may possess catalytic alcohol O-acetyltransferase activity. Atf1p catalyzes the formation of volatile ester compounds in trace amounts during fermentation; these esters are known to contribute distinctive aromas to wine and beer. Other alcohol O-acetyltransferases known in the art include but are not limited to:

gi|34485572|gb|AAP72991.1|alcohol acetyltransferase I [*Saccharomyces pastorianus*];

gi|401841552|gb|EJT43925.1|ATF1-like protein [*Saccharomyces kudriavzevii* IFO 1802];

gi|406602085|emb|CCH46328.1|alcohol O-acetyltransferase 1 [*Wickerhamomyces ciferrii*];

gi|448521835|ref|XP_003868581.1|Atf1 alcohol acetyltransferase [*Candida orthopsilosis*];

gi|68465463|ref|XP_723093.1| possible alcohol acetyltransferase [*Candida albicans* SC5314];

gi|255712859|ref|XP_002552712.1|KLTH0C11440p [*Lachancea thermotolerans*]; and gi|401623456|gb|EJS41554.1|atf1p [*Saccharomyces arboricola* H-6].

In other embodiments, the alcohol transferase (ATF) is encoded by a polynucleotide comprising an EHT1 gene from *S. cerevisiae*, or homolog thereof. EHT1 belongs to the subclass of ATF enzymes known as alcohol O-butanoyltransferases that catalyze the chemical conversion of a butanoyl-CoA thioester and an alcohol into a corresponding butyl ester. Alcohol O-butanoyltransferases share the molecular function of GO term ID GO: 0034319. Any protein characterized as having this GO term may possess catalytic alcohol O-butanoyltransferase, and hence alcohol transferase, activity. EHT1 is known to contribute to the formation of medium chain fatty acid ethyl esters in *S. cerevisiae*.

Enzymes for Aldehyde Production

In some embodiments, bacteria having elevated acetolactate synthase (ALS), acetohydroxy acid isomeroreductase (AHIR), and dihydroxy-acid dehydratase (DHAD) activities are provided. These enzymes function in the bacterial biosynthetic pathways that produce the amino acids valine and isoleucine. The valine and isoleucine biosynthesis pathways in *E. coli* and other bacteria share the same metabolic enzymes and can be utilized to enhance the production of 2-ketoisovalerate from pyruvate. To increase the activity of valine biosynthesis pathway and isoleucine biosynthesis pathway, recombinant bacteria can be engineered to have elevated expression or activity of acetolactate synthase (;), acetohydroxy acid isomeroreductase, and dihydroxy-acid dehydratase. In some embodiments, bacteria having elevated expression or activity of AlsS, IlvC, and IlvD, or homologs thereof, are provided In some embodiments, the acetolactate synthase (ALS) is encoded by a polynucleotide comprising an alsS gene from *Bacillus subtilis*. Acetolactate synthases, including AlsS, catalyze the conversion of pyruvate into acetolactate and carbon dioxide. This enzymatic reaction belongs to the classification EC 2.2.1.6. Acetolactate synthases share the molecular function of GO term ID GO: 0003984. Any protein characterized with these EC classifications and/or GO terms may possess catalytic acetolactate synthase activity. In addition to participating in the synthesis of branched chain amino acids, acetolactate synthases may also be involved in acetoin synthesis. Other acetolactate synthases known in the art include but are not limited to:

gi|332644909|gb|AEE78430.1|acetolactate synthase [*Arabidopsis thaliana*];

gi|428268313|gb|AFZ34254.1| Acetolactate synthase [*Stanieria cyanosphaera* PCC 7437];

gi|428238981|gb|AFZ04767.1|Acetolactate synthase [*Oscillatoria nigro-viridis* PCC 7112];

gi|427988202|gb|AFY68457.1|Acetolactate synthase [*Pseudanabaena* sp. PCC 7367];

gi|311224567|gb|ADP77423.1|Acetolactate synthase [*Methanothermus fervidus* DSM 2088];

gi|363716653|gb|EHM00051.1|acetolactate synthase [*Acetobacteraceae bacterium* AT-5844];

and gi|357547224|gb|EHJ29116.1|acetolactate synthase [*Lactobacillus rhamnosus*].

In some embodiments, the acetohydroxy acid isomeroreductase (AHIR) is encoded by a polynucleotide comprising an ilvC gene from *E. coli*. Acetohydroxy acid isomeroreductases (also known as ketol-acid reductoisomerases), including IlvC, catalyze the conversion of (R)-2,3-dihydroxy-3-methylbutanoate to (S)-2-hydroxy-2-methyl-3-oxobutanoate. This enzymatic reaction belongs to the classification EC 1.1.1.86. Acetohydroxy acid isomeroreductases share the molecular function of GO term ID GO: 0004455. Any protein characterized with these EC classifications and/or GO terms may possess catalytic acetohydroxy acid isomeroreductase activity. In addition to participating in the synthesis of branched chain amino acids, acetohydroxy acid isomeroreductases may also be involved in the synthesis of CoA and pantothenate. Other acetohydroxy acid isomeroreductases known in the art include but are not limited to:

gi|386347434|ref|YP_006045683.1|AHIR [*Spirochaeta thermophila* DSM 6578];

gi|251771676|gb|EES52251.1|AHIR [*Leptospirillum ferrodiazotrophum*];

gi|158280671|gb|EDP06428.1 AHIR [*Chlamydomonas reinhardtii*];

gi|6491802|emb|CAB61890.1|acetohydroxy acid isomeroreductase [*Pisum sativum*];

gi|642665|gb|AAA93100.1|acetohydroxy acid isomeroreductase [*Streptomyces avermitilis*];

gi|49532082|emb|CAG69794.1|acetohydroxy acid isomeroreductase [*Acinetobacter* sp. ADP1];

and gi|409247592|ref|YP_006888288.1|Ketol-acid reductoisomerase [*Salmonella enterica*].

In some embodiments, the dihydroxy-acid dehydratase (DHAD) is encoded by a polynucleotide comprising an ilvD gene from *E. coli*. Dihydroxy-acid dehydratases, including IlvD, catalyze the conversion of 2,3-dihydroxy-3-methylbutanoate to 3-methyl-2-oxobutanoate. This enzymatic reaction belongs to the classification EC 4.2.1.9. Dihydroxy-acid dehydratases share the molecular function of GO term ID GO: 0004160. Any protein characterized with these EC classifications and/or GO terms may possess catalytic dihydroxy-acid dehydratase activity. In addition to participating in the synthesis of branched chain amino acids, dihydroxy-acid dehydratases may also be involved in the synthesis of CoA and pantothenate. Other dihydroxy-acid dehydratases known in the art include but are not limited to:

gi|330838997|ref|YP_004413577.1|Dihydroxy-acid dehydratase [*Selenomonas sputigena*];

gi|428244314|gb|AFZ10100.1|Dihydroxy-acid dehydratase [*Oscillatoria nigro-viridis*];

gi|427988966|gb|AFY69221.1|Dihydroxy-acid dehydratase [*Pseudanabaena* sp. PCC 7367];

gi|361057512|gb|AEV96503.1 Dihydroxy-acid dehydratase [*Niastella koreensis* GR20-10];

gi|325297988|ref|YP_004257905.1|Dihydroxy-acid dehydratase [*Bacteroides salanitronis*];

gi|325282609|ref|YP_004255150.1|Dihydroxy-acid dehydratase [*Deinococcus proteolyticus*];

and gi|328450793|gb|AEB11694.1|Dihydroxy-acid dehydratase [*Marinithermus hydrothermalis*].

Enzymes with Alcohol Dehydrogenase and/or Isobutyraldehyde Reductase Activities

In some embodiments, bacteria with mutations reducing alcohol dehydrogenase (ADH) and/or isobutyraldehyde reductase (IBR) activities are provided. Enzymes having these catalytic activities promote both the forward and reverse chemical reactions that interconvert alcohols and their corresponding aldehydes or ketones. ADH and IBR gene products may be identified as having EC classification 1.1.1.1 and/or GO term ID GO: 0004022. Bacteria comprising mutations in multiple, specific ADH/IBR genes are able to produce higher amounts of isobutyraldehyde than wild type bacteria of the same species because the conversion of isobutyraldehyde to isobutanol is substantially reduced. This in turn allows for higher production of isobutyraldehyde-derived esters by the methods of the present disclosure.

Bacterial alcohol dehydrogenase and isobutyraldehyde reductase enzymes share a high degree of redundancy, and multiple genetic mutations are required to obtain a strain with substantially reduced alcohol dehydrogenase and/or isobutyraldehyde reductase activity. *E. coli*, as a non-limiting example, have six different isobutyraldehyde reductases (IBRs), adhE, yqhD, adhP, eutG, yjgB, and fucO, which contribute to most of the endogenous isobutyraldehyde reductase activity. Furthermore, *E. coli* have six different alcohol dehydrogenases (ADHs), adhE, yqhD, adhP, eutG, yiaY, and yjgB, which contribute to most of the endogenous alcohol dehydrogenase activity. Therefore, *E. coli* lacking adhE, yqhD, adhP, eutG, yiaY, yjgB, betA, and fucO have substantially reduced alcohol dehydrogenase and/or isobutyraldehyde reductase activity as compared to wild type *E. coli*. The bacterium may further include the deletion or inhibition of expression of ldh (e.g., an ldhA), frd (e.g., an frdB, an frdC or an frdBC), fnr, ilvE, ilvA, poxB, pflB, leuA or pta gene, or any combination thereof, to reduce the activity of competing pathways.

In addition to the aforementioned ADH and/or IBR genes, *E. coli* and other bacteria contain yet more enzymes with isobutyraldehyde reductase activity. Further genes encode enzymes with isobutyraldehyde reductase activity, including but not limited to yahK, ybbO, gldA, dkgA (yqhE), and yghA. When mutated in combination in recombinant bacteria, their loss results in a reduction in IBR activity and in the decreased production of isobutanol as compared to bacteria comprising functional IBR genes. Therefore, these mutations even further reduce isobutanol production in a strain lacking adhE, yqhD, adhP, eutG, yiaY, yjgB, betA, and fucO. In some embodiments, recombinant bacteria additionally contain mutations in eutE, yahK, ybbO, gldA, dkgA/yqhE, and yghA or homologs thereof. Therefore, in some embodiments, recombinant bacteria may contain mutations in adhE, yqhD, adhP, eutG, fucO, yjgB, adhE, yqhD, adhP, eutG, fucO, yjgB eutE, yahK, ybbO, gldA, dkgA/yqhE, and yghA or homologs thereof.

In some embodiments, the acetolactate synthase (ALS) is encoded by a polynucleotide comprising an alsS gene from *Bacillus subtilis*. Acetolactate synthases, including AlsS, catalyze the conversion of pyruvate into acetolactate and carbon dioxide. This enzymatic reaction belongs to the classification EC 2.2.1.6. Acetolactate synthases share the molecular function of GO term ID GO: 0003984. Any protein characterized with these EC classifications and/or GO terms may possess catalytic acetolactate synthase activity. In addition to participating in the synthesis of branched chain amino acids, acetolactate synthases may also be involved in acetoin synthesis. Other acetolactate synthases known in the art include but are not limited to:

Methods for introducing recombinant polynucleotides into various bacterial species are known in the art (Current Protocols in Microbiology. Hoboken: Wiley, 2013; Neidhardt, F. C. *Escherichia coli* and *Salmonella*: Cellular and Molecular Biology. $2^{nd}$ ed. Washington, D.C.: ASM Press, 1996). Coding sequences or genes encoding recombinant proteins may be present within exogenous vectors (for example, a plasmid or bacterial artificial chromosome) that are introduced into the host bacterial cell. Alternatively, coding sequences or genes may be added directly to the host bacterial chromosome through techniques such as homologous recombination and recombineering. Polynucleotides engineered into the recombinant bacteria may further contain additional elements for the expression and/or regulation of expression of these genes, e.g. promoter sequences. Each recombinant gene may be regulated by its own promoter, or multiple recombinant genes may be controlled by the same promoter. Many methods for introducing exogenous vectors into bacteria are known in the art and include without limitation transformation by heat shock, DNA damage, electroporation, or phage infection. Similarly, methods for introducing mutations (including deletions) into genomes of a variety of bacterial species are known in the art. Mutations can be introduced by molecular biology means, such as homologous recombination, recombineering, gene replacement, or by chemical means, such as treatments with radiation or chemical agents followed by a secondary screening step wherein the strains are selected for the desired mutation.

Although *E. coli* genes are listed as exemplary enzyme-encoding genes, this choice of species is intended in no way to be limiting. If a different bacterium is used as the host, the homolog(s) of the *E. coli* gene(s) are mutated. Many tools common in the art exist to identify homologous genes in different species, including without limitation BLAST searching and alignment, EC classifications, and GO term annotations. As a further resource, the online PortEco project contains not only an annotation of the *E. coli* genome, but for each gene it also provides a table of homologous genes in other organisms, as well as further online tools to identify homologous genes in a variety of other organisms (McIntosh et al., Nucleic Acids Res, 40:D1270-7, 2013).

Bacterial Cells

The present disclosure provides recombinant bacteria. Any culturable bacteria are suitable for use in the compositions and methods described herein. The term "bacteria" refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, Micrococcus, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

Although *E. coli* was utilized in exemplary embodiments, the present disclosure is not limited to this genus and species of bacteria. It is understood that many bacterial species can be modified to possess elevated alcohol transferase activity and either elevated 2-keto acid decarboxylase or 2-ketoisovalerate dehydrogenase activity. Many bacterial species can also be utilized for the production of various esters. It is further understood that various microorganisms can act as "sources" for genetic material encoding target enzymes (e.g., 2-keto acid decarboxylases, 2-ketoisovalerate dehydrogenases, aldehyde dehydrogenases, and alcohol transferases) suitable for use in recombinant bacteria provided herein.

Exemplary embodiments use *E. coli* as the host bacterial species because of the extensive expertise and reagents available for this common model bacterium. However, protocols and reagents for recombinantly expressing proteins in a wide variety of bacterial host species are known in the art (Current Protocols in Microbiology. Hoboken: Wiley, 2013; Neidhardt, F. C. *Escherichia coli* and *Salmonella*: Cellular and Molecular Biology. $2^{nd}$ ed. Washington, D.C.: ASM Press, 1996). Furthermore, because of the physiological similarities between bacterial species, existing protocols and reagents for recombinantly expressing a polypeptide in one species (e.g., *E. coli*) may readily function without undue experimentation in another species.

Methods of Producing and Purifying Esters

The present disclosure provides methods of producing an ester (e.g., acetate and/or isobutyrate esters). These methods involve providing recombinant bacteria with one or more recombinant polynucleotides and culturing the recombinant bacteria in a culture medium with a substrate under conditions that enable the bacteria to convert the substrate into an ester, thereby producing an ester in higher amounts or at a higher rate than bacteria of the same species lacking the recombinant polynucleotides. In some embodiments, the recombinant bacteria may further contain functional deletion(s) in one or more genes. The methods of the present disclosure may be used to produce individual esters, or they may be used to produce mixtures of different esters.

In some embodiments, the methods for producing an ester include a culture medium for culturing the recombinant bacteria. "Culture medium" as used herein refers to any composition or broth that supports the growth of the bacteria of the present disclosure. Suitable culture media may be liquid or solid and contain any nutrients, salts, buffers, elements, and other compounds that support the growth and viability of cells. Common nutrients of a culture medium may include sources of nitrogen, carbon, amino acids, carbohydrates, trace elements, vitamins, and minerals. These nutrients may be added as individual components (as in a defined culture medium) or as constituents of a complex extract (for example, yeast extract). A culture medium may be nutrient-rich to support rapid growth or minimal to support slower growth. A culture medium may also contain any agent used to inhibit the growth of or kill contaminating organisms (e.g., an antibiotic). A culture medium may also contain any compound used to control the activity of an inducible promoter or enzyme (as one example, IPTG may be included to induce expression of any polynucleotides controlled by a lac operon or functionally similar promoter). Many examples of suitable culture media are well known in the art and include without limitation M9 medium, Lysogeny Broth (LB), Terrific Broth (TB), and YT broth.

In some embodiments, recombinant bacteria are cultured. Culturing bacteria refers to providing the bacteria with a suitable nutrient source (such as a culture medium of the present disclosure) under conditions that allow for bacterial growth. These conditions may include pH, temperature, gas levels (e.g., oxygen and carbon dioxide), pressure, light, and cell density. Suitable ranges for each of these parameters may differ depending upon the particular bacteria, desired metabolic state of the bacteria, or the activity of any enzymes expressed by the bacteria. Culturing conditions and methods suitable for a wide range of bacterial species are well known in the art.

In some embodiments, the culture medium contains a substrate that is converted by the recombinant bacteria to an ester. Suitable substrates may include any carbon source used by bacteria to produce acetyl-CoA, isobutyryl-CoA, pyruvate, an aldehyde, an ester, or an alcohol. In some embodiments, the substrate may be a reduced carbon source that is metabolized by the bacteria via glycolysis into pyruvate or acetyl-CoA (e.g., glucose, glycerol, sugars, starches, and lignocellulosics, including glucose derived from cellulose and $C_5$ sugars derived from hemicellulose, such as xylose). In some embodiments, the substrate may be an amino acid (e.g., valine or isoleucine) or a compound involved in an amino acid biosynthesis pathway. In preferred embodiments, the substrate may be isobutanol or ketoisovalerate. A substrate may be a constituent of the culture medium, or it may be exogenously supplemented to the culture medium. A substrate may be continuously present in the culture medium, or it may be supplemented during bacterial growth. A substrate may be present in any desired amount in the culture medium, depending upon the metabolic activity and/or output of the bacteria or their tolerance of the substrate.

In preferred embodiments, recombinant bacteria are used to produce isobutyl isobutyrate. In some embodiments, the bacteria contain polynucleotides encoding an alcohol transferase (ATF) and a KIVDH complex. Exemplary ATF-encoding genes include without limitation *S. cerevisiae* ATF1 (or homologs thereof) or, preferably, *S. cerevisiae* EHT1 (or homologs thereof). In some embodiments, the recombinant bacteria may further contain elevated expression or activity of acetolactate synthase, acetohydroxy acid isomeroreductase, and dihydroxy-acid dehydratase, thereby promoting the biological production of 2-ketoisovalerate. The genes encoding the ATF and the KIVDH components may be part of the same polynucleotide, or separate polynucleotides. They may be regulated by shared or distinct regulatory elements, such as promoters. In some embodiments, the ATF and KIVDH genes may be controlled by an inducible promoter (e.g., the lac operon or a functionally similar element). In an exemplary embodiment, bacteria may be grown in the absence of ATF and KIVDH expression, then induced to express the ATF and KIVDH at the same time a suitable substrate for isobutyl isobutyrate production is added to the culture medium. Alternatively, the ATF and KIVDH may be expressed constitutively. In a preferred embodiment, the substrate for isobutyl isobutyrate production is isobutanol. Other suitable substrates may include without limitation ketoisovalerate.

In other preferred embodiments, recombinant bacteria are used to produce isobutyl acetate. In some embodiments, the bacteria contain polynucleotides encoding an alcohol transferase (ATF) and a KIVDH complex. In other embodiments, the bacteria contain polynucleotides encoding an alcohol transferase (ATF) and a 2-keto-acid decarboxylase (KDC). Exemplary ATF-encoding genes include without limitation *S. cerevisiae* ATF1 (or homologs thereof) or *S. cerevisiae* EHT1 (or homologs thereof). In some embodiments, the recombinant bacteria may further contain elevated expression or activity of acetolactate synthase, acetohydroxy acid isomeroreductase, and dihydroxy-acid dehydratase, thereby promoting the biological production of 2-ketoisovalerate. The bacteria may also contain mutations reducing endogenous alcohol dehydrogenase (ALD) and/or isobutyraldehyde reductase (IBR) activities, thereby enhancing the levels of available isobutyraldehyde. The genes encoding the ATF and the KIVDH or the KDC may be part of the same polynucleotide, or separate polynucleotides. They may also be regulated by shared or distinct regulatory elements, such as promoters. They may be controlled by inducible or constitutive promoter(s). In some embodiments, the substrate used to generate isobutyl acetate is a reduced carbon source, for example a sugar (preferably, glucose). In other embodiments, isobutanol and/or ketoisovalerate may be added as the substrate for isobutyl acetate production.

In some embodiments, the methods of the present disclosure may include a step of substantially purifying the ester produced by the recombinant bacteria. In some embodiments, an ester is evaporated using any gas stripping method known in the art, for example by using a Graham condenser. Since esters are relatively volatile, a gas (e.g., oxygen) may be bubbled through the culture medium containing the recombinant bacteria, and an ester may be collected as it evaporates. Suitable gas stripping methods need not include a heating step. In other embodiments, an ester is collected from the culture medium containing the recombinant bacteria by siphoning. This procedure takes advantage of the relatively low aqueous solubility of esters. When an ester is produced by the recombinant bacteria in the culture medium (particularly at concentrations higher than its limit of aqueous solubility), it may form a bilayer on top of the culture medium. Siphoning may be used to purify an ester separating from the culture medium, e.g., in a bilayer. In other embodiments, an ester may be distilled from the culture medium. An ester may also be extracted from the culture medium using a solvent (for example, hexane or ethyl acetate) and distilled from the extract. In some embodiments, a single ester product is purified. In other embodiments, multiple ester products are purified. In preferred embodiments, the ester to be purified is isobutyl isobutyrate or isobutyl acetate.

Esters may be purified at any step in the culturing process. Many methods for product generation and purification from bacterial cultures are known in the art (for example, see Villadsen et al. Bioreaction Engineering Principles. $3^{rd}$ ed. Springer; 2011). Ester purification may be performed continuously during culturing, as in a continuous culture method, or it may be performed separately from or after culturing, as in a batch or fed-batch culture method. For example, gas stripping may be used to purifying esters in situ during production. In another example, siphoning may be used to purify an ester bilayer from the culture medium during production or after production has been stopped.

Supplemental Information

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Oligonucleotide Synthesis (Gait, ed., 1984); Animal Cell Culture (Freshney, ed., 1987); Handbook of Experimental Immunology (Weir & Blackwell, eds.); Gene Transfer Vectors for Mammalian Cells (Miller & Calos, eds., 1987); Current Protocols in Molecular Biology (Ausubel et al., eds., 1987); PCR: The Polymerase Chain Reaction, (Mullis et al., eds., 1994); Current Protocols in Immunology (Coligan et al., eds., 1991); The Immunoassay Handbook (Wild ed., Stockton Press NY, 1994); Bioconjugate Techniques (Hermanson, ed., Academic Press, 1996); and Methods of Immunological Analysis (Masseyeff, Albert, and Staines, eds., Weinheim: VCH Verlags gesellschaft mbH, 1993).

The present disclosure identifies specific polynucleotides/genes useful in the methods, compositions and organisms of the disclosure. However, it should be recognized that absolute identity to such genes is not necessary, as substantially similar polynucleotides/genes that perform substantially similar functions can also be used in the compositions and methods of the present disclosure. For example, changes in a particular gene or polynucleotide containing a sequence encoding a polypeptide or enzyme can be made and screened for expression and/or activity. Typically such changes include conservative and/or silent mutations.

Due to the inherent degeneracy of the genetic code, polynucleotides which encode substantially the same or functionally equivalent polypeptides can also be used to clone and express the same polypeptides (e.g., enzymes). As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of $E.\ coli$, a process sometimes called "codon optimization" (See, e.g., Murray et al., Nucl Acids Res, 17:477-508, 1989).

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Homologs can be identified by reference to various databases and identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. Thus, the term "homologous proteins" is defined to mean that the two proteins have similar amino acid sequences.

As used herein, two proteins (or a region of the proteins) are substantially homologous when the amino acid sequences have at least about 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, typically at least 75%, and even more typically at least 80%, 85%, 90%, 95% or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted using known algorithms (e.g., by the local homology algorithm of Smith and Waterman, Adv Appl Math, 2:482, 1981; by the homology alignment algorithm of Needleman and Wunsch, J Mol Biol, 48:443, 1970; by the search for similarity method of Pearson and Lipman, Proc Natl Acad Sci USA, 85:2444, 1988; by computerized implementations of these algorithms FASTDB (Intelligenetics), BLAST (National Center for Biomedical Information), GAP, BESTFIT, FASTA, and TFASTA in the Wisconsin Genetics Software Package (Genetics Computer Group, Madison, Wis.), or by manual alignment and visual inspection.

A preferred example of an algorithm that is suitable for determining percent sequence identity and sequence similarity is the FASTA algorithm (Pearson and Lipman, Proc Natl Acad Sci USA, 85:2444, 1988; and Pearson, Methods Enzymol, 266:227-258, 1996). Preferred parameters used in a FASTA alignment of DNA sequences to calculate percent identity are optimized, BL50 Matrix 15:−5, k-tuple=2; joining penalty=40, optimization=28; gap penalty-12, gap length penalty=−2; and width=16.

Another preferred example of algorithms suitable for determining percent sequence identity and sequence similarity are the BLAST and BLAST 2.0 algorithms (Altschul et al., Nuc Acids Res, 25:3389-3402, 1977; and Altschul et al., J Mol Biol, 215:403-410, 1990, respectively). BLAST and BLAST 2.0 are used, with the parameters described herein, to determine percent sequence identity for the nucleic acids and proteins of the disclosure. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (Henikoff and Henikoff, Proc Natl Acad Sci USA, 89:10915, 1989) alignments (B) of 50, expectation (E) of 10, M=5, N=−4, and a comparison of both strands.

The BLAST algorithm also performs a statistical analysis of the similarity between two sequences (See, e.g., Karlin and Altschul, Proc Natl Acad Sci USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method (Feng and Doolittle, J Mol Evol, 35:351-360, 1987), employing a method similar to a published method (Higgins and Sharp, CABIOS 5:151-153, 1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc Acids Res, 12:387-395, 1984).

Another preferred example of an algorithm that is suitable for multiple DNA and amino acid sequence alignments is the CLUSTALW program (Thompson et al., Nucl Acids. Res, 22:4673-4680, 1994). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, Proc Natl Acad Sci USA, 89:10915-10919, 1992).

Polynucleotides of the disclosure further include polynucleotides that encode conservatively modified variants of the polypeptides of Tables I and II. "Conservatively modified variants" as used herein include individual mutations that result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1. Alanine (A), Glycine (G); 2. Aspartic acid (D), Glutamic acid (E); 3. Asparagine (N), Glutamine (Q); 4. Arginine (R), Lysine (K); 5. Isoleucine (I), Leucine (L), Methionine (M), Valine (V); 6. Phenylalanine (F), Tyrosine (Y), Tryptophan (W); 7. Serine (S), Threonine (T); and 8. Cysteine (C), Methionine (M).

The terms "derived from" or "of" when used in reference to a nucleic acid or protein indicates that its sequence is identical or substantially identical to that of an organism of interest. For instance, "a KDC derived from *L. lactis*" or "a 2-keto acid decarboxylase of *L. lactis*" refers to a 2-keto acid decarboxylase enzyme having a sequence identical or substantially identical to a native 2-keto acid decarboxylase enzyme of *L. lactis*. The terms "derived from" and "of" when used in reference to a nucleic acid or protein do not indicate that the nucleic acid or protein in question was necessarily directly purified, isolated or otherwise obtained from an organism of interest. Thus by way of example, an isolated nucleic acid containing a KDC coding region of *L. lactis* need not be obtained directly from this species, instead the isolated nucleic acid may be prepared synthetically using methods known to one of skill in the art.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction. As used herein, the term "transformed" refers to a cell that has an exogenous polynucleotide sequence integrated into its genome or as an episomal plasmid that is maintained for at least two generations.

The terms "coding region," "open reading frame" and "ORF" refers to a sequence of codons extending from an initiator codon (ATG) to a terminator codon (TAG, TAA or TGA), which can be translated into a polypeptide.

In some embodiments of the disclosure, the coding sequences of the polynucleotides are operably linked to a promoter. In some embodiments, the promoter is an inducible promoter. In some embodiments, the promoter is a constitutive promoter. As used herein, "inducible promoter" refers to a promoter that drives expression of a polynucleotide to which it is operably linked upon cellular perception of a stimulus. Likewise, inducible promoters can terminate expression of a polynucleotide to which it is operably linked upon removal of a stimulus. An example of an inducible promoter in the present disclosure is the isopropyl-β-D-thiogalactoside (IPTG) inducible promoter, in which this promoter drives expression of a polynucleotide to which it is operably linked upon perception of IPTG, an exogenous chemical. Constitutive promoters are those promoters that are substantially insensitive to regulation by external stimuli and promote expression of a given polynucleotide in an essentially constant manner.

As used herein, "recombinant" or "heterologous" or "heterologous polynucleotide" or "recombinant polynucleotide" refers to a polynucleotide wherein the exact nucleotide sequence of the polynucleotide is foreign to (i.e., not naturally found in) a given host. These terms may also refer to a polynucleotide sequence that may be naturally found in a given host, but in an unnatural (e.g., greater than or less than expected) amount, or additionally if the sequence of a polynucleotide comprises two or more subsequences that are not found in the same relationship to each other in nature. For example, regarding the latter, a recombinant polynucleotide could have two or more sequences from unrelated polynucleotides or from homologous nucleotides arranged to make a new polynucleotide. Specifically, the present disclosure describes the introduction of a recombinant vector into a microorganism, wherein the vector contains a polynucleotide coding for a polypeptide that is not normally found in the microorganism or contains a foreign polynucleotide coding for a substantially homologous polypeptide that is normally found in the host organism. With reference to the host cell's genome, then, the polynucleotide sequence that encodes the polypeptide is recombinant or heterologous. "Recombinant" may also be used to refer to an organism that contains one or more heterologous polynucleotides.

As used herein, the term "vector" refers to a polynucleotide construct designed to introduce nucleic acids into one or more cell types. Vectors include cloning vectors, expression vectors, shuttle vectors, plasmids, cassettes and the like. As used herein, the term "plasmid" refers to a circular double-stranded DNA construct used as a cloning and/or expression vector. Some plasmids take the form of an extrachromosomal self-replicating genetic element (episomal plasmid) when introduced into a host cell. Other plasmids integrates into a host chromosome (integrative plasmid) when introduced into a host cell, and are thereby replicated along with the host cell genome. Moreover, certain vectors are capable of directing the expression of coding regions to which they are operatively linked. Such vectors are referred to herein as "expression vectors." Thus expression vectors cause cells to express polynucleotides and/or polypeptides other than those native to the cells, or in a manner not native to the cells).

Genetic modifications that result in an increase in gene expression or function can be referred to as amplification, overproduction, overexpression, activation, enhancement, addition, or up-regulation of a gene. More specifically, reference to increasing the action (or activity) of enzymes or other proteins discussed herein generally refers to any genetic modification of the host cell in question which results in increased expression and/or functionality (biological activity) of the enzymes or proteins and includes higher activity or action of the proteins (e.g., specific activity or in vivo enzymatic activity), reduced inhibition or degradation of the proteins, and overexpression of the proteins. For example, gene copy number can be increased, expression levels can be increased by use of a promoter that gives higher levels of expression than that of the native promoter, or a gene can be altered by genetic engineering or classical mutagenesis to increase the biological activity of an enzyme or action of a protein. Combinations of some of these modifications are also possible.

Genetic modifications which result in a decrease in gene expression, in the function of the gene, or in the function of the gene product (i.e., the protein encoded by the gene) can be referred to as inactivation (complete or partial), deletion, interruption, blockage, silencing, or down-regulation, or attenuation of expression of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). The term "functional deletion" as used herein refers to a genetic modification of a gene that serves to substantially eliminate transcription, translation or activity of any resulting gene product. More specifically, reference to decreasing the action of proteins discussed herein generally refers to any genetic modification in the host cell in question, which results in decreased expression and/or functionality (biological activity) of the proteins and includes decreased activity of the proteins (e.g., decreased enzymatic activity), increased inhibition or degradation of the proteins as well as a reduction or elimination of expression of the proteins. Combinations of some of these modifications are also possible.

The terms "decrease," "reduce" and "reduction" as used in reference to biological function (e.g., enzymatic activity, production of compound, expression of a protein, etc.) refer to a measurable lessening in the function by preferably at least 10%, more preferably at least 50%, still more preferably at least 75%, and most preferably at least 90%. Depending upon the function, the reduction may be from 10% to 100%. The term "substantial reduction" and the like refers to a reduction of at least 50%, 75%, 90%, 95% or 100%.

The terms "increase," "elevate" and "elevation" as used in reference to biological function (e.g., enzymatic activity, production of compound, expression of a protein, etc.) refer to a measurable augmentation in the function by preferably at least 10%, more preferably at least 50%, still more preferably at least 75%, and most preferably at least 90%. Depending upon the function, the elevation may be from 10% to 100%; or at least 10-fold, 100-fold, or 1000-fold up to 100-fold, 1000-fold or 10,000-fold or more. The term "substantial elevation" and the like refers to an elevation of at least 50%, 75%, 90%, 95% or 100%.

The terms "isolated" and "purified" as used herein refers to a material that is removed from at least one component with which it is naturally associated (e.g., removed from its original environment). The term "isolated," when used in reference to a biosynthetically-produced ester, refers to an ester that has been removed from the culture medium of the bacteria that produced the ester. As such an isolated ester is free of extraneous or unwanted compounds (e.g., substrate molecules, bacterial components, etc.).

As used herein, the singular form "a", "an", and "the" includes plural references unless indicated otherwise. For example, "an" ALD includes one or more ALDs.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting" and/or "consisting essentially of" aspects and embodiments.

EXAMPLES

To better facilitate an understanding of embodiments of the disclosure, the following examples are presented. The following examples are merely illustrative and are not meant to limit any embodiments of the present disclosure in any way.

Abbreviations: ADH (alcohol dehydrogenase); AHIR (acetohydroxy acid isomerase); ADH (alcohol dehydrogenase); ALDH (aldehyde dehydrogenase); ALS (acetolactate synthase); ATF (alcohol transferase); DHAD (dihydroxy acid dehydratase); IBR (isobutyraldehyde reductase); and KDC (2-keto-acid decarboxylase).

Materials and Methods

Reagents and Bacterial Strains

All enzymes were purchased from New England Biolabs. All synthetic oligonucleotides were ordered from Integrated DNA Technologies. DNA sequencing services were done by Davis Sequencing. All chemicals for gas chromatography (GC) standards except for ethanol (VWR) and tetradecyl acetate (Ark Pharm, Inc.) were purchased from Sigma Aldrich. 2-Keto acids (pyruvate (≥99%), 2-ketobutyrate (≥95%), 2-ketovalerate (≥98%), 2-ketoisovalerate (≥95%), 2-keto-3-methylvalerate (≥98%), 2-keto-4-methylvalerate (≥98%), phenylpyruvate (≥98%)) were purchased from Sigma Aldrich.

Restriction enzymes and antarctic phosphatase were from New England Biolabs (Ipswich, Mass., USA). Rapid DNA ligation kit was from Roche (Mannheim, Germany). KOD DNA polymerase was from EMD Chemicals (San Diego, Calif.). Oligonucleotides were from Integrated DNA Technologies (San Diego, Calif.).

TABLE 1

E. coli Strains and Plasmids

| Strain/ Plasmid | Description |
|---|---|
| BW25113 | rrnBT14 ΔlacZWJ16 hsdR514 ΔaraBAD$_{AH33}$ ΔrhaBAD$_{LC78}$ |
| JCL16 | BW25113 F'[traD36 proAB$^+$ lacI$^q$ZΔM15 Tn10(tet$^r$)] |
| JCL88 | Same as JCL16 but with ΔadhE Δfrd ΔldhA Δpta Δfnr |
| JCL260 | Same as JCL16 but ΔadhE Δfrd-ldhA Δpta ΔpflB Δfnr |
| AL80 | Same as JCL260 but ΔyqhD |
| AL275 | AL80 with plasmids pSA69 and pSA129 |
| AL287 | Same as JCL260 but ΔyqhD ΔadhP |
| AL288 | Same as JCL260 but ΔyqhD ΔeutG |
| AL289 | Same as JCL260 but ΔyqhD ΔyiaY |
| AL290 | Same as JCL260 but ΔyqhD ΔyjgB |
| AL293 | AL287 with plasmids pGR03 and pSA129 |
| AL294 | AL288 with plasmids pGR03 and pSA129 |
| AL295 | AL289 with plasmids pGR03 and pSA129 |
| AL296 | AL290 with plasmids pGR03 and pSA129 |
| AL312 | Same as JCL260 but ΔyqhD ΔadhP ΔeutG |
| AL313 | AL312 with plasmids pGR03 and pSA129 |
| AL322 | Same as JCL260 but ΔyqhD ΔadhP ΔeutG ΔyiaY |
| AL328 | AL322 with plasmids pGR03 and pSA129 |
| AL331 | Same as JCL260 but ΔyqhD ΔadhP ΔeutG ΔyiaY ΔyjgB |
| AL332 | AL331 with plasmids pGR03 and pSA129 |
| AL345 | JCL260 with plasmids pGR03 and pSA129 |
| AL555 | Same as JCL260 but ΔyqhD ΔbetA |
| AL556 | Same as JCL260 but ΔyqhD ΔadhP ΔeutG ΔyiaY ΔyjgB ΔbetA |
| AL615 | Same as JCL260 but ΔyqhD ΔfucO |
| AL616 | Same as JCL260 but ΔyqhD ΔeutE |
| AL626 | Same as AL704 with tetracycline and kanamycin resistance = Same as JCL260 but ΔyqhD ΔadhP ΔeutG ΔyiaY ΔyjgB ΔbetA ΔfucO |
| AL627 | AL626 with plasmids pGR03 and pSA129 |
| AL704 | Same as AL626 with tetracycline resistance but not kanamycin resistance ~JCL260 but ΔyqhD ΔadhP ΔeutG ΔyiaY ΔyjgB ΔbetA ΔfucO |
| AL707 | Same as JCL260 but ΔyqhD ΔadhP ΔeutG ΔyiaY ΔyjgB ΔbetA ΔfucO ΔeutE |
| AL1050 | F- lambda- ilvG- rfb-50 rph-1 lacI$^q$ tetR spec$^R$ |
| AL2045 | Same as JCL260 but with ΔaceEF |
| AL1448 | Same as AL626 but ΔeutE ΔyahK ΔybbO ΔgldA ΔdkgA ΔyghA |
| pSA40 | p15A ori; Kan$^R$; P$_L$lacO$_1$: |
| pSA69 | p15A ori; Kan$^R$; P$_L$lacO$_1$: alsS-ilvCD |
| pSA129 | ColE1 ori; Amp$^R$; P$_L$lacO$_1$: kivd |
| pSA138 | ColE1 ori; P$_L$lacO$_1$: kivd-yqhD |
| pGR03 | Same as pSA69 but Cm$^R$ |
| pAL217 | ColE1 ori; Amp$^R$; P$_L$lacO$_1$: kivd-adhP |
| pAL218 | ColE1 ori; Amp$^R$; P$_L$lacO$_1$: kivd-eutG |
| pAL219 | ColE1 ori; Amp$^R$; P$_L$lacO$_1$: kivd-yiaY |
| pAL220 | ColE1 ori; Amp$^R$; P$_L$lacO$_1$: kivd-yjgB |
| pAL221 | ColE1 ori; Amp$^R$; P$_L$lacO$_1$: kivd-betA |
| pAL222 | ColE1 ori; Amp$^R$; P$_L$lacO$_1$: kivd-fucO |
| pAL223 | ColE1 ori; Amp$^R$; P$_L$lacO$_1$: kivd-eutE |
| pZE12-luc | ColE1 ori; Amp$^R$; P$_L$lacO$_1$: luc(VF) |
| pAL162 | ColE1 ori; Amp$^R$; P$_L$lacO$_1$: adhP |
| pAL158 | ColE1 ori; Amp$^R$; P$_L$lacO$_1$: eutG |
| pAL157 | ColE1 ori; Amp$^R$; P$_L$lacO$_1$: yiaY |
| pAL156 | ColE1 ori; Amp$^R$; P$_L$lacO$_1$: yjgB |
| pAL213 | ColE1 ori; Amp$^R$; P$_L$lacO$_1$: beta |
| pAL214 | ColE1 ori; Amp$^R$; P$_L$lacO$_1$: fucO |
| pAL215 | ColE1 ori; Amp$^R$; P$_L$lacO$_1$: eutE |
| pAL495 | p15A ori; Cm$^R$; P$_L$lacO$_1$: mrfp |
| pAL497 | p15A ori; Cm$^R$; P$_L$lacO$_1$: luxCDE |
| pAL603 | ColE1 ori; Amp$^R$; P$_L$lacO$_1$: alsS-ilvCD, P$_L$lacO$_1$: kdc-adhA |
| pAL609 | ColE1 ori; Amp$^R$; P$_L$lacO$_1$: kdc-mhpF |
| pAL622 | ColE1 ori; Kan$^R$; ATF1 |

TABLE 1-continued

E. coli Strains and Plasmids

| Strain/Plasmid | Description |
|---|---|
| pAL633 | ColE1 ori; $Amp^R$; $P_LlacO_1$: bkdA1-bkdA2-bkdB-lpdV |
| pAL670 | p15A ori; $Cm^R$; $P_LlacO_1$: EHT1 |
| pAL675 | p15A ori; $Cm^R$; $P_LlacO_1$: EEB1 |
| pAL676 | p15A ori; $Cm^R$; $P_LlacO_1$: ATF1 |
| pAL679 | ColE1 ori; $Amp^R$; $P_LlacO_1$: kdc-ATF1 |
| pAL682 | p15A ori; $Kan^R$; $P_LlacO_1$: mrfp |
| pAL683 | p15A ori; $Kan^R$; $P_LlacO_1$: EEB1 |
| pAL684 | p15A ori; $Kan^R$; $P_LlacO_1$: EHT1 |
| pAL685 | p15A ori; $Kan^R$; $P_LlacO_1$: ATF1 |
| pAL689 | p15A ori; $Kan^R$; $P_LlacO_1$: cat |
| pAL692 | ColE1 ori; $Amp^R$; $P_LlacO_1$: EHT1, $P_LlacO_1$: bkdA1-bkdA2-bkdB-lpdV |
| pAL693 | ColE1 ori; $Amp^R$; $P_LlacO_1$: cat, $P_LlacO_1$: bkdA1-bkdA2-bkdB-lpdV |
| pAL723 | ColE1 ori; $Kan^R$; $P_LlacO_1$: ATF1 |
| pAL953 | Cola ori; $Kan^R$; $P_LlacO_1$: ackA-pta |
| pAL954 | Cola ori; $Kan^R$; $P_LlacO_1$: acs |
| pAL955 | Cola ori; $Kan^R$; $P_LlacO_1$: edgE-aldB |
| pAL956 | Cola ori; $Kan^R$; $P_LlacO_1$: sfGFP |
| pAL895 | p15A ori; $Spec^R$; $P_LlacO_1$: mRFP1 |
| pAL991 | p15A ori; $Spec^R$; $P_LlacO_1$: ATF1 |

Plasmid Construction and Cloning

All plasmids and oligonucleotides are listed in Table 1 and Table 2 (below), respectively. The target gene(s) and vector fragments were amplified with the pairs of primers from the templates listed in Table 3 below. The resulting fragments were combined by sequence and ligation-independent cloning (SLIC) (Machado et al. Metab. Eng. 14:504-11, 2012). Vector PCR product was treated with DpnI for 1 h at 37° C. A 10 μL reaction containing 1×NEB Buffer 2, 100-1000 ng of vector and insert fragments, and 0.75 U of T4 DNA Polymerase (NEB) was incubated at room temperature for 10 min, then placed on ice to stop the reaction. 2.5 μL of the solution was used for transformation of E. coli. Plasmids were verified by colony PCR, by digestion with restriction enzymes, and by sequencing

TABLE 2

Oligonucleotides

| Name | SEQ ID NO: | SEQUENCE |
|---|---|---|
| GR387 | 2 | TCTAGAGGCATCAAATAAAACGAAA |
| GR388 | 3 | GTGACCTTTCTCCTGCATGC |
| GR689 | 4 | GCATGCAGGAGAAAGGTCACATGAGTAAGCGTAAAGTCGCCATTATC |
| GR698 | 5 | TCTAGAGGCATCAAATAAAACGAAAGGC |
| GR699 | 6 | GGTACCTTTCTCCTCTTTAATGAATTCGG |
| GR701 | 7 | TTTTATTTGATGCCTCTAGATCATGCCGCTTCTCCTGCCTT |
| GR720 | 8 | GCATGCAGGAGAAAGGTCACATGAACGAAATCGACGAAAAGAATCAAG |
| GR721 | 9 | TTTTATTTGATGCCTCTAGATTACGGACCCAGCAGCAGTG |
| GR724 | 10 | TTAAAGAGGAGAAAGGTACCATGAACGAGTACGCCCCCCTG |
| GR725 | 11 | TTTTATTTGATGCCTCTAGATCAGATATGCAAGGCGTGGC |
| SD67 | 12 | GAACGCCGTACGCGAGCGGTATCAGCTCACTCAAA |
| SD68 | 13 | GCCTCGTCCTAGGTCTAGGGCGGCGGATTTGTC |
| SD69 | 14 | CGCCGCCCTAGACCTAGGACGAGGCCCTTTCGTCTTCACCTCGAG |
| SD70 | 15 | GAGCTGATACCGCTCGCGTACGGCGTTCACCGACAAACAACAGAT |
| YT018 | 16 | TAAACGCGTGCTAGAGGCATCAAAT |
| YT040 | 17 | CATGGTACCTTTCTCCTCTTTAATGAATTCGGTCA |
| YT087 | 18 | CATTGTACCTTTCTCCTCTTTAATGAATTC |
| YT193 | 19 | CATTAAAGAGGAGAAAGGTACCATGGCTTCCTCCG |
| YT194 | 20 | TTATTTGATGCCTCTAGAGTCATTAAGCACCGGTGGAGT |
| YT253 | 21 | CATTAAAGAGGAGAAAGGTACAATGGAAAAACACTTACCTTTAATAATAAAT |
| YT255 | 22 | ATCGTTTAAACGAACATTTCCTTATTTGTTGGTATTAC |
| YT256 | 23 | TAAGGAAATGTTCGTTTAAACGATGCTGAAG |

TABLE 2-continued

Oligonucleotides

| Name | SEQ ID NO: | SEQUENCE |
| --- | --- | --- |
| YT257 | 24 | ATTTGATGCCTCTAGCACGCGTTTAGTTGCCTCCTTCATTCTTAG |
| YT438 | 25 | CATTAAAGAGGAGAAAGGTACAATGTTTCGCTCGGGTTACTATCCAAC |
| YT439 | 26 | ATTTGATGCCTCTAGCACGCGTTTATAAAACTAACTCATCAAAGCTGCCAAGA |
| YT440 | 27 | CATTAAAGAGGAGAAAGGTACAATGTCAGAAGTTTCCAAATGGCCAG |
| YT441 | 28 | TTTGATGCCTCTAGCACGCGTTTATACGACTAATTCATCAAACTTAGTGAAAAATTCTGC |
| YT442 | 29 | CATTAAAGAGGAGAAAGGTACAATGAACGAAATCGACGAAAGAATCAAG |
| YT443 | 30 | ATTTGATGCCTCTAGCACGCGTTTACGGACCCAGCAGCAGTG |
| YT466 | 31 | TCTCACCAATAAAAAACGCCCGGCGAATTGTGAGCGGATAACAATTGACATT |
| YT467 | 32 | GGATTTGTTCAGAACGCTCGGTTGCCTAGCACGCGTTTATACGACTAATTCATCA |
| YT468 | 33 | GCAACCGAGCGTTCTGAACAAATC |
| YT469 | 34 | CGCCGGGCGTTTTTTATTGGT |
| YT470 | 35 | GAATTCATTAAAGAGGAGAAAGGTACAATGGAGAAAAAATCACTGGATATACCACCG |
| YT471 | 36 | ATTTGATGCCTCTAGCACGCGTTTACGCCCCGCCCTGC |
| YT479 | 37 | GGATTTGTTCAGAACGCTCGGTTGCCTAGCACGCGTTTACGCCCC |

TABLE 3

Plasmid Construction by Sequence and Ligation-Independent Cloning (SLIC)

| | Vector PCR | | | Insert PCR | | | |
| --- | --- | --- | --- | --- | --- | --- | --- |
| Plasmid | Primer 1 | Primer 2 | Template[a] | Primer 1 | Primer 2 | Template | Gene of Interest[f] |
| pAL495 | YT087 | YT018 | pGR03 | YT193 | YT194 | BBa_E1010[b] | mrfp |
| pAL497 | YT087 | YT018 | pGR03 | YT253 YT256 | YT255 YT257 | gDNA V. harveyi[c] | luxCD luxE |
| pAL603 | SD67 | SD68 | pSA138 | SD69 | SD70 | pSA69 | alsS-ilvCD |
| pAL609 | GR387 | GR388 | pSA138 | GR689 | GR701 | gDNA E. coli JCL16 | mhpF |
| pAL633 | GR698 | GR699 | pSA138 | GR724 | GR725 | gDNA P. putida g7 | KDHC operon |
| pAL670 | YT087 | YT018 | pGR03 | YT440 | YT441 | gDNA S. cerevisiae[d] | EHT1 |
| pAL675 | YT087 | YT018 | pGR03 | YT438 | YT439 | gDNA S. cerevisiae[d] | EEB1 |
| pAL676 | YT087 | YT018 | pGR03 | YT442 | YT443 | pAL622 | ATF1[e] |
| pAL679 | GR387 | GR388 | pSA138 | GR720 | GR721 | pAL622 | ATF1[e] |
| pAL682 | YT087 | YT018 | pSA69 | YT193 | YT194 | BBa_E1010[b] | mrfp |
| pAL683 | YT087 | YT018 | pSA69 | YT438 | YT439 | gDNA S. cerevisiae[d] | EEB1 |
| pAL684 | YT087 | YT018 | pSA69 | YT440 | YT441 | gDNA S. cerevisiae[d] | EHT1 |
| pAL685 | YT087 | YT018 | pSA69 | YT442 | YT443 | pAL622 | ATF1[e] |
| pAL689 | YT087 | YT018 | pSA69 | YT470 | YT471 | pGR03 | cat |
| pAL692 | YT468 | YT467 | pAL633 | YT466 | YT467 | pAL684 | EHT1 |
| pAL693 | YT468 | YT467 | pAL633 | YT466 | YT479 | pAL689 | cat |
| pAL723 | YT040 | YT018 | pSA40 | YT442 | YT443 | pAL622 | ATF1[e] |

[a]All plasmids and oligonucleotides are listed in Tables 1 and 2, respectively.
[b]BBa_E1010 sourced from parts.igem.org
[c]Vibrio harveyi BB120 (ATCC BAA-1116D-5)
[d]Saccharomyces cerevisiae BY4741 (ATCC 4040004)
[e]Codon optimized ATF1 was synthesized by GenScript USA Inc. (Piscataway, NJ).
[f]NCBI reference number: mhpF, NP_414885; the KDHC genes (bkdA1-bkdA2-bkdB-lpdV), YP_001266792.1 YP_001266793.1 YP_001266794.1 YP_001266795.1; EHT1, NP_009736.3; EEB1, NP_015230.1; ATF1, NP_015022.3.

Cell Culture

Overnight cultures were grown in 5 mL Luria Broth (LB) (Fisher BioReagents) containing appropriate antibiotics. Antibiotic concentrations were as follows: kanamycin (50 µg/mL) (IBI Scientific), chloramphenicol (40 µg/mL) (Fisher BioReagents), ampicillin 250 (µg/mL) (Fisher BioReagents), tetracycline (20 µg/mL) (Fisher BioReagents). Production was carried out with M9 medium (33.7 mM $Na_2HPO_4$, 22 mM $KH_2PO_4$, 8.55 mM NaCl, 9.35 mM $NH_4Cl$, 1 mM $MgSO_4$, 0.1 mM $CaCl_2$)(BD Bacto), 5 g $L^{-1}$ yeast extract (BD Bacto), 50 g $L^{-1}$ or 10 g $L^{-1}$ glucose (Fisher BioReagents), and 1000-fold dilution of A5 trace metal mix (2.86 g $H_3BO_3$ (Fisher Chemical), 1.81 g $MnCl_2.4H_2O$ (MP Biomedicals), 0.222 g $ZnSO_4.7H_2O$ (Sigma-Aldrich), 0.39 g $Na_2MoO_4.2H_2O$ (Alfa Aesar), 0.079 g $CuSO_4.5H_2O$ (Sigma-Aldrich), 49.4 mg $Co(NO_3)_2.6H_2O$ (Sigma-Aldrich) per liter water). In this work, this media is referred to as M9P. 50 g $L^{-1}$ glucose was used for C2-C10 acetate ester experiments and 10 g $L^{-1}$ glucose was used for tetradecyl acetate, isobutyrate, and butyrate ester experiments. Optical densities (OD) were measured at 600 nm with a Synergy H1 Hybrid Plate Reader (BioTek Instruments, Inc.).

For standard culturing purposes, E. coli was grown in 5-20 mL of LB media containing any required antibiotics at 37° C. with shaking at 250 rpm in a rotary shaker. For production experiments, E. coli was cultured in 20 ml M9 media containing 36 g/L glucose and 5 g/L yeast extract. Cells were induced with 1 mM IPTG at $OD_{600nm}$ 0.4 and allowed to produce for 24 hours at 30° C. in a rotary shaker (250 rpm). 3 g/L isobutanol and 3 g/L ketoisovalerate were added to the culture medium for the isobutyrate ester experiments. Cells were grown at 30° C. instead of 37° C. because the optimal temperature for yeast alcohol transferase activities is about 25-30° C. For kivdh experiments, the P. putida kivdh operon was subcloned under the PLlac01 IPTG-inducible promoter.

Substrate Feeding Experiments

Overnight cultures were inoculated 1% in 5 mL M9P in 15 mL screw-cap culture tubes. Cells were grown to an $OD_{600}$ of ~0.4 at 37° C. in a rotary shaker (250 rpm), followed by adding 1 mM isopropyl-β-D-thio-galactoside (IPTG) (Promega). The cultures were incubated for 1 h after induction at 30° C. Then metabolites of interest were added to the cultures. Production was performed at 30° C. in a rotary shaker (250 rpm) for 24 h. Screw-cap tubes were tightly sealed to prevent evaporation of products. 1.5 mL of culture was taken for analysis every 24 h. The 1.5 mL of the cultures were centrifuged at 17,000×g for 3 min, then 1 mL of the supernatants were transferred to 2 mL GC vials for GC analysis. Excretion of small products such as alcohols and acids by E. coli is well known (see, e.g., Rabinovitch-Deere et al. Chem. Rev. 113:4611-32, 2013; Bornscheuer et al. Nature 485:185-94, 2012; and Atsumi et al. Nature 451:86-9, 2008).

Production of Esters from Glucose

For mixed acetate ester and isobutyl isobutyrate production from glucose, overnight cultures were inoculated 1% in 5 mL M9P in 15 mL screw-cap tubes. Cells were grown to an $OD_{600}$ of ~0.4 at 37° C. on a rotary shaker (250 rpm), followed by adding 1 mM IPTG. The cultures were allowed to produce at 30° C. on a rotary shaker (250 rpm) for 24 h. 1.5 mL of culture was taken for analysis after 24 h.

For the isobutyl acetate and tetradecyl acetate production experiments, overnight cultures were inoculated 1% in 25 mL M9P in 250 mL baffled flasks or screw-cap flasks. Cells were grown to an $OD_{600}$ of ~0.4 at 37° C. on a rotary shaker (250 rpm), followed by adding 1 mM IPTG. Then 20 mL of culture was transferred to a 250 mL screw-cap flask. For hexadecane layer assisted isobutyl acetate production, 20 mL hexadecane (Sigma-Aldrich) was added to each 250 mL screw-cap flasks. The strong agitation at which the flask was shaking caused the hexadecane layer to become an emulsion with micelles of culture, but the majority of the culture layer underneath is discernible. The cultures were allowed to produce at 30° C. on a rotary shaker (250 rpm) for 24-96 h. 1 mL of culture was taken for analysis every 24 h. For hexadecane layer assisted isobutyl acetate production, 1 mL of the hexadecane layer was also taken for analysis every 24 h.

Detection and Purification of Esters

For purification of esters (e.g., isobutyl isobutyrate), esters were evaporated from culture medium using standard gas stripping (heating is not required). Gas stripping was performed during production in situ. Alternatively, for higher titers (about 5-7 g/L or higher), esters form a bilayer and can be siphoned from the top of the culture during (or after) production. Production of various esters was detected using standard gas chromatography/mass spectrometry (GC-MS) techniques.

The 1-1.5 mL of the cultures were centrifuged at 17,000×g for 3 min, then 0.5-1 mL of the supernatants were transferred to 2 mL GC vials for GC analysis. For hexadecane layer assisted isobutyl acetate production, the centrifugation of the hexadecane samples separates the aqueous and hexadecane layer into two clear layers. Then 05-1 mL of the culture fraction and hexadecane fraction were transferred to a 2 mL GC vial for GC-FID analysis. The same volume of ethyl acetate (Sigma-Aldrich) as culture was added into the tubes to extract tetradecyl acetate and isobutyl isobutyrate after production at room temperature. These samples were mixed for 1 min and settled for 30 min on ice. The each sample was centrifuged with 20,000×g for 1 min. Then, 1 mL of supernatant was taken for GC analysis.

Concentrations of all products, except glucose, were analyzed by GC equipped with a flame ionization detector (FID). The GC system is a GC-2010 with an AOC-20 S auto sampler and AOC-20i Auto Injector (Shimadzu). The column used was a DB-Wax capillary column (30 m length, 0.32-mm diameter, 0.50-1 µm film thickness) (Agilent Technologies). GC oven temperature was initially held at 40° C. for 3 min, then increased at a rate of 45° C. min until 235° C. and held for 4 min. Injector temperature was held at 225° C. and FID detector was held at 330° C. Injection volume was 0.5 µL, injected at a 15:1 split ratio. Helium was used as the carrier gas. 1-pentanol was used as an internal standard. In the case of tetradecyl acetate and butyl butyrate, 1-dodecane was used for internal standard. Retention times from samples were compared with external standards. Standard curves were prepared by diluting pure ester or alcohol into water at concentrations of 0.01, 0.1, and 1 g $L^{-1}$. 100 mg $L^{-1}$ of 1-pentanol was added to all samples and external standards as an internal standard.

While GC-FID was used for quantification of all products in the experiments presented in this study, GS-MS was used to verify the products we produced. 1-2.5 mL GC grade hexane was used to extract from 5 mL cell culture. The mixture was mixed for 1 min, then 1.4 mL of the hexane layer was transferred to a 1.5 mL tube. The hexane extract was centrifuged for 3 min at 17,000×g, then 0.5-1 mL was filtered with a 0.45 µm filter into a GC vial. Due to the volatility of ethyl acetate and propyl acetate, pentane (Sigma-Aldrich) was used for extraction instead of hexane. The GC system is a GC-2010 with an AOC-20i S auto sampler and AOC-20i Auto Injector (Shimadzu). The column used was a SHR5XLB column (30 m length, 0.25-mm diameter, 0.25-μm film thickness) (Shimadzu). GC oven temperature was held at 40° C. for 4 min, then increased at a rate of 45° C. per min until 300° C. and held for 3 min. Injector temperature was held at 250° C. Injection volume was 5 μL, injected at a 10:1 split ratio. Hydrogen was used as the carrier gas. The MS is a GCMS-QP2010S (Shimadzu). The ion source temperature was 200° C. and interface temperature at 250° C. Solvent cut time was 2 min for hexane and 1 min for pentane. Detector voltage was −0.1 kV. Start (m/z) was 50 and end (m/z) was 500. Mass spectra and retention times from samples were compared with external standards.

Glucose Analysis by High-Performance Liquid Chromatography (HPLC)

To determine isobutyl acetate yield from glucose, final glucose concentration was done after 96 h by centrifuging the entire culture and hexadecane layer for 10 min at 3,000×g. Then, 1 mL of cell supernatant was used for HPLC-RID analysis to obtain final glucose concentration. Glucose consumption was measured using a 20A HPLC (Shimadzu) equipped with a differential refractive detector (RID) 10A and an Aminex fast acid analysis column (Bio-rad). 5 mM $H_2SO_4$ served as the mobile phase at a flow rate of 0.6 mL/min at 65° C. for 12.5 min. The standard curve for glucose was done by measuring 0.1, 1, and 10 g $L^{-1}$ glucose by HPLC-RID.

KDHC Activity Assay

Cells were grown to an $OD_{600}$ of ~0.4 in 5 mL LB medium at 37° C., followed by adding 1 mM IPTG. Protein expression was performed at 30° C. for 2 h. Then 1.8 mL of cells were centrifuged at 16,000×g for 10 min, resuspended in 300 μL BugBuster Protein Extraction Reagent (Novagen), and incubated at room temperature for 20 min for cell lysis. Then samples were centrifuged for 20 min, 16,000×g, at 2° C. The soluble fractions were transferred to chilled 1.5 mL tubes, and the insoluble fractions were suspended in 200 μL BugBuster forming a slurry and kept on ice. KDHC activities were measured by following the conversion of 2-keto acids to acyl-CoA with $NAD^+$ at 340 nm at 30° C. using a Synergy H1 Hybrid Plate Reader (BioTek Instruments, Inc.). The assay mixture contained 25 mM 2-keto acid (pyruvate, 2-ketovalerate, 2-ketoisovalerate, 2-keto-3-methylvalerate, 2-keto-4-methylvalerate), 50 mM MOPS buffer (pH 7.0), 0.2 mM Tris-CI (pH 7.00), 0.2 mM NADH (Sigma-Aldrich), 0.2 mM CoA (Sigma-Aldrich), and 12.5 mM potassium phosphate buffer (pH 7.5). One unit of activity is defined as the reduction of 1 mol of $NAD^+$ per minute per mg protein. Protein concentrations were measured using 5× Advanced Protein Assay Reagent (Cytoskeleton Inc.). Bovine Serum Albumin (BSA) was used to prepare a standard curve. No activity was observed in the soluble fraction of the cell lysates of either strain. However, the insoluble fraction was resuspended with the lysis buffer and upon testing, substantial activity of KDHC was observed.

Example 1: Engineering Bacteria to Produce Isobutyraldehyde

Wild type *E. coli* and other bacteria cannot produce isobutanol or its precursor isobutyraldehyde because they lack the 2-keto-acid decarboxylase (KDC) that converts 2-ketoisovalerate to isobutyraldehyde. When kivd, a KDC from *L. lactis*, was overexpressed in *E. coli* together with the valine biosynthesis genes, including alsS (*B. subtilis*), ilvC (*E. coli*) and ilvD (*E. coli*), significant amounts of isobutanol were produced. Overexpression of the valine biosynthesis genes was not necessary for isobutanol production but it amplified the endogenous pathway and promoted the efficient conversion of a carbon source to 2-keto-isovalerate. To optimize production of isobutanol, the *E. coli* strain JCL260 was used as the production host. This strain has deletions in fnr, ldhA, frdBC, pflB, pta, all of which are genes involved in byproduct formation. JCL260 also has a deletion in adhE, one of *E. coli*'s six ADH genes. The other five ADH genes are yqhD, adhP, eutG, yiaY, and yjgB. Since these endogenous ADHs together efficiently convert isobutyraldehyde to isobutanol, very little isobutyraldehyde was produced.

The same JCL260 strain described above was further modified for isobutyraldehyde production. Among the five ADH genes, yqhD was known to contribute significantly to the alcohol dehydrogenase/isobutyraldehyde reductase activity in *E. coli* (Atsumi, Appl Microbiol Biotechnol, 85:651-7, 2010). In order to examine the function of the other four ADH genes, JCL260 with ΔyqhD was further modified in a series of multiple deletion mutants, which were tested for the production of isobutyraldehyde. Alcohol dehydrogenase/aldehyde reductase activity in *E. coli* was substantially eliminated and the production ratio of isobutyraldehyde to isobutanol was significantly increased when all six ADH genes were deleted (FIG. 1; see Table 1 for genotype of strain AL626). Together, the data indicate that these six ADH genes contribute to majority of the alcohol dehydrogenase/isobutyraldehyde reductase activity in *E. coli*. The data further indicate that these genes share high degree of redundancy, and multiple deletions or mutations are required to obtain a strain with substantially reduced alcohol dehydrogenase and/or isobutyraldehyde reductase activity.

Example 2: Engineering Bacteria to Produce Esters

Figure 2:
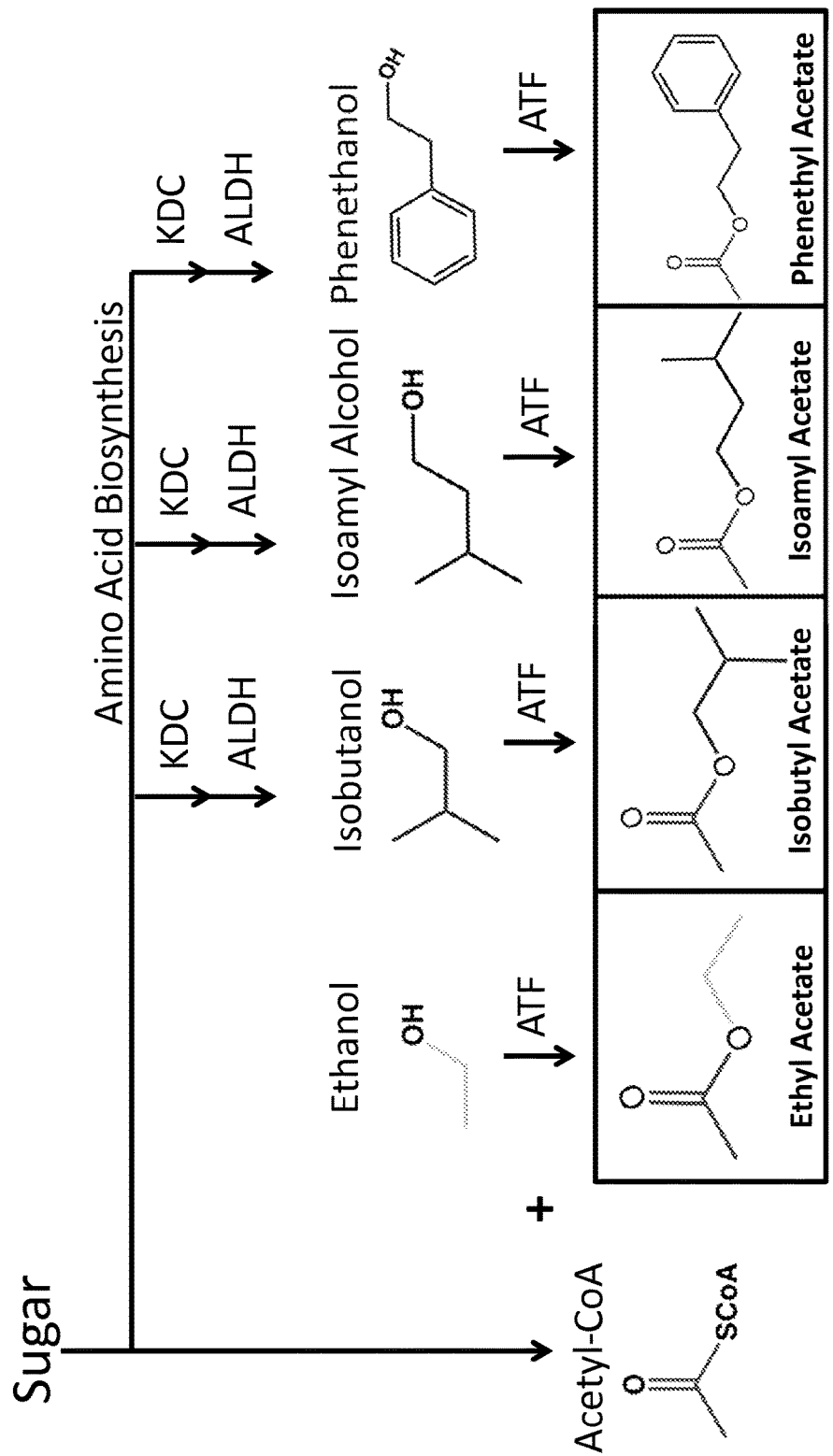
FIG. 2 illustrates the enzymatic production of branched chain alcohols and acetate esters from sugars. Abbreviations: KDC (2-keto-acid decarboxylase); ALDH: (aldehyde dehydrogenase); and ATF (alcohol transferase).
Figure 3A:
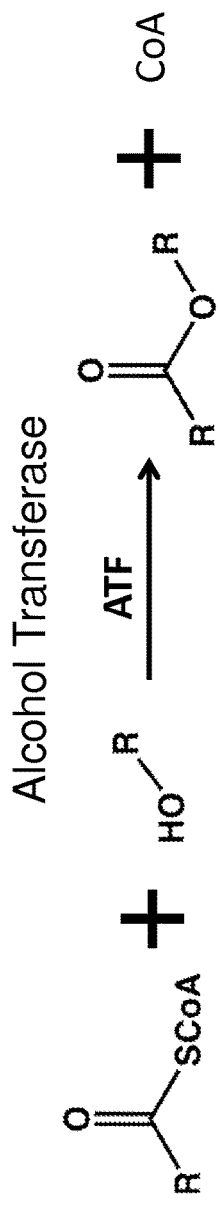
FIG. 3A illustrates the enzymatic production of esters from constituent alcohols.

The previous example demonstrated the construction of bacterial strains that produce high amounts of various alcohols and high amounts of isobutyraldehyde (e.g., AL626). In order to significantly expand the biosynthetic repertoire of these bacteria, further genetic manipulations were undertaken to allow bacteria to produce esters through fermentation (FIG. 2). Expression of an aldehyde dehydrogenase (ALDH) and a 2-keto-acid decarboxylase (KDC) led to the formation of several branched chain alcohols, including isobutanol, isoamyl alcohol, and phenethanol, from compounds derived from amino acid biosynthesis (FIG. 2). ATF1 catalyzes the formation of esters from constituent acid-CoA thioesters and alcohols (FIG. 3A). ATF1 was co-expressed in a bacterial strain along with ALDH and KDC to convert these branched chain alcohols into their corresponding acetate esters (FIG. 2).

Figure 3B:
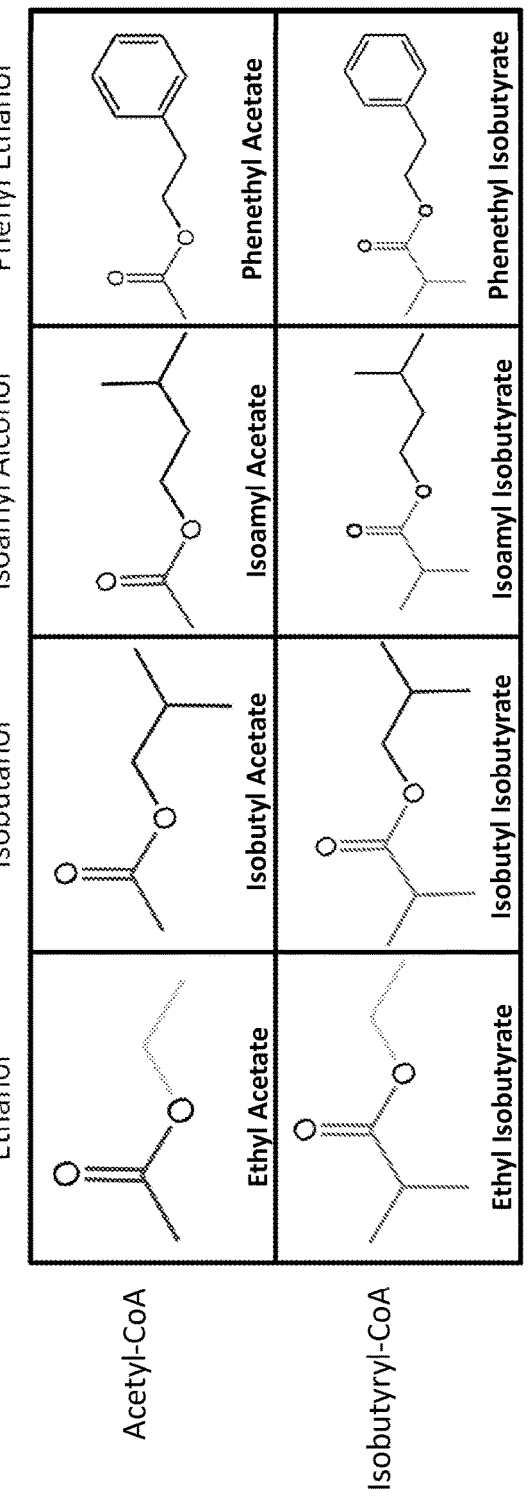
FIG. 3B provides the chemical structures of representative acetate and isobutyrate esters produced by recombinant bacteria.
Figure 4:
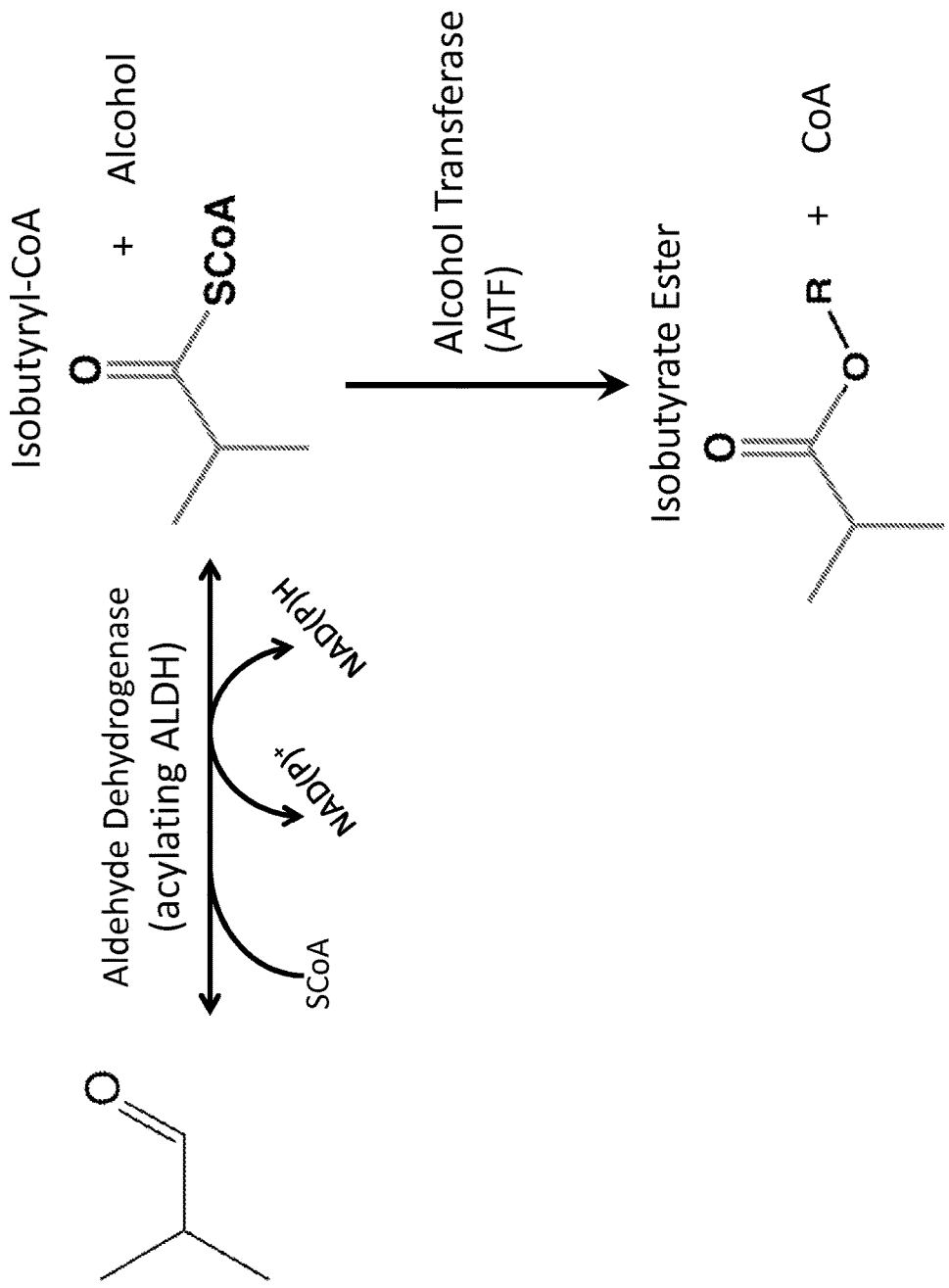
FIG. 4 illustrates the enzymatic production of an isobutyrate ester from isobutyraldehyde.

Aldehyde dehydrogenase activity catalyzes the conversion of an aldehyde into an acid-CoA thioester. When this activity was added to the high isobutyraldehyde-producing bacteria of Example 1 through the expression of the *E. coli* mhpF, these recombinant bacteria were now able to produce isobutyryl-CoA. In this strain, expression of a 2-keto acid decarboxylase (encoded by *L. lactis* kivd), an aldehyde dehydrogenase (encoded by *E. coli* mhpF), and an alcohol transferase (encoded by *S. cerevisiae* ATF1) allowed the production of the several acetate and isobutyrate esters (FIG. 3B). For the first time, these useful esters were produced in significant quantities from a microbial source. FIG. 4 provides a schematic of the enzymatic pathway that led to the production of isobutyrate esters from the high isobutyraldehyde-producing bacterial strain.

Figure 5:
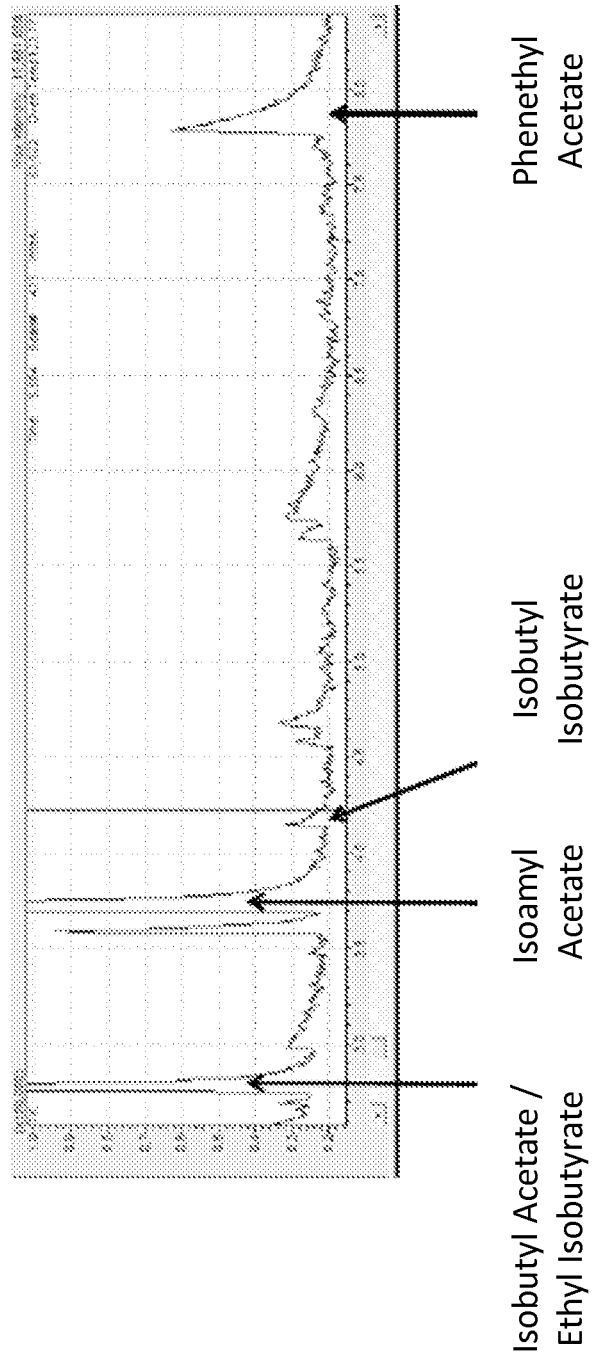
FIG. 5 provides a GC-MS spectrum identifying esters produced by recombinant bacteria.

To further assess recombinant ester production, the culture medium from recombinant bacteria engineered to express KDC, ALDH and ATF1 was analyzed using gas chromatography-mass spectrometry (GC-MS). Significant amounts of isobutyl acetate/ethyl isobutyrate, isoamyl acetate, isobutyl isobutyrate, and phenethyl acetate were detected (FIG. 5). The presence of isobutyl isobutyrate, an important value-added chemical, was further confirmed by analyzing the sample culture medium against isobutyl isobutyrate from a mass spectral reference library. Subtraction analysis indicated high similarity between the sample and library compounds, confirming the production of isobutyl isobutyrate from the recombinant bacteria.

Figure 6:
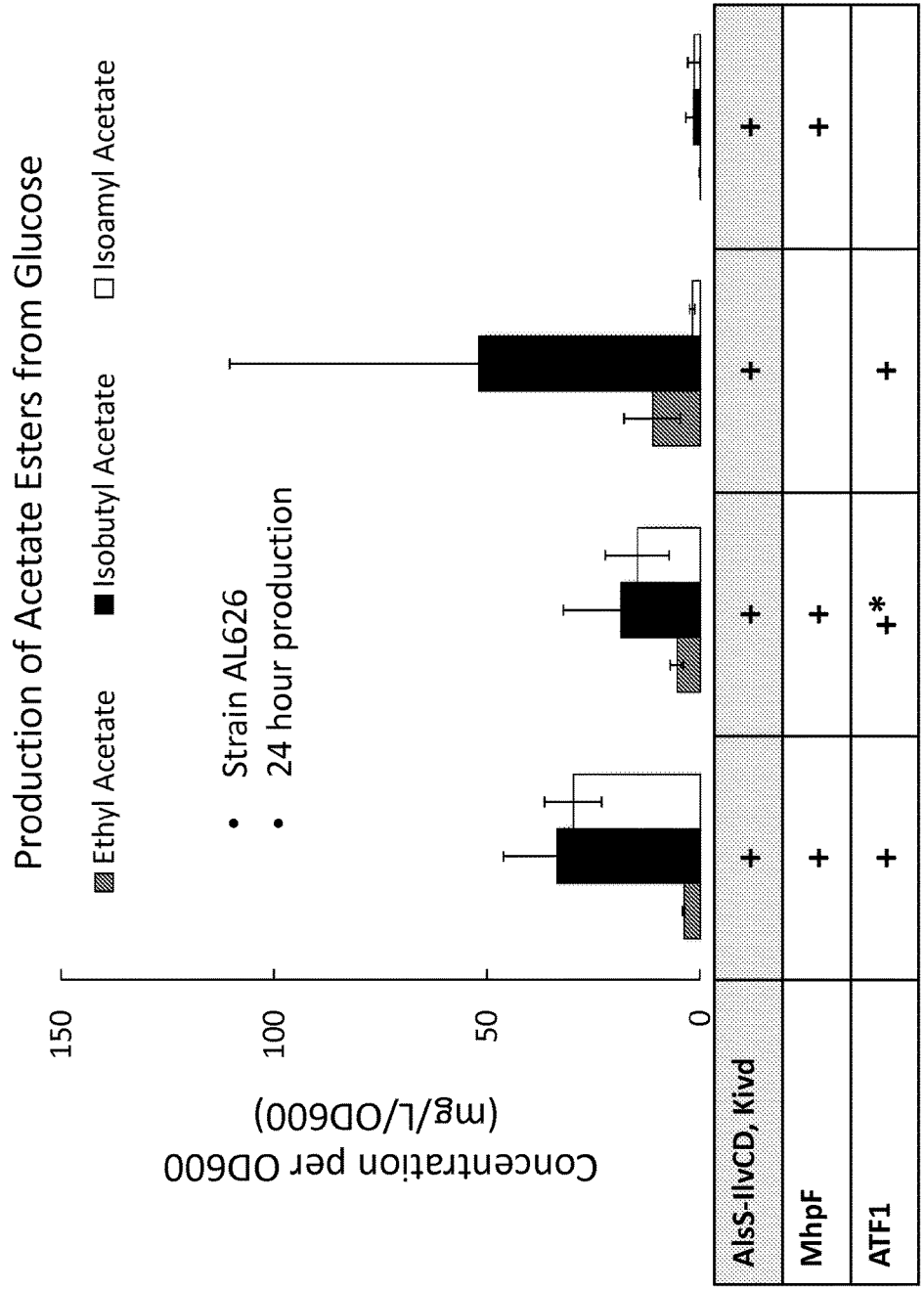
FIG. 6 illustrates the production of acetate esters from glucose by recombinant bacteria engineered to express AlsS-IlvCD and Kivd in the presence of one or both of an acylating aldehyde dehydrogenase (MhpF) and an alcohol transferase (ATF1). The asterisk (*) indicates inclusion of a codon-optimized gene.

As described above, overexpression of Kivd, AlsS, and IlvCD in recombinant bacteria (e.g., AL626) leads to isobutyraldehyde and isobutanol production (FIG. 1). One or both of MhpF and ATF1 were expressed in E. coli strain AL626. In this background, expression of MhpF and ATF1 led to the production of significant titers of several acetate esters, such as ethyl acetate, isobutyl acetate, and isoamyl acetate (FIG. 6). In the absence of MhpF, acetate esters were still produced. In contrast, in the absence of ATF1, acetate ester production was almost completely abolished. These results indicate that ATF1, but not mhpF, is required for acetate ester production in E. coli. This is likely due to the fact that acetate esters are derived from acetyl-CoA, which is already present in substantial quantities in E. coli. A high isobutyraldehyde-producing strain, AL626, was utilized in exemplary embodiments. However, to produce acetate esters, it is not necessary to utilize a high isobutyraldehyde-producing strain (e.g., not necessary to utilize a bacterial strain with substantially reduced alcohol dehydrogenase/isobutyraldehyde reductase activities.

Figure 7:
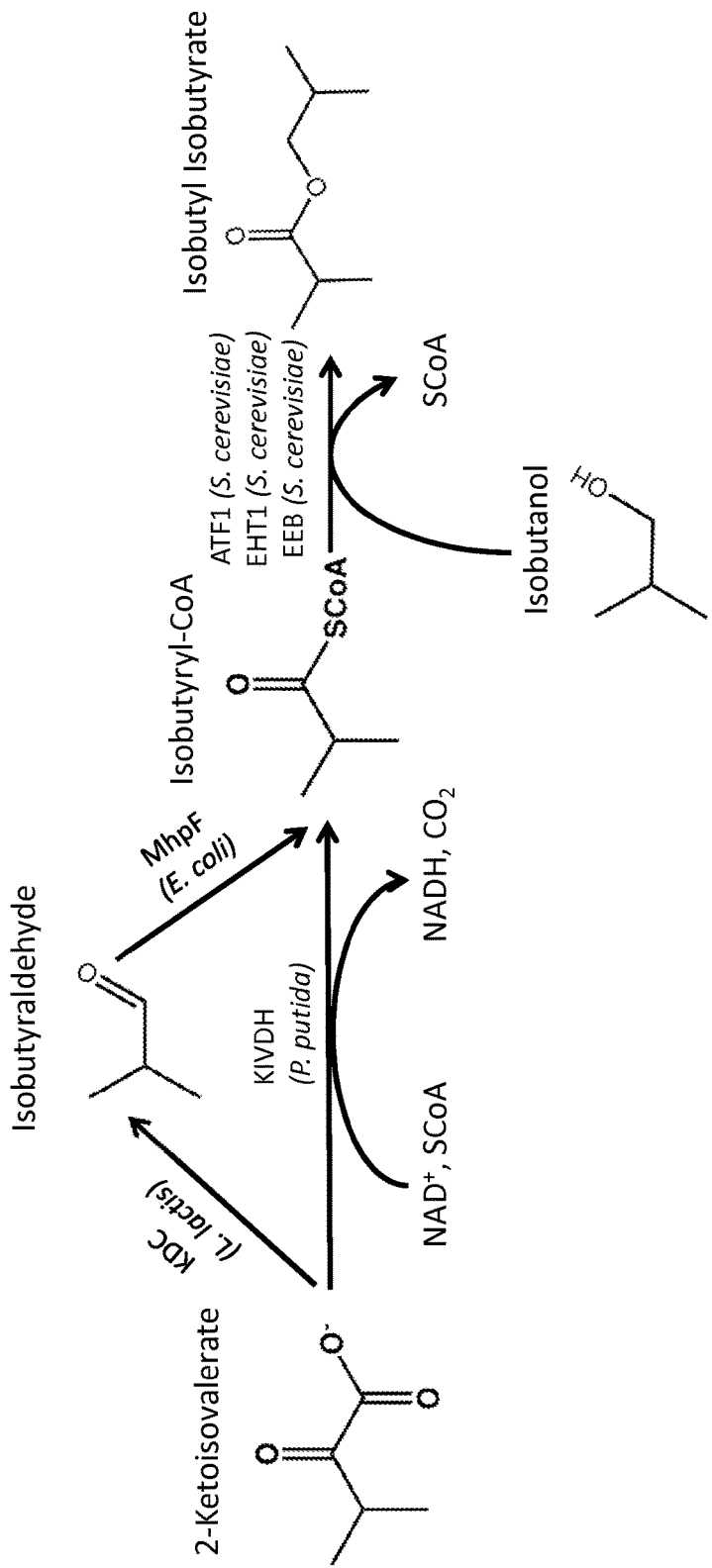
FIG. 7 illustrates two pathways for the production of isobutyryl-CoA and the subsequent production of isobutyl isobutyrate by recombinant bacteria. Exogenous genes of various enzymes are indicated along with their species of origin.

To produce isobutyrate esters, bacteria engineered to produce high levels of isobutyryl-CoA were utilized. As depicted in FIG. 7, two metabolic pathways were used to generate isobutyryl-CoA. In a first pathway, 2-ketoisovalerate was converted to isobutyraldehyde by a KDC (Kivd of L. lactis), and isobutyraldehyde was converted to isobutyryl-CoA by an ALDH (MhpF of E. coli). In a second pathway, the KIVDH complex (P. putida) was used to directly convert 2-ketoisovalerate into isobutyryl-CoA. The KIVDH complex consists of four genes that form a 24-subunit enzyme complex that has high specificity toward 2-ketoisovalerate. The KIVDH operon from P. putida was cloned under the PLlacO1 IPTG-inducible promoter. Once isobutyryl-CoA was formed by either pathway, it was converted to isobutyl isobutyrate by an alcohol transferase (e.g., S. cerevisiae ATF1, EHT1, and/or EEB).

Figure 8:
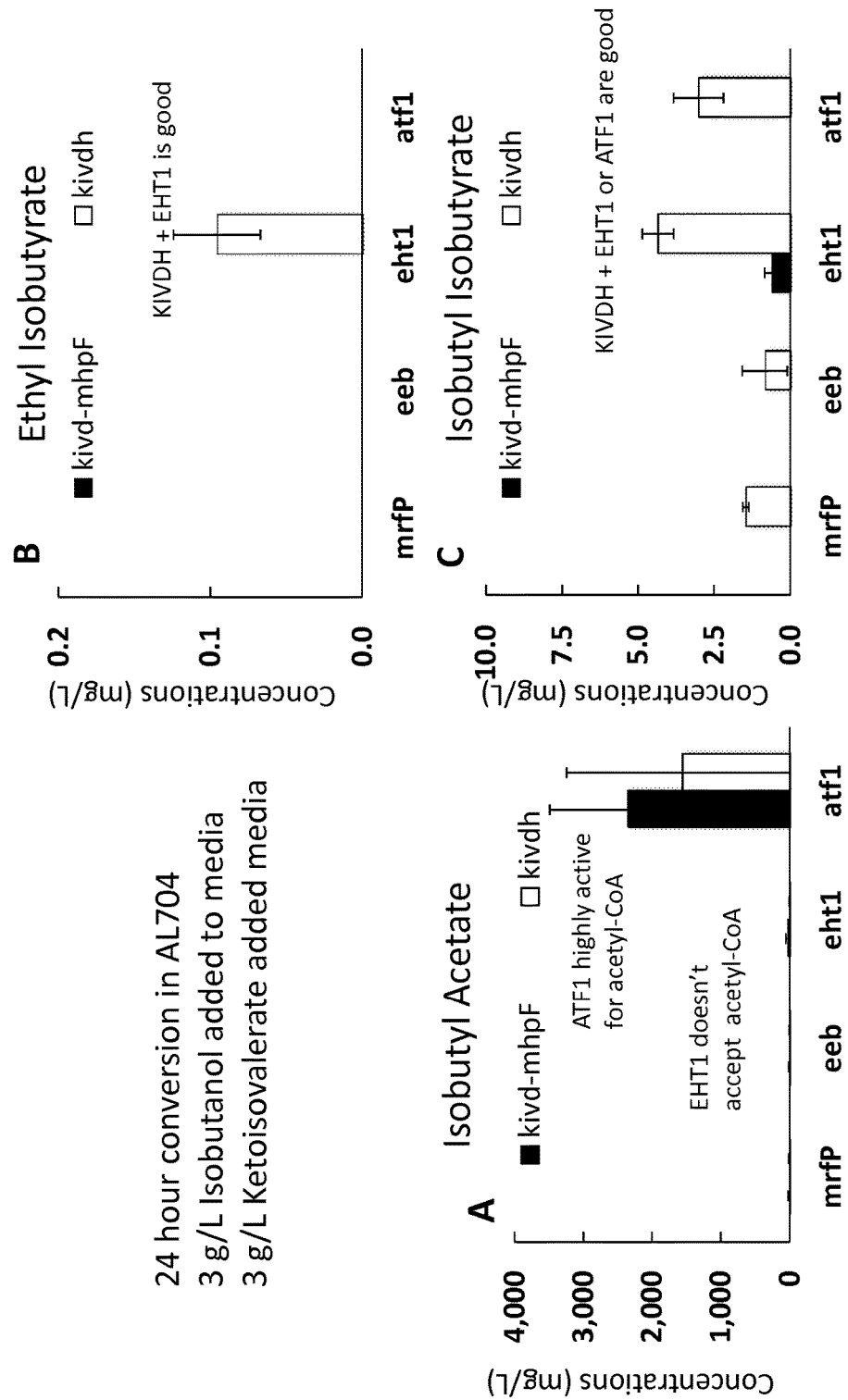
FIG. 8A illustrates that expression of atf1, but not eht1, leads to production of isobutyl acetate in recombinant bacteria equipped with either the kivd-mhpF or the kivdh metabolic pathway for isobutyryl-CoA production.
FIG. 8B illustrates that expression of eht1 leads to production of ethyl isobutyrate in recombinant bacteria equipped with the kivdh metabolic pathway for isobutyryl-CoA production.
FIG. 8C illustrates that expression of eht1 or atf1 leads to production of isobutyl isobutyrate in recombinant bacteria equipped with the kivdh metabolic pathway for isobutyryl-CoA production.

The effect of combinations of isobutyryl-CoA-producing pathways (kivd-mhpF or kivdh) and alcohol transferase genes (ATF1, EHT1, EEB) on the production of isobutyrate esters (isobutyl acetate, ethyl isobutyrate, and isobutyl isobutyrate) was analyzed. Isobutanol and ketoisovalerate (both at 3 g/L) were fed to the bacterial strain AL704 in culture medium, and after 24 hours the amounts of each isobutyrate ester produced were measured. Both the kivd-mhpF and kivdh pathways resulted in the production of isobutyl acetate by bacteria expressing ATF1 (FIG. 8A), but not bacteria expressing MRFP, EEB, or EHT1. Because over 1 g/L of isobutyl acetate was produced by bacteria supplemented with 3 g/L isobutanol, endogenous acetyl-CoA levels were thought to be sufficient to produce significant ester titers without the need for an acetyl-CoA-generating enzyme such as pyruvate formate lyase (e.g., PflB). The kivdh pathway resulted in the production of ethyl isobutyrate by bacteria expressing EHT1 (FIG. 8B). The kivdh pathway also resulted in the production of isobutyl isobutyrate in bacteria expressing any of the three alcohol transferases (FIG. 8C). Production of isobutyl isobutyrate was observed upon expression of EHT1 with the kivd-mhpF pathway.

These results indicated that novel bacterial strains were able to produce significant amounts of several acetate and isobutyrate esters. In general, the kivdh pathway was more effective for ester production than the kivd-mhpF pathway. Expression of ATF1 generated enhanced isobutyl isobutyrate over the negative control (mrfp), but it also led to the production of greater than 1 g/L isobutyl acetate. This indicates that ATF1 has a preference for acetate esters. Expression of EHT1, by contrast, resulted in minimal isobutyl acetate production but significant ethyl isobutyrate and isobutyl isobutyrate production. Thus, EHT1 is considered to be a suitable enzyme for the specific production of isobutyrate esters.

Example 3: Developing Biological Routes to Acetate Esters in Bacteria

Figure 9A:
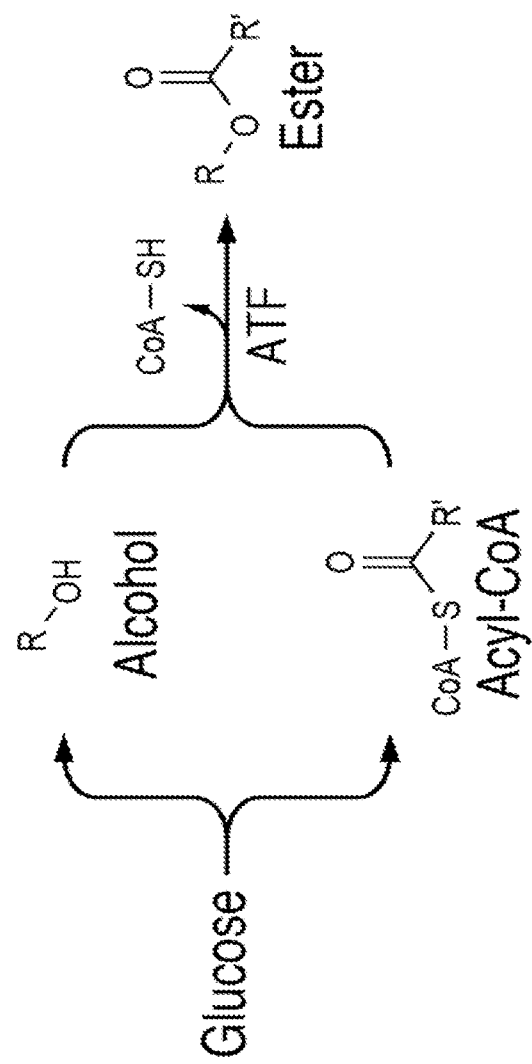
FIG. 9A illustrates a scheme for enzymatic ester synthesis by combining alcohols and acyl-CoA.
Figure 9B:
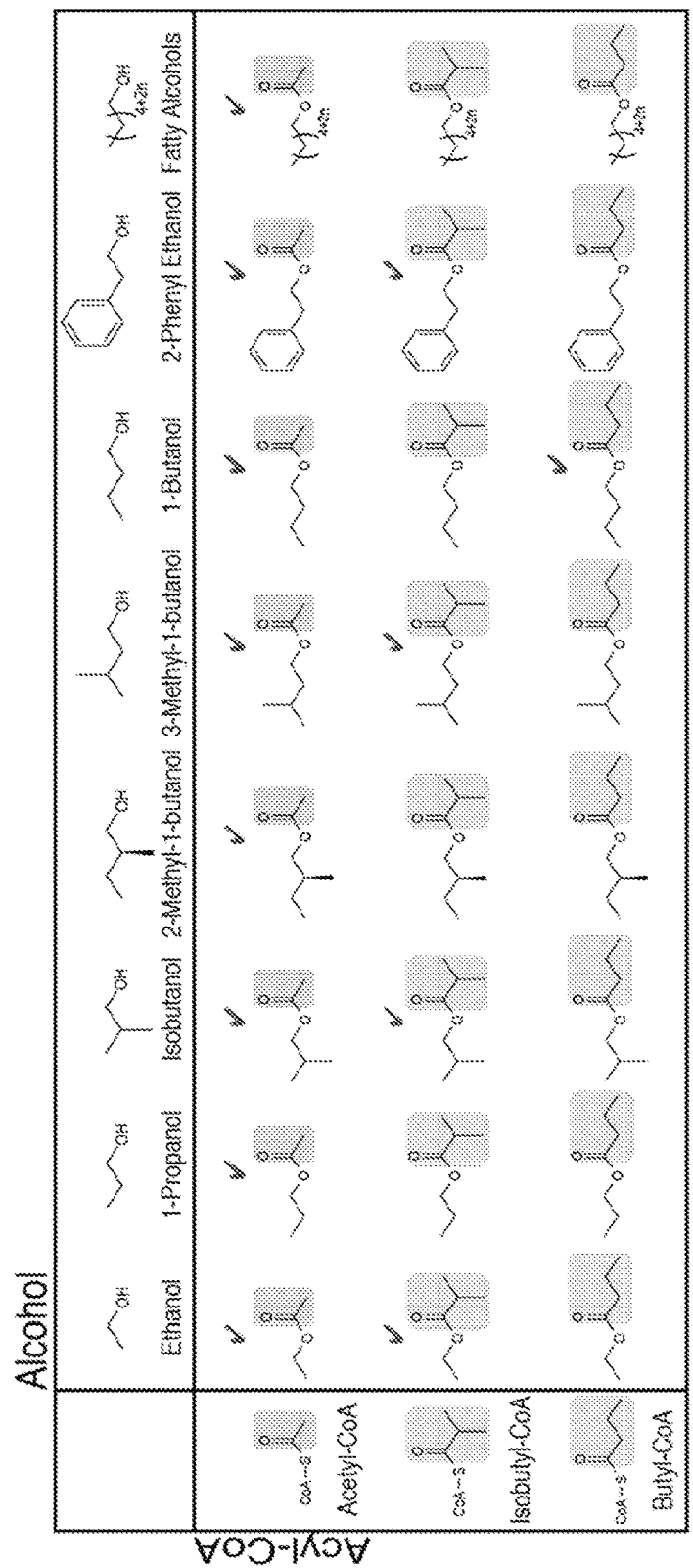
FIG. 9B illustrates a matrix of esters by combinations of alcohols and acyl-CoAs. Red check marks indicate that the corresponding ester was synthesized herein.

As described above in the previous Examples, using acetyl-CoA, a variety of acetate esters can be made in combination with alcohol production pathways. Several alcohols (e.g., ethanol, isopropanol, isobutanol, 1-butanol) have been produced in high yield and titer (see, e.g., Atsumi et al. Nature 451:86-9, 2008; Shen et al. Appl. Environ. Microbiol. 77:2905-15, 2011; Bond-Watts et al. Nat. Chem. Biol. 7:222-7, 2011; and Inokuma et al. J. Biosci. Bioeng. 110:696-701, 2010), in principle allowing for similar yields of esters using a suitable ATF (FIG. 9a-b). Since wild type E. coli is only naturally capable of generating a single alcohol, ethanol, a minimal platform was developed to generate several alcohols as a means to evaluate the potential of acetate ester production. E. coli strain JCL260 (ΔadhE Δfrd ΔldhA Δpta ΔpflB Δfnr) (Atsumi et al. Nature 451:86-9, 2008) was used as a production host, which lacks all major fermentative pathways. This provides increased pyruvate for acetate ester formation.

Figure 10:
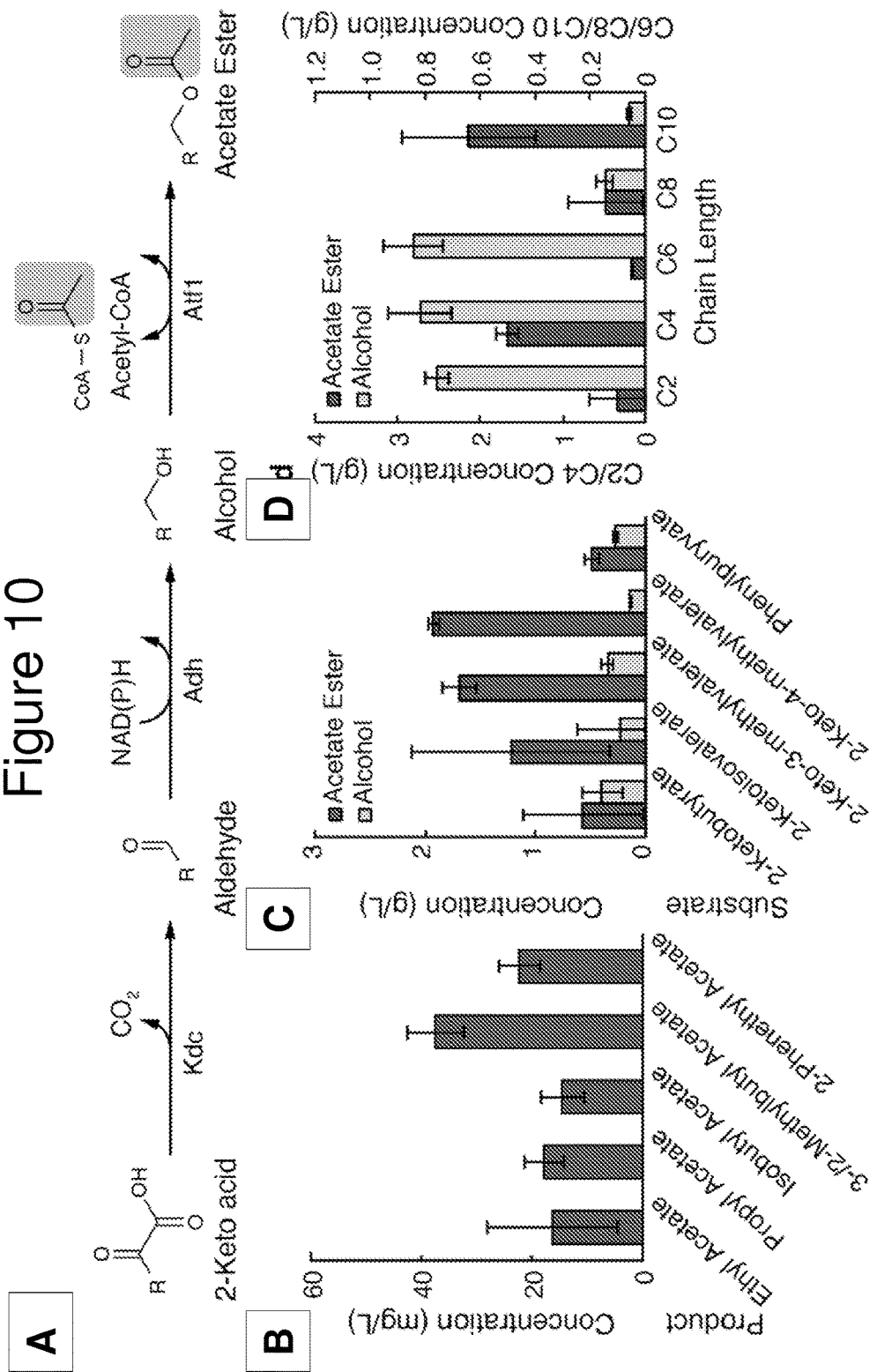
FIG. 10A shows a diagram of acetate ester production from 2-keto acid in bacteria. 2-keto acid is converted to alcohol, then acetate ester is synthesized by combining the alcohol and an acetyl-CoA.
FIG. 10B provides a graph showing in vivo production of a mixture of acetate esters from glucose.
FIG. 10C provides a graph showing in vivo conversion of individually fed 2-keto acids to acetate esters.
FIG. 10D provides a graph showing production of acetate ester by feeding individual straight chain alcohols (C2-C10). In all graphs, strains were induced at $OD_{600}$~0.4 with 1 mM IPTG. Error bars are SD (n=3).

Next, to generate a pool of alcohols, the well-established 2-keto acid based alcohol biosynthesis was utilized (Atsumi et al. Nature 451:86-9, 2008). A promiscuous keto acid decarboxylase (Kdc) can be employed to generate the corresponding aldehydes (FIG. 10a). These aldehydes are subsequently converted to alcohols by endogenous NAD(P)H-dependent aldehyde reductases/alcohol dehydrogenases (Adh)(Rodriguez and Atsumi, Microb Cell Fact, 11:90, 2012). Thus, kdc from Lactococcus lactis (de la Plaza et al. FEMS Microbiol. Lett. 238:267-74, 2004) was expressed in E. coli to convert pyruvate, 2-ketobutyrate, 2-ketoisovalerate, 2-keto-3-methylvalerate, 2-keto-4-methylvalerate, and phenylpyruvate into ethanol, 1-propanol, isobutanol, 2-methyl-1-butanol, 3-methyl-1-butanol, and 2-phenylethanol, respectively.

The kdc gene and a codon optimized ATF1 (S. cerevisiae), the minimal set of genes necessary to produce acetate esters in E. coli, was introduced into JCL260. This strain was incubated for 24 h in M9 minimal media containing 50 g $L^{-1}$ glucose and 5 g $L^{-1}$ yeast extract (hereby referred to as M9P). This strain produced all of the expected esters: ethyl acetate, propyl acetate, isobutyl acetate, 2-methyl-butyl acetate, 3-methyl-butyl acetate, and 2-phenylethyl acetate (FIG. 10b). Roughly 15-20 mg $L^{-1}$ of each ester was detected, totaling ~100 mg $L^{-1}$. This demonstrated that Atf1 was active in E. coli and had broad substrate specificity for alcohols. No esters were detected from a strain lacking Kdc, confirming that both genes are required for ester formation.

The sequence of the codon optimized ATF1 is set forth as SEQ ID NO: 1:

```
ATGAACGAAA TCGACGAAAA GAATCAAGCC CCGGTCCAAC
AAGAATGCCT GAAAGAAATG ATCCAGAATG GTCACGCCCG
CCGTATGGGC TCAGTGGAAG ACCTGTATGT TGCACTGAAC
CGTCAGAATC TGTACCGCAA TTTTTGCACC TATGGTGAAC
TGTCGGACTA CTGTACGCGT GATCAACTGA CCCTGGCTCT
GCGCGAAATC TGCCTGAAAA ACCCGACGCT GCTGCATATT
GTGCTGCCGA CCCGTTGGCC GAACCACGAA AACTACTACC
GTAGCTCTGA ATACTACAGT CGCCCGCATC CGGTTCACGA
TTATATTAGT GTCCTGCAAG AACTGAAACT GTCCGGCGTG
GTTCTGAATG AACAGCCGGA ATACAGCGCG GTTATGAAGC
AAATCCTGGA AGAATTTAAA AACAGCAAGG GTTCTTACAC
GGCCAAAATC TTTAAGCTGA CCACGACCCT GACGATTCCG
TACTTCGGTC CGACCGGTCC GAGCTGGCGC CTGATCTGCC
TGCCGGAAGA ACATACCGAA AAGTGGAAGA AGTTCATCTT
CGTGTCAAAC CACTGTATGT CGGATGGCCG TAGTTCCATC
CATTTCTTTC ACGACCTGCG CGATGAACTG AACAATATCA
AGACCCCGCC GAAAAAGCTG GACTACATCT TCAAGTACGA
AGAAGATTAC CAGCTGCTGC GTAAGCTGCC GGAACCGATT
GAAAAGTGA TCGATTTTCG TCCGCCGTAC CTGTTTATCC
CGAAAAGTCT GCTGTCCGGC TTTATTTACA ATCATCTGCG
TTTCTCATCG AAGGGTGTGT GCATGCGCAT GGATGACGTT
GAAAAAACGG ATGACGTCGT GACCGAAATT ATCAACATTA
GCCCGACCGA ATTTCAGGCG ATCAAGGCCA ACATCAAGTC
TAACATCCAA GGCAAATGCA CGATCACCCC GTTTCTGCAT
GTCTGTTGGT TCGTGAGCCT GCACAAATGG GGCAAGTTTT
TCAAACCGCT GAACTTTGAA TGGCTGACGG ACATTTTCAT
CCCGGCGGAT TGTCGTTCTC AGCTGCCGGA TGACGATGAA
ATGCGTCAAA TGTATCGCTA CGGCGCCAAT GTGGGTTTTA
TCGATTTCAC CCCGTGGATT AGTGAATTTG ACATGAACGA
TAACAAGGAA AACTTCTGGC CGCTGATCGA ACATTATCAC
GAAGTTATTT CCGAAGCGCT GCGTAACAAA AAGCATCTGC
ACGGCCTGGG TTTCAACATC CAGGGTTTCG TTCAAAAGTA
CGTCAACATC GACAAAGTCA TGTGTGATCG CGCCATTGGC
AAACGTCGTG GCGGCACCCT GCTGTCCAAC GTTGGTCTGT
TTAATCAGCT GGAAGAACCG GACGCAAAAT ATTCAATTTG
CGATCTGGCT TTTGGCCAGT TCCAAGGTTC GTGGCATCAG
GCATTCAGCC TGGGCGTCTG TTCTACGAAC GTGAAGGGTA
TGAATATTGT TGTCGCTTCT ACCAAAAATG TGGTTGGTAG
CCAAGAATCG CTGGAAGAAC TGTGTAGTAT CTATAAGGCA
CTGCTGCTGG GTCCGTAA
```

To test the ability of this pathway to convert high concentrations of substrates, 3 g $L^{-1}$ of each 2-keto acid was fed into the culture (FIG. 10c). The amount of acetate ester conversion as well as the remaining alcohol in the medium was measured after 24 h. By introducing 2-keto acids, 0.5-2 g $L^{-1}$ of each acetate ester was observed (FIG. 10c). This indicated that Atf1 was capable of converting the alcohols to esters efficiently if increased flux to the alcohols is provided. This also showed that the strain produced sufficient acetyl-CoA and, thus, overexpression of acetyl-CoA generating enzymes such as pyruvate dehydrogenase complex was not necessary for this level of productivity (~2 g $L^{-1}$ in 24 h). These experiments also defined the relative rates for different alcohols; branched chain alcohols underwent >80% conversion to the acetate ester, while 1-propanol and 2-phenylethanol only underwent ~50% conversion after 24 h (FIG. 10c).

Since straight chain alcohols of C4-C10 have been previously generated using reverse β-oxidation (Dellomonaco et al. Nature 476:355-9, 2011), the specificity of Atf1 toward these (C2-C10) was explored using a similar feeding experiment (FIG. 10d). Ethyl acetate formation was relatively low (330 mg $L^{-1}$). Atf1 is known to produce ethyl acetate, but to a lesser extent than Atf2 (Fujii et al., J. Ferment Bioeng, 81:538-542, 1996). Butyl acetate was formed at a higher rate than propyl acetate (1.7 g $L^{-1}$ vs 0.57 mg $L^{-1}$). For C6-C10 alcohols, it was only possible to add 500-750 mg $L^{-1}$ into the culture due to solubility and toxicity. The *E. coli* strain was not able to grow in the presence of 500 mg $L^{-1}$ hexanol and very little hexyl acetate was produced. Octyl acetate formation was also low (140 mg $L^{-1}$). On the other hand, ~600 mg $L^{-1}$ decyl acetate was formed (>80% conversion) and the culture was able to grow normally. Thus, it appeared that Atf1 was capable of forming acetate esters from a broad range of substrates, and the strain was able to provide ample amounts of acetyl-CoA for the acetate ester formation. These data demonstrate pathways for acetate ester formation from a variety of substrates.

Example 4: Optimization of Isobutyl Acetate Production from Glucose

Figure 11:
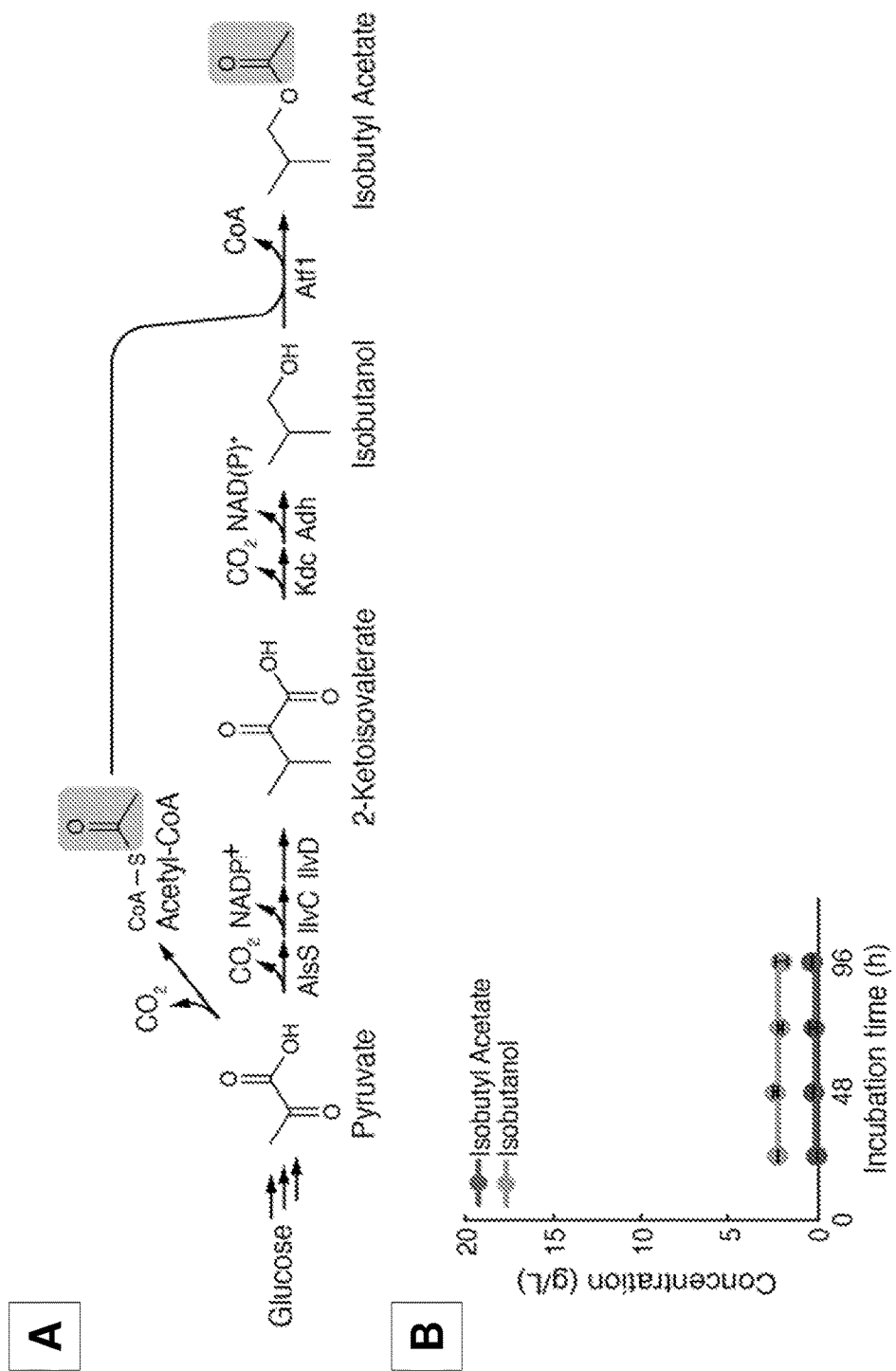
FIG. 11A shows a diagram of isobutyl acetate synthesis from glucose in bacteria.
FIG. 11B shows isobutyl acetate and isobutanol concentrations in culture layer during microbial production with a hexadecane layer. Cells were grown in 20 mL media in 250 mL screw-cap flasks at 37° C. until $OD_{600}$~0.4, then 1 mM IPTG was added. Hexadecane (20 mL) was added 1 h after induction. Production was performed at 30° C. in a rotary shaker at 250 rpm. Errors are SD (n=3).

As the previous Example demonstrates high flux acetate ester conversion from 2-keto acids by expressing kdc and ATF1 in JCL260, efficient acetate ester production from a single renewable carbon source was next explored. Since isobutanol production was demonstrated to approach maximal theoretical yields (Bastien et al., Metab Eng, 13:345-352, 2011) with titers up to 50 g $L^{-1}$ (Baez et al., Appl Microbiol Biotechnol, 90:1681-90, 2011), the performance of isobutyl acetate production from glucose was evaluated (FIG. 11a).

Figure 12:
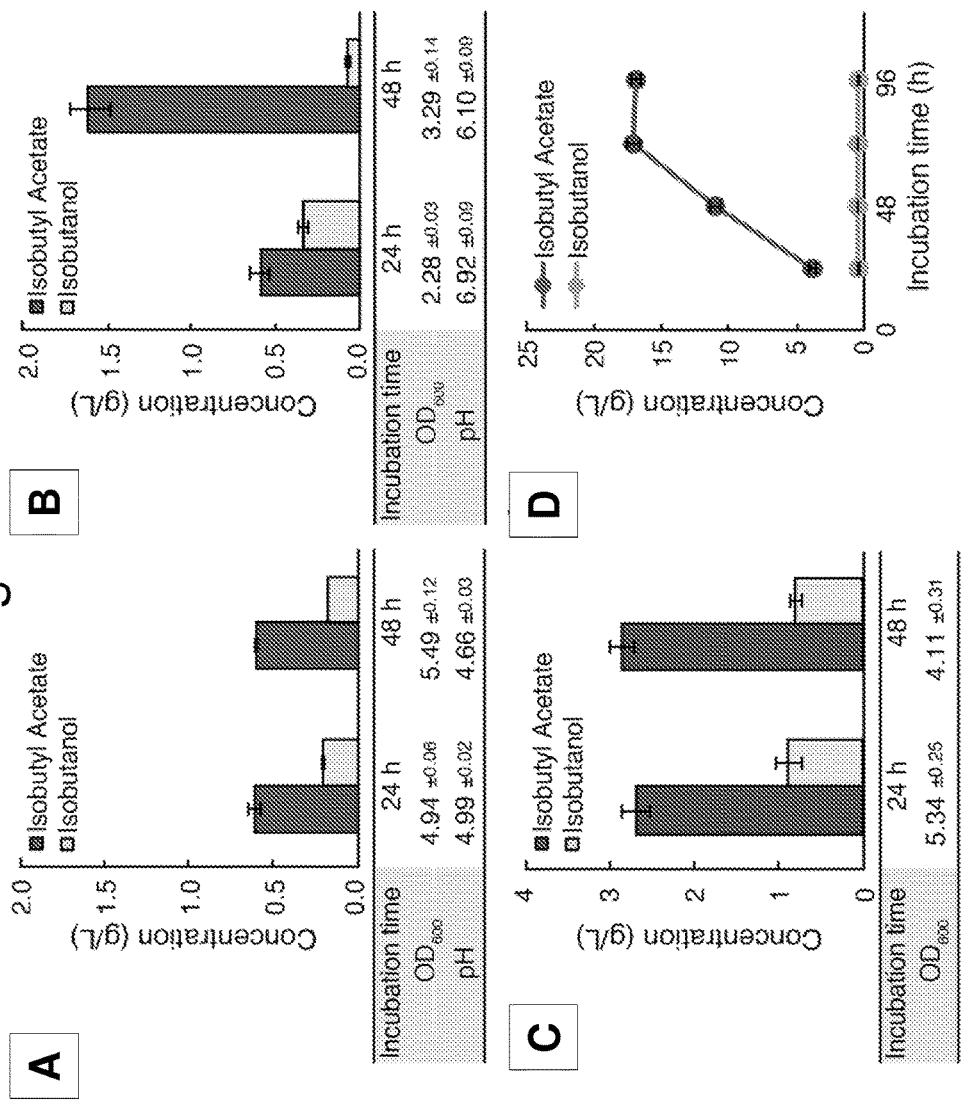
FIG. 12A provides a graph of production of isobutyl acetate in JCL88 with introduced isobutanol pathway.
FIG. 12B provides a graph of production of isobutyl acetate in JCL260 with introduced isobutanol pathway.
FIG. 12C provides a graph of production of isobutyl acetate in strain with the isobutanol pathway on a high-copy plasmid and ATF1 on a medium-copy plasmid.
FIG. 12D provides a graph of production of isobutyl acetate from glucose in strain with the isobutanol pathway on a high-copy plasmid and ATF1 on a medium-copy plasmid. In all panels, concentrations of isobutyl acetate and isobutanol are as labeled, and all strains were induced at $OD_{600}$~0.4 with 1 mM IPTG. Error bars are SD (n=3).

The high productivity of isobutanol production created concerns that acetyl-CoA availability might be limiting for isobutyl acetate production. Thus, two different *E. coli* strains were tested as production hosts for their ability to produce isobutyl acetate: JCL260 and JCL88. The difference between the two strains is that JCL88 contains pyruvate formate lyase encoded by pflB, which may provide increased availability of acetyl-CoA. The isobutanol pathway (AlsS of *B. subtilis*, IlvCD of *E. coli*, Kdc of *L. lactis*) and Atf1 (*S. cerevisiae*) was introduced into JCL88 and JCL260. The previously-used Adh step was excluded since it has been shown that endogenous Adhs efficiently carry out the reduction of isobutyraldehyde to isobutanol (Rodriguez and Atsumi Microb. Cell Fact. 11:90, 2012). In M9P supplemented with MOPS buffer (to maintain pH 7), both strains produced 0.6 g L$^{-1}$ isobutyl acetate after 24 h (FIGS. 12a and 12b). However, at 48 h JCL260 produced 1.6 g L$^{-1}$ isobutyl acetate and converted nearly all isobutanol to the ester, while JCL88 did not produce any additional isobutyl acetate after 24 h. Compared to JCL88, JCL26) exhibited higher titer, higher ester to alcohol ratio, and better pH stability. Thus, JCL260 was used as a production host for further analyses.

Based on the high ester to alcohol ratio, isobutanol production may have been limiting. To test this, the entirety of the isobutanol pathway (including adhA from *L. lactis*) (Atsumi et al., Appl. Microbiol. Biotechnol. 85:651-7, 2010) was introduced onto a high copy plasmid (with a ColE1 origin of replication, ~40 copies per cell) while moving ATF1 to a medium copy plasmid (p15A, ~15 copies). In principle, this allows high-level expression of the isobutanol pathway, and also introduces adhA (*L. lactis*) to further increase flux to isobutanol.

Figure 13:
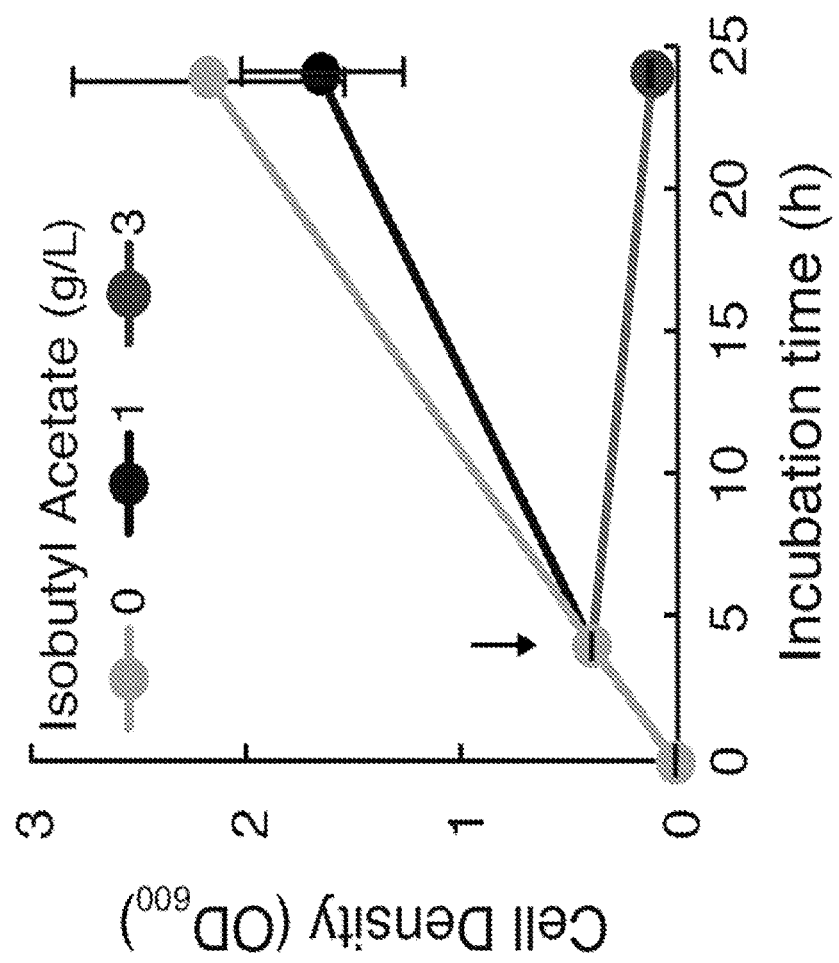
FIG. 13 shows the effect of isobutyl acetate on *E. coli* growth. JCL260 was grown at 30° C. in 5 mL M9P media containing 50 g $L^{-1}$ glucose in 15 mL screw-cap tubes. Black Arrow indicates the time point when isobutyl acetate: none (light gray), 1 g $L^{-1}$ (black), or 3 g $L^{-1}$ (dark gray) was added into culture. Error bars are SD (n=3).

This strain produced 4.5-fold more isobutyl acetate (2.7 g L$^{-1}$) in the first 24 h compared to JCL260 (FIG. 12b-c). This production represents 60% of the theoretical maximum yield (0.42 g isobutyl acetate/g glucose). However, from 24-48 h the strain only marginally increased the titer to 3.0 g L$^{-1}$, while the cell density dropped 20% (OD$_{600}$ 5.34 to 4.11; FIG. 12c). This suggested toxicity of isobutyl acetate. Indeed, toxicity experiments revealed that *E. coli* was unable to grow in the presence of 3 g L$^{-1}$ isobutyl acetate, undergoing cell lysis (FIG. 13).

To alleviate isobutyl acetate toxicity and further increase titer and yield, a hexadecane layer was incorporated into the production culture to achieve in situ product removal. This two-layer method has been successfully used to extract toxic products such as 3-methy-1-butanol from cultures (Connor et al. Appl. Microbiol. Biotechnol. 86:1155-64, 2010). Hexadecane was selected as it lacks hydrogen-bonding elements. This makes isobutanol and acetate less soluble in the hexadecane layer, and isobutyl acetate more soluble, facilitating its removal. Hexadecane is also non-toxic to *E. coli*, has low miscibility, and cannot be degraded by *E. coli*. Thus, production was repeated using added an equal volume of hexadecane added over the culture.

The utilization of a hexadecane layer enabled production of 3.9 g L$^{-1}$ isobutyl acetate in 24 h (FIG. 12d), an increase of 44% compared to the same strain without the use of a hexadecane layer (FIG. 12c). Furthermore, 97% of the isobutyl acetate was extracted into the hexadecane (FIG. 12d), indicating that the solvent was functioning to remove product from the culture. In contrast, isobutanol partitioning displayed the opposite behavior; 86% remained in the culture (FIG. 11b).

Production continued into 48 and 72 h, accumulating 11.3 g L$^{-1}$ and 17.5 g L$^{-1}$ 1 isobutyl acetate respectively. Production stopped after 72 h, with the titer remaining stable at 17.2 g L$^{-1}$ at 96 h. Final glucose consumption was measured at 96 h, resulting in an isobutyl acetate yield of 0.334 g/g glucose (17.2 g L$^{-1}$ isobutyl acetate produced/51.6 g L$^{-1}$ glucose consumed), which is 80% of the theoretical maximum from glucose (Table 4, below).

TABLE 4

Yield of Isobutyl Acetate from Glucose

| Isobutyl Acetate (g/L) | Glucose Consumed (g/L) | Yield (g Isobutyl Acetate/ g Glucose) | % of Max (0.42 g/g) | OD$_{600}$ at 96 h |
|---|---|---|---|---|
| 17.2 ± 0.4 | 51.6 ± 1.3 | 0.334 ± 0.016 | 79.6 ± 3.8 | 6.63 ± 0.22 |

Errors are SD (n = 3).

No degradation of isobutyl acetate by *E. coli* JCL260 was observed when incubated with isobutyl acetate for 24 h (Table 5). For these experiments, cells were grown in 5 mL M9P with 50 g L$^{-1}$ glucose in 15 mL screw-cap tubes at 37° C. until OD$_{600}$~0.4, then 1 mM IPTG was added and tubes were transferred to 30° C. Then, 1 h after induction, 1 g L$^{-1}$ isobutyl acetate was added. Remaining isobutyl acetate and formation of isobutanol was measured after 24 h by GC-FID analysis. Errors are SD (n=3).

TABLE 5

Lack of Isobutyl Acetate Degradation by Bacteria

| | Isobutyl acetate | Isobutanol |
|---|---|---|
| No cell | 99.9 ± 0.031% | 0.12 ± 0.031% |
| JCL260 | 99.9 ± 0.023% | 0.14 ± 0.027% |
| Strain 4 | 99.8 ± 0.023% | 0.22 ± 0.023% |

These results demonstrate high efficiency production of isobutyl acetate from glucose. Further, these data may suggest that production of other esters using efficient pathways (e.g., I-butanol) will also give high titers and yields of esters such as butyl acetate or butyl butyrate using this high efficiency production platform.

Example 5: Production of Tetradecyl Acetate from Glucose

The previous Examples describe platforms for microbial production of acetate esters. To demonstrate that these methods are applicable to a wide range of acetate ester products, a system for production of long chain (>C10) alkyl acetate esters was designed.

Figure 14:
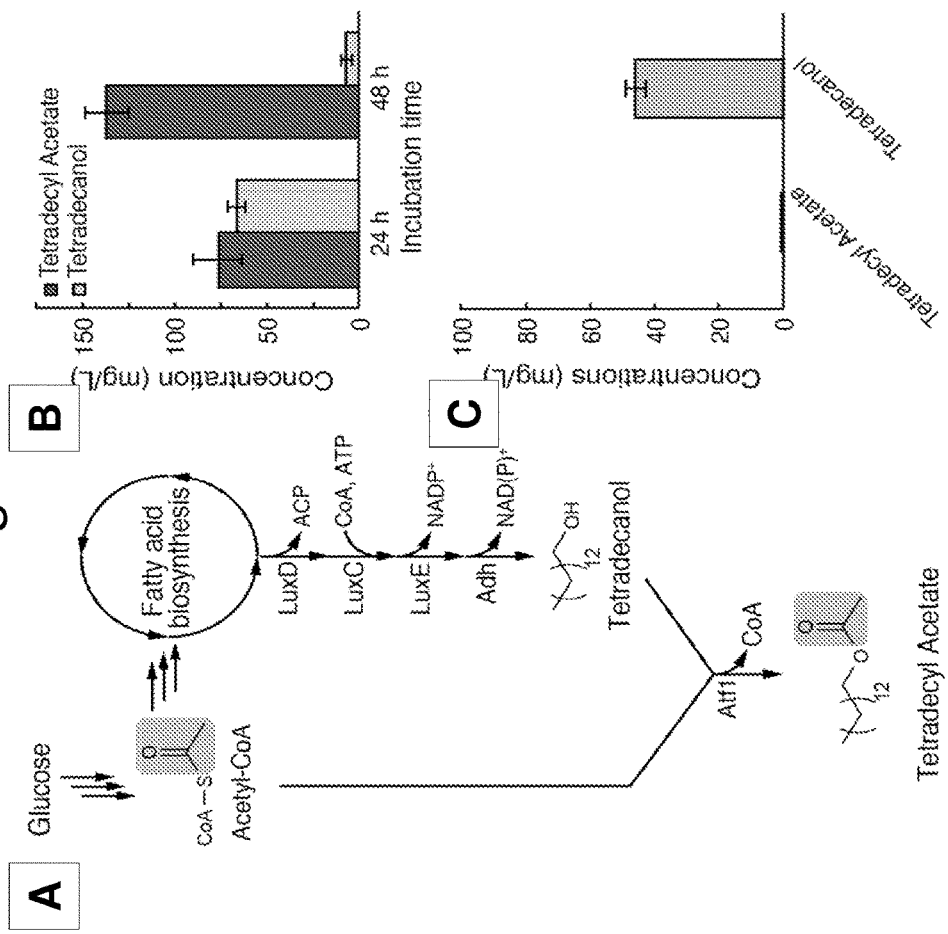
FIG. 14A shows a diagram of tetradecyl acetate synthesis from glucose in bacteria. LuxCDE complex produces tetradecyl aldehyde from tetradecyl-ACP in the fatty acid biosynthesis cycle. *E. coli* Adh converts the tetradecyl aldehyde to tetradecanol.
FIG. 14B provides a graph of production of tetradecyl acetate from glucose in AL1050 with LuxCDE enzyme system from *V. harveyi* along with Atf1.
FIG. 14C provides a graph of production of tetradecyl acetate from glucose in AL1050 with LuxCDE enzyme system from *V. harveyi* in the absence of Atf1. All strains were induced at $OD_{600}$~0.4 with 1 mM IPTG. Error bars are SD (n=3).

In brief, the LuxCDE enzyme system from *V. harveyi* (Belas et al. Science 218:791-3, 1982; Meighen, FASEB J. 7:1016-22, 1993) along with Atf1 was introduced into *E. coli* strain AL1050 (FIG. 14a). The LuxCDE system is known to produce tetradecyl aldehyde specifically, which is converted to tetradecyl alcohol by *E. coli* (Meighen, supra, 1993). Strain AL1050 produced 138 mg L$^{-1}$ tetradecyl acetate after 48 h with 95% tetradecyl alcohol converted to ester (FIG. 14b). With a strain lacking ATF1, only tetradecyl alcohol was produced (50 mg L$^{-1}$) (FIG. 14c).

These results demonstrate microbial production of tetradecyl acetate. Moreover, these data indicate that the acetate ester platforms described in Examples 1-4 are applicable to a wide variety of esters, particularly long chain alkyl acetate esters.

Example 6: Branched-Chain CoA Pathways for Higher Esters

With a full range of acetate esters produced from native pools of acetyl-CoA, production of more complex esters necessitates first producing higher (either longer chain or branched) chain CoA units (FIG. 9b). Production of longer straight chain CoA units has been achieved by extensive manipulation of E. coli metabolic pathways. For example, reverse β-oxidation was previously used to generate CoA units in lengths from butyryl-CoA up to decanoyl-CoA. To expand the functional repertoire of branched chain CoA-generating pathways, a pathway to generate branched chain CoA molecules from amino acid biosynthesis was developed.

Figure 15:
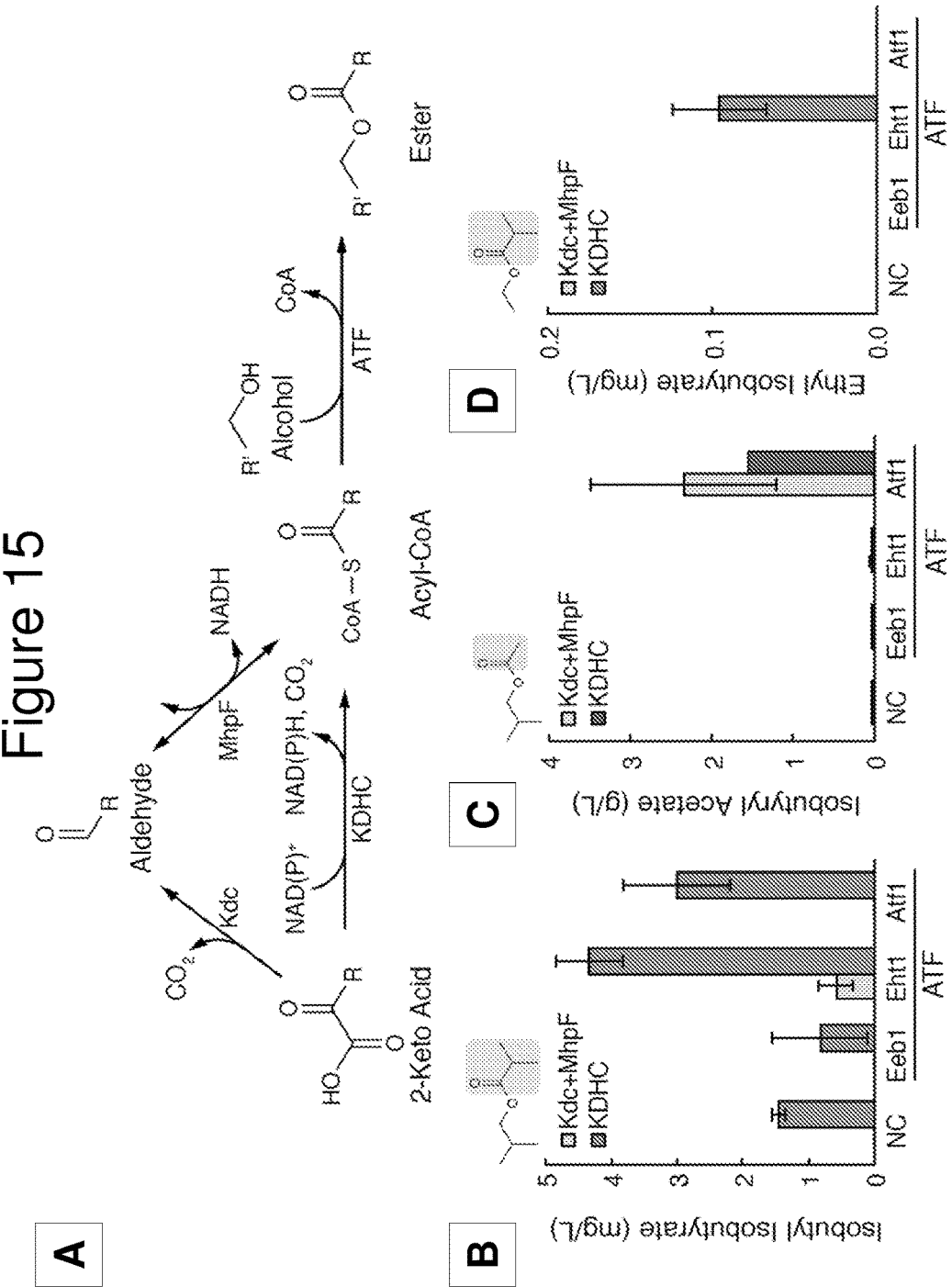
FIG. 15A illustrates the biosynthesis pathways for higher chain esters.
FIG. 15B provides a graphs showing production of isobutyl isobutyrate.
FIG. 15C provides a graph showing production of isobutyl acetate.
FIG. 15D provides a graph showing production of ethyl isobutyrate. Higher chain ester production was measured in cells using 2-keto acid via the Kdc-MhpF pathway or the KDHC pathway. Cells were grown in M9P media containing 10 g $L^{-1}$ glucose in 5 mL M9P media in 15 mL screw-cap tubes at 37° C. until $OD_{600}$~0.4. Then, 1 mM IPTG was added and cultures were transferred to 30° C. After 1 h of induction, 3 g $L^{-1}$ 2-ketoisovalerate and 3 g $L^{-1}$ of isobutanol were added. Error bars are SD (n=3).

Since Kdc already can generate various aldehydes, these aldehydes can be converted to acyl-CoAs by an acylating aldehyde dehydrogenase such as MhpF (E. coli), which converts acetaldehyde to acetyl-CoA and generates NADH (Ferrandez et al. J. Bacteriol. 179:2573-81, 1997; Lee et al. Biochem. Biophys. Res. Commun. 346:1009-15, 2006). It can also act on butanal with lower activity. Thus, with Kdc and MhpF, a 2-keto acid can potentially be converted to the corresponding acyl-CoA (FIG. 15a).

Alternatively, in many organisms, branched-chain CoAs such as isobutyryl-CoA, isovaleryl-CoA, and 3-methylvaleryl-CoA are intermediates in the degradation of L-valine, L-leucine, and L-isoleucine, respectively (Mooney et al. Annu. Rev. Plant Biol. 53:357-75, 2002). These products are formed by the branched-chain keto acid dehydrogenase complex (KDHC) (FIG. 15a), which is analogous to the pyruvate dehydrogenase complex (encoded by aceEF-lpd).

Figure 16:
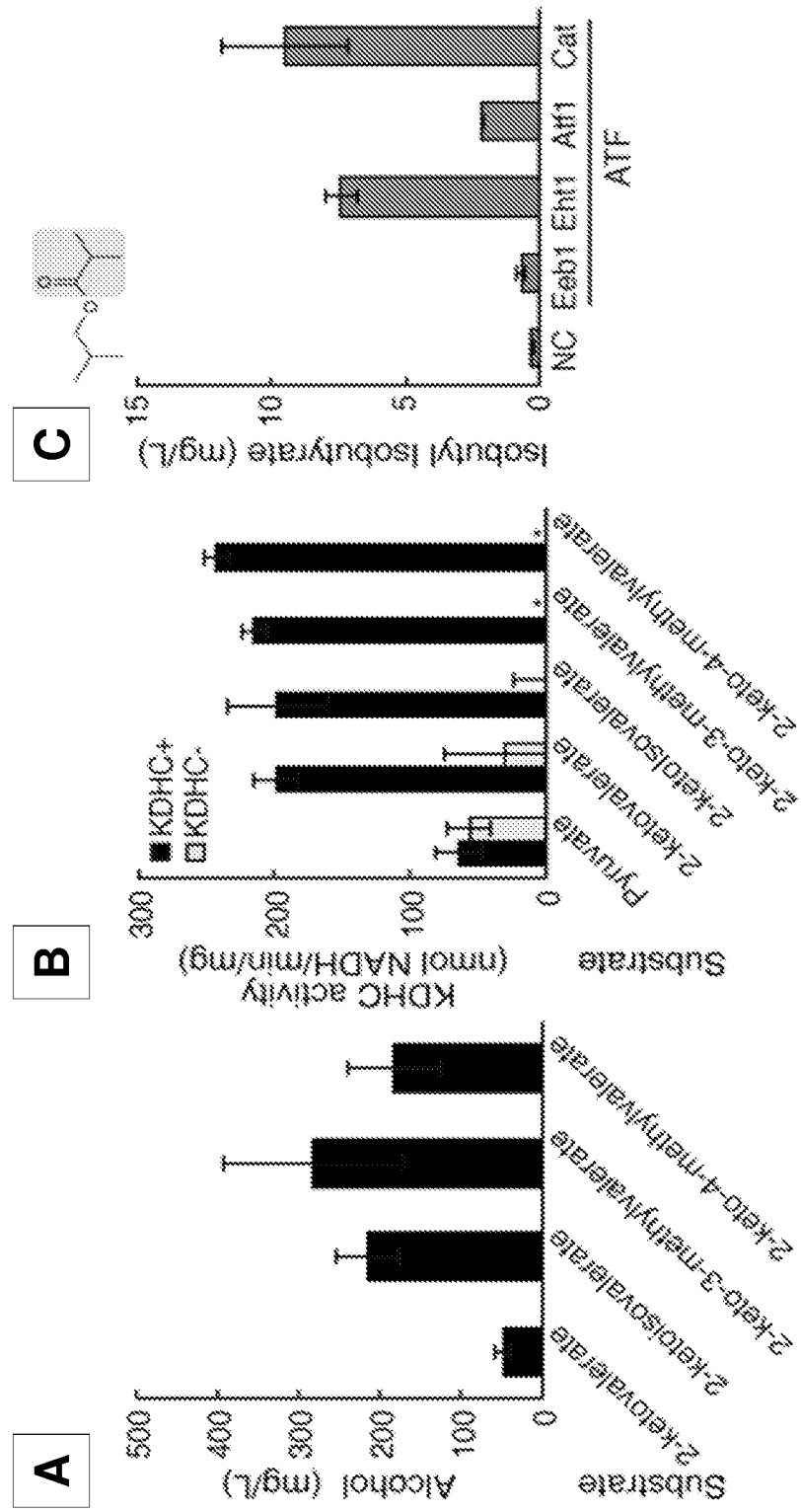
FIG. 16A provides a graph showing KDHC activity for 2-keto acids in vivo, while FIG. 16B provides a graph showing KDHC activity for 2-keto acids in vitro.
FIG. 16C provides a graph showing the production of isobutyl isobutyrate by strains expressing Eeb1, Eht1, or Cat, grown in M9P media containing 3 g $L^{-1}$ 2-ketoisovalerate and 3 g $L^{-1}$ isobutanol for 24 h, as compared to negative control. All strains were induced at $OD_{600}$~0.4 with 1 mM IPTG. Error bars are SD (n=3).

The full KDHC operon of P. putida (Hester et al. Method. Enzymol. 324:129-38, 2000; Alonso-Gutierrez et al. Metab. Eng. 19:33-41, 2013) was introduced into AL704 (JCL260 with ΔyqhD ΔadhP ΔeutG ΔyiaY ΔyjgB ΔfucO) (Rodriguez and Atsumi, Microb. Cell Fact. 11:90, 2012), which exhibits low endogenous aldehyde reductase/alcohol dehydrogenase activity. The KDHC operon is also referred to herein as KIVDH. By feeding 3 g L$^{-1}$ of various 2-keto acids into the culture, the resulting products were observed and compared to a strain without KDHC. The strain bearing the full KDHC operon generated 150-300 mg L$^{-1}$ isobutanol, 2-methyl-1-butanol, and 3-methyl-1-butanol while only ~75 mgL$^{-1}$ of 1-butanol was produced (FIG. 16a). No alcohols were detected from the control strain. This suggested that the KDHC complex from P. putida was active in E. coli. This experiment also revealed that these branched chain CoA products were being converted to aldehydes and alcohols by an unknown enzyme(s) since adhE was removed from AL704.

To confirm the activity of KDHC, cell lysates from each strain were prepared and activity was tested in vitro with pyruvate, 2-ketovalerate, 2-ketoisovalerate, 3-methylketovalerate, or 4-methylketovalerate as substrate. Activity was measured by detecting the reduction of NAD$^+$ in the presence of CoA. Activity of KDHC with each of the 2-keto acid substrates was similar (~225 nmol NADH/min/mg protein) except for pyruvate (67 nmol NADH/min/mg protein) (FIG. 16b). The negative control strain showed nearly identical activity for pyruvate as the other strains, indicating that activity towards pyruvate was coming from the endogenous pyruvate dehydrogenase complex. A small amount of activity (30 nmol NADH/min/mg protein) with 2-ketovalerate was observed from the negative control, perhaps due to slight promiscuity of the pyruvate dehydrogenase complex (FIG. 16b).

These results demonstrate the successful production of branched-chain CoA compounds using amino acid biosynthesis pathways.

Example 7: ATF Enzymes for Isobutyrate Ester Biosynthesis

Having established a method for production of branched-chain CoAs in Example 6, this method was tested for production of isobutyrate esters. As described above in Example 2, three ATFs (Eeb1, Eht1, and Atf1) were selected for their ability to produce isobutyl isobutyrate from isobutyryl-CoA and isobutanol in E. coli. 3 g L$^{-1}$ 2-ketoisovalerate and 3 g L$^{-1}$ isobutanol was fed into the cultures of the strains expressing KDHC and either EEB1, EHT1, ATF1, or mrfp (negative control). Whether Kdc-MhpF could replace KDHC for production of isobutyryl-CoA was also tested by measuring isobutyl isobutyrate production from strains expressing Kdc-MhpF and one of the same ATFs.

Of the strains harboring Kdc-MhpF, only the strain with Eht1 showed production (~0.5 mg L$^{-1}$) of isobutyl isobutyrate (FIG. 15b). In contrast, all strains expressing the KDHC pathway formed 2-5 mg L$^{-1}$ isobutyl isobutyrate (FIG. 15b), including the negative control. The strains with EHT1 and ATF1 showed the highest production of isobutyl isobutyrate. However, The Atf1 strain also produced >1 g L$^{-1}$ isobutyl acetate, indicating a high preference of Atf1 for acetyl-CoA (FIG. 15c). The Eht1 strain produced only a few mg L$^{-1}$ of isobutyl acetate, suggesting low activity of Eht1 toward acetyl-CoA (FIG. 15c).

The isobutyl isobutyrate formation was unexpectedly detected with the negative control (FIG. 15b). Coincidentally, the plasmids carrying the ATFs and mrfp genes contained the chloramphenicol resistance gene (cat) encoding chloramphenicol acetyltransferase, which is the same class of enzyme as the ATFs, and was also recently shown to have activity toward some aromatic alcohols (Alonso-Gutierrez et al. Metab. Eng. 19:33-41, 2013). To determine whether Cat was involved in isobutyl isobutyrate formation, cat was replaced with a kanamycin resistance (kan$^R$) gene. cat was also placed under the P$_L$lacO$_1$ promoter to investigate the formation of ester from a strain with increased cat expression.

As expected, the new negative control strain did not produce isobutyl isobutyrate, while the strain with cat under control of P$_L$lacO$_1$ showed the highest isobutyl isobutyrate formation (9.5 mg L$^{-1}$) (FIG. 15c). The Eht1 strain produced 7.4 mg L$^{-1}$ isobutyl isobutyrate in this condition. Cat showed highest isobutyl isobutyrate formation among the ATFs tested.

Figure 17:
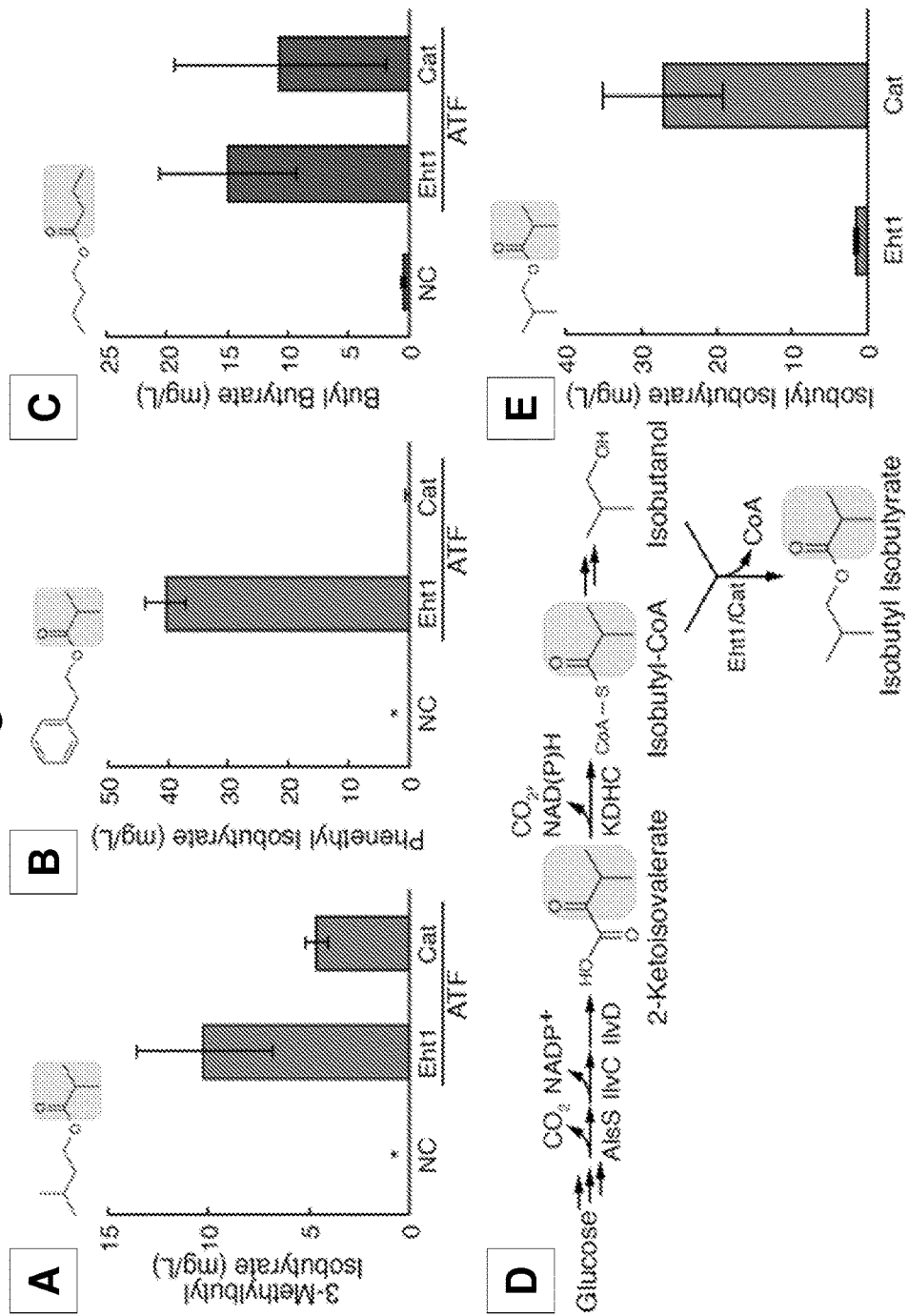
FIG. 17A-C shows production of higher chain esters in bacterial strains expressing Eht1 or Cat grown in M9P media containing various substrates: 3 g $L^{-1}$ 2-ketoisovalerate and 3 g $L^{-1}$ 3-methyl-1-butanol (FIG. 17A); 3 g $L^{-1}$ 2-phenylethanol (FIG. 17B); or 3 g $L^{-1}$ 2-ketovalerate and 3 g $L^{-1}$ 1-butanol (FIG. 17C) for 24 h. NC denotes a negative control strain.
FIG. 17D shows a diagram of the production of isobutyl isobutyrate from glucose, by expression of alsS, ilvCD, KDHC, and ATF (EHT1 or cat) in same cell.
FIG. 17E provides a graph showing the production of isobutyl isobutyrate by strains expressing Eht1 or Cat, when grown in M9P media containing 10 g $L^{-1}$ glucose for 24 h. All strains were induced at $OD_{600}$~0.4 with 1 mM IPTG. Error bars are SD (n=3).

To test the alcohol substrate specificity of Cat and Eht1 with respect to isobutyl-CoA as a co-substrate, 2-ketoisovalerate and either 3-methyl-1-butanol or 2-phenethanol was added to cultures and measured the isobutyrate esters produced. Although Cat was the best ATF for isobutyrate ester production with isobutanol (FIG. 15c), Eht1 was the best ATF for isobutyrate ester production with the larger substrates 3-methyl-1-butanol and 2-phenethanol (FIG. 17a-b). Only a small amount of ethyl isobutyrate was detected from Strain 16, which contains Eht1 (0.1 mg L$^{-1}$) (FIG. 15d). Cat only produced low levels of (4.6 mg L$^{-1}$) 3-methylbutyl isobutyrate, and did not produce any detectable 2-phenylethyl isobutyrate from the larger co-substrate isobutyryl-CoA. In contrast, 3-methyl-1-butanol and 2-phenylethanol were good substrates for Eht1, allowing production of 10 mg L$^{-1}$ 3-methylbutyl isobutyrate and 40 mg L$^{-1}$ 2-phenethyl isobutyrate, respectively (FIG. 17a-b).

Figure 18:
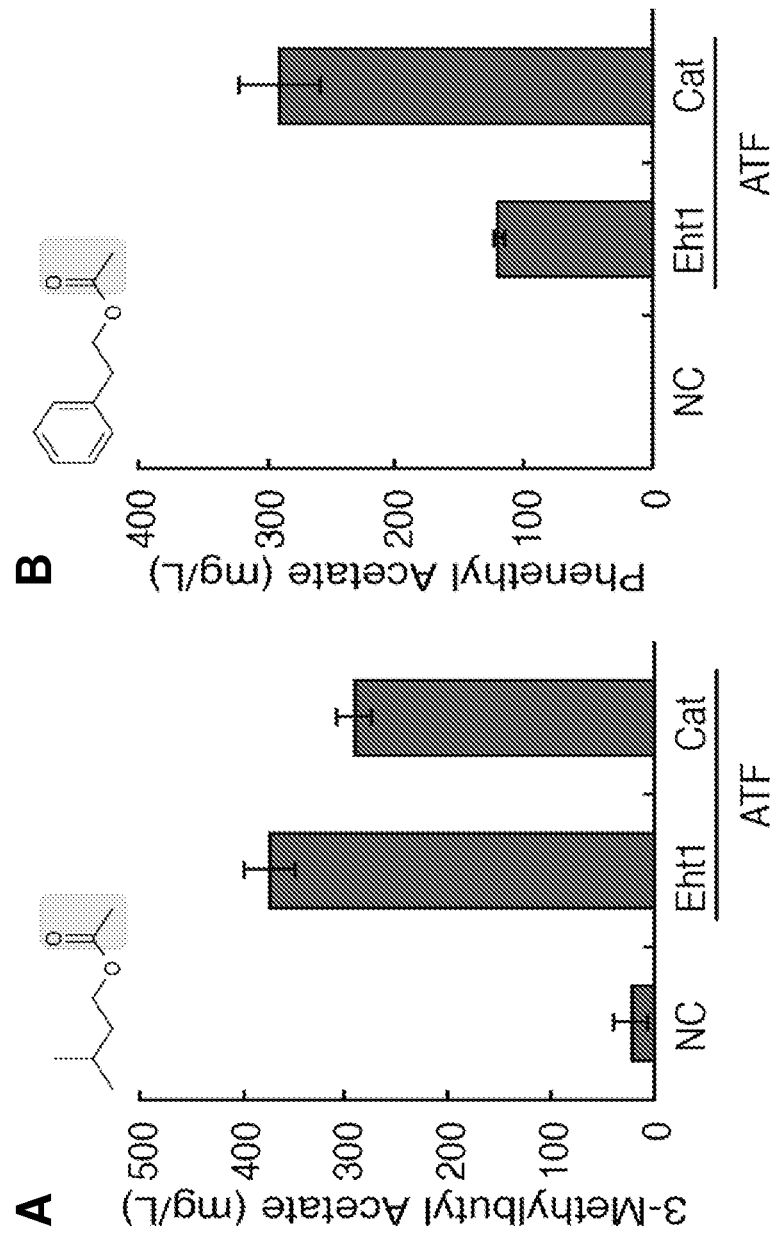
FIG. 18A-B shows the functions of Eht1 and Cat as acetyl-CoA transferases. Cells were grown in 5 mL M9P media containing 10 g $L^{-1}$ glucose in 15 mL screw-cap tubes at 37° C. until $OD_{600}$~0.4. Then, 1 mM IPTG was added. After 1 h of induction, 3 g $L^{-1}$ 2-ketoisovalerate and 3 g $L^{-1}$ 3-methyl-1-butanol (FIG. 18A) or 3 g $L^{-1}$ 2-phenylethanol (FIG. 18B) were added, and ester production was allowed to progress at 30° C. for 24 h at 250 rpm in a rotary shaker. Error bars are SD (n=3).

Cat and Eht1 both preferred acetyl-CoA over isobutyryl-CoA as a co-substrate, producing 100-400 mg L$^{-1}$ 3-methyl-1-butyl acetate (FIG. 18a) and 2-phenylethyl acetate (FIG. 18b). Although Eht1 is known as ethanol hexanoyl transferase (Saerens et al. J. Biol. Chem. 281-4446-56, 2006), according to the present results, Eht1 preferred larger alcohols as substrates. These varying titers (5 mg L$^{-1}$ to 40 mg L$^{-1}$) suggested that the activity of these ATFs with large substrates was limiting, rather than the supply of isobutyryl- CoA from KDHC. An ATF with higher activity toward C4-C6 CoAs could significantly improve the titers of these pathways.

Butyl butyrate is valuable as a solvent and flavoring, and has been successfully produced from engineered *Clostridium acetobutylicum* (Van den Berg, et al. Biotechnol. Bioeng. 110:137-42, 2013). Since the KDHC as described above was able to accept 2-ketovalerate as a substrate, it suggests an alternative means to effectively generate butyryl-CoA besides reverse β-oxidation. This would allow application of the biochemical strategy described herein to produce butyl butyrate, using KDHC as a source of the required straight chain CoA, butyryl-CoA. Thus, 3 g $L^{-1}$ each of 1-butanol and 2-ketovalerate was fed into cultures of *E. coli* expressing KDHC and either EHT1 or cat. After 24 h, the strains with EHT1 or cat produced 14.9 mg $L^{-1}$ and 10.6 mg $L^{-1}$ butyl butyrate, respectively (FIG. 17c). Butyl butyrate was not detected from strains without an ATF. These results demonstrate the microbial production of butyl butyrate.

Example 8: Isobutyl Isobutyrate Production from Glucose

The previously described Examples illustrate strains capable of isobutyrate ester production from added alcohols and keto acids. Thus, the next step is to simplify the system by constructing a strain able to generate complex esters using only simple sugars. Since the isobutanol pathway is capable of generating high flux to 2-ketoisovalerate, it is ideal for generating branched chain-CoA in the form of isobutyryl-CoA This, in turn, would allow a biological route to produce the symmetric ester isobutyl isobutyrate (FIG. 17d). Isobutyl isobutyrate has a water solubility of just 520 mg $L^{-1}$. This would allow for bilayer formation at high titers, which would simplify product removal during or after production, and limit the potential toxicity of the ester to *E. coli*.

The first half of the isobutanol pathway (AlsS, IlvCD) was introduced on a medium copy plasmid, with the expected rate limiting steps (KDHC and either Cat or Eht1) on a high copy plasmid. The above characterization of KDHC indicated that isobutyryl-CoA was endogenously converted to isobutyraldehyde and isobutanol (FIG. 16a). Thus, an AdhE-type enzyme, which would convert isobutyryl-CoA to isobutyraldehyde and then isobutanol, was excluded from the pathway.

Production was carried out using 5 mL cultures in screw-cap tubes. After 24 h, the strain bearing Cat produced 27 mg $L^{-1}$ isobutyl isobutyrate, much higher than the strain bearing Eht1, which only produced 1.4 mg $L^{-1}$ (FIG. 17e). A significant amount of isobutanol remained in the supernatant, suggesting that the ATFs characterized in this work, while functional, had weak activity towards branched-chain CoAs. There was no degradation of isobutyl isobutyrate by *E. coli* after 24 h (Table 6). This strategy provides tools for production of a range of larger esters from simple substrates using whole-cell catalysts.

TABLE 6

Lack of Isobutyl Isobutyrate Degradation

|  | Isobutyl isobutyrate | Isobutanol |
|---|---|---|
| No cell | 99.3 ± 0.22% | 0.7 ± 0.22% |
| AL704 | 98.8 ± 0.18% | 1.2 ± 0.18% |
| Strain 9 | 98.5 ± 0.48% | 1.5 ± 0.48% |
| Strain 16 | 97.5 ± 0.48% | 2.5 ± 0.48% |
| Strain 18 | 98.8 ± 0.40% | 1.2 ± 0.40% |

For the experiments in the above table, cells were grown in 5 mL M9P with 50 g $L^{-1}$ glucose in 15 mL screw-cap tubes at 37° C. until $OD_{600}$~0.4, then 1 mM IPTG was added and tubes were transferred to 30° C. One hour after induction, 1 g $L^{-1}$ isobutyl isobutyrate was added. Remaining isobutyl isobutyrate and formation of isobutanol was measured after 24 h by GC-FID analysis. Errors are SD (n=3). Strain 9=AL704 (JCL260 with ΔyqhD ΔadhP ΔeutG ΔyiaY ΔyjgB ΔfucO) with full KDHC operon of *P. putida*; Strain 16=Eht1 strain with kanamycin resistance ($kan^R$) gene; Strain 18=cat under the $P_LlacO_1$ promoter.

Example 9: Isobutyl Acetate Production from Glucose and Acetate

Figure 19:
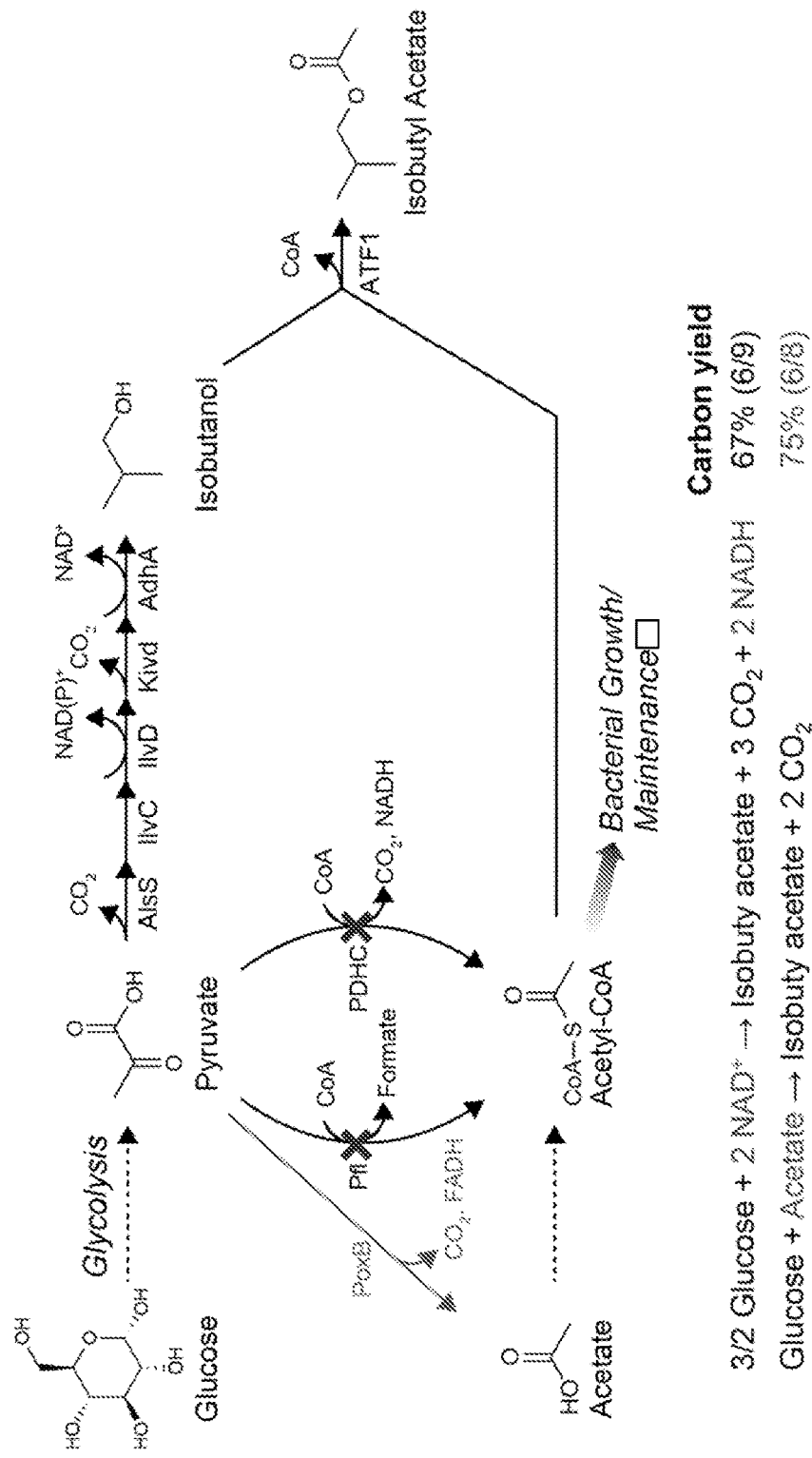
FIG. 19 shows a diagram of an isobutyl acetate production pathway using acetate and glucose.

As described above, isobutyl acetate (IBA) has been produced in an engineered *E. coli* to titers of 17.2 g/L with 80% of the theoretical maximum yield from glucose. In the cell, carbon is required to produce isobutanol and acetyl-CoA, and the joining (condensation) of these two molecules forms IBA. However, when using glucose as the sole carbon source to make IBA, 1.5 glucose molecules (9 carbons) are required to make the 6 carbon IBA molecule, and 3 carbons are released as $CO_2$. To increase the yield of IBA production and decrease the microbial metabolic burden, production of IBA from glucose and acetate is tested (FIG. 19).

In this strategy, the production of isobutanol and acetyl-CoA is metabolically separated to allow for optimal production of each substrate. All available pyruvate is funneled towards isobutanol by preventing pyruvate conversion into acetyl-CoA. Acetate is supplied externally to the cell and subsequently converted into acetyl-CoA by the acetate assimilating pathways. In this method, both glucose and acetate are supplied to *E. coli*, and an input of 8 carbons will make a 6 carbon product with only two carbons released in the form of $CO_2$. Through this pathway there is a greater theoretical yield for IBA production: 75% versus 67% when using only glucose. Through this process the feeding of the relatively inexpensive and abundant acetate will allow greater yield and potentially economically feasible IBA production.

First, the pyruvate dehydrogenase complex is deleted from *E. coli* in order to separate the glucose-to-isobutanol from the acetate-to-acetyl-CoA pathways. Carbon flow towards pyruvate and acetyl-CoA is separated in the cell by deleting the native pyruvate dehydrogenase complex (PDHC) genes via a well-established method (Baba et al. Mol. Syst. Biol. 2:2006-8, 2006). The PDHC is encoded by aceE, aceF, and lpd. Here aceEF is deleted from the production strain (Atsumi et al. Nature 451:86-9, 2008). This strain does not contain pflB, which codes for a pyruvate formate lyase that converts pyruvate to acetyl-CoA. Thus the resulting strain does not have any enzymes able to convert pyruvate to acetyl-CoA. For isobutanol production, pyruvate is converted into 2-acetolactate and subsequently isobutanol. Funneling pyruvate towards both 2-acetolactate and acetyl-CoA to make IBA is inefficient. Removal of the PDHC prevents loss of pyruvate towards acetyl-CoA and conserves the cell's available pyruvate for isobutanol production. Acetate is externally supplemented to allow the cell to make the necessary acetyl-CoA without using carbon supplied from glucose.

PDHC plays the important cellular role of producing acetyl-CoA, the first intermediate required for the TCA cycle. Wild-type *E. coli* can survive in the absence of the PDHC by relying on the native PflB to convert pyruvate to acetyl-CoA during anaerobic growth (Murarka et al. J. Biol. Chem. 285:31548-58, 2010; Peebo et al. Appl. Microbiol. Biotechnol. 98:5131-5143, 2014). *E. coli* does contain a pyruvate oxidase (PoxB) enzyme, which aids in pyruvate metabolism during anaerobic growth (Abdel-Hamid et al. Microbiology 147:1483-98, 2001), and provides another route to convert pyruvate to acetate and $CO_2$. However, poxB does not appear necessary during glucose fermentation (Murarka et al. J. Biol. Chem. 285:31548-58, 2010), and is therefore unlikely to play an appreciable role in pyruvate to acetyl-CoA conversion in the engineered *E. coli* strains.

With the deletion of aceEF and pflB from the host strain, the cell is not be able to produce acetyl-CoA from pyruvate, which is essential for its survival. Therefore *E. coli* is fed acetate so that it can convert it to acetyl-CoA (Lin et al. Appl. Microbiol. Biotechnol. 71:870-4, 2006).

*E. coli* has three known routes to convert acetate to acetyl-CoA. The first, Acs (EcoCyc #: EG11448), is an acetyl-CoA synthetase that converts acetate to acetyl-CoA in an ATP dependent manner. This reaction is irreversible and the most favored for acetate consumption and acetyl-CoA production (Lin et al. Appl. Microbiol. Biotechnol. 71:870-4, 2006). Alternatively, acetate is converted to acetyl phosphate by acetate kinase A (AckA, EcoCyc#: EG10027), which is subsequently converted to acetyl-CoA via phosphate acetyltransferase (Pta, EcoCyc#: EG20173). This reaction is reversible but has been identified to aid in acetate recycling into acetyl-CoA (Peebo et al. Appl. Microbiol. Biotechnol. 98:5131-5143, 2014). Lastly, acetate can be converted to acetaldehyde by AldB (EcoCyc#: EG12292) and then to acetyl-CoA by MhpF (EcoCyc#: M014).

Figure 20:
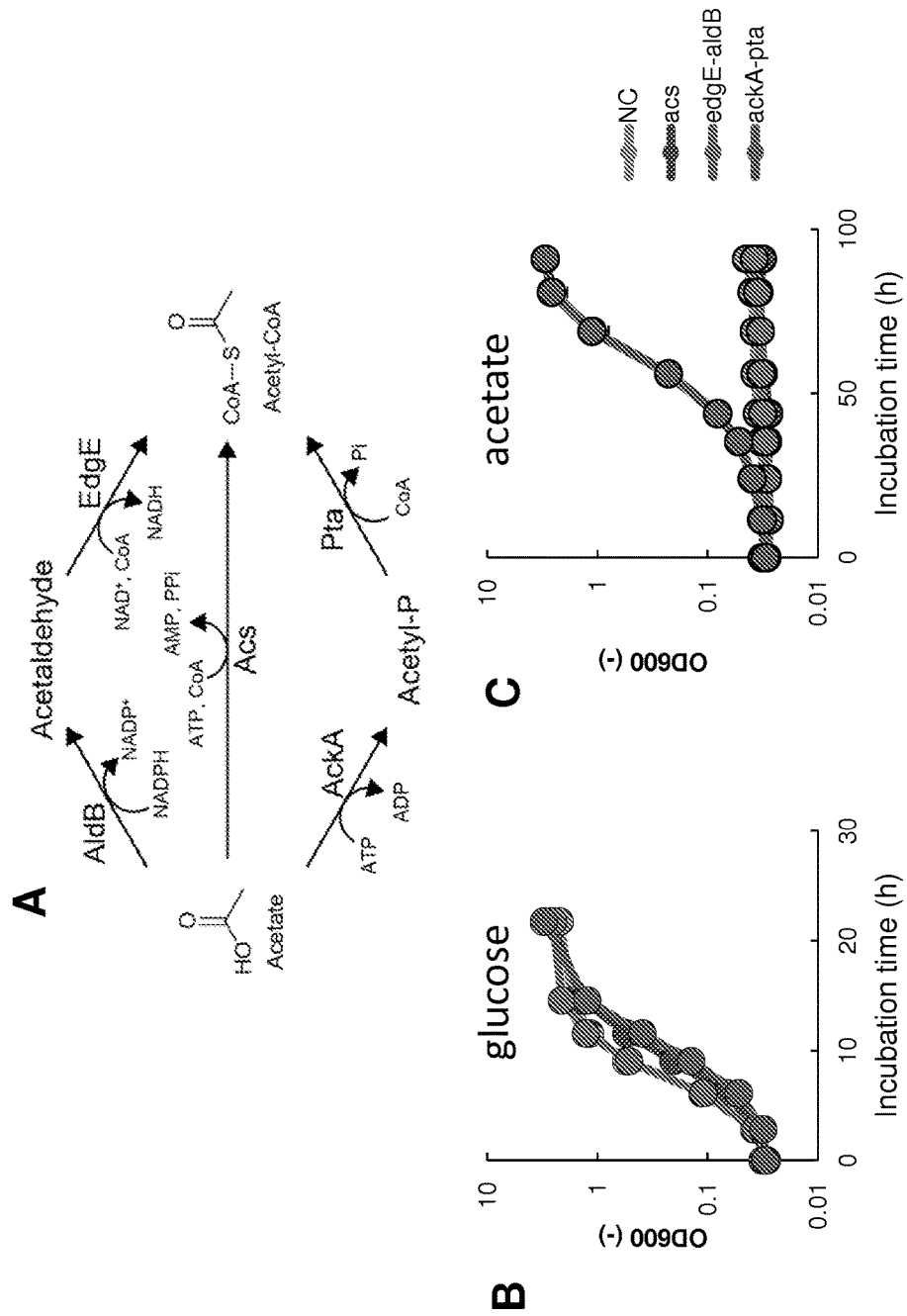

With three native routes to produce acetyl-CoA from acetate, the cell is thought to have sufficient acetyl-CoA for survival and for target chemical production (FIG. 20*a*). Each of these candidate pathways was overexpressed in *E. coli*, which were fed 10 g/L acetate. Acetate consumption was indicated by cell growth. The pathway of AckA-Pta yielded the best growth rate on acetate and glucose in JCL260 (FIG. 20*b-c*).

Figure 21:
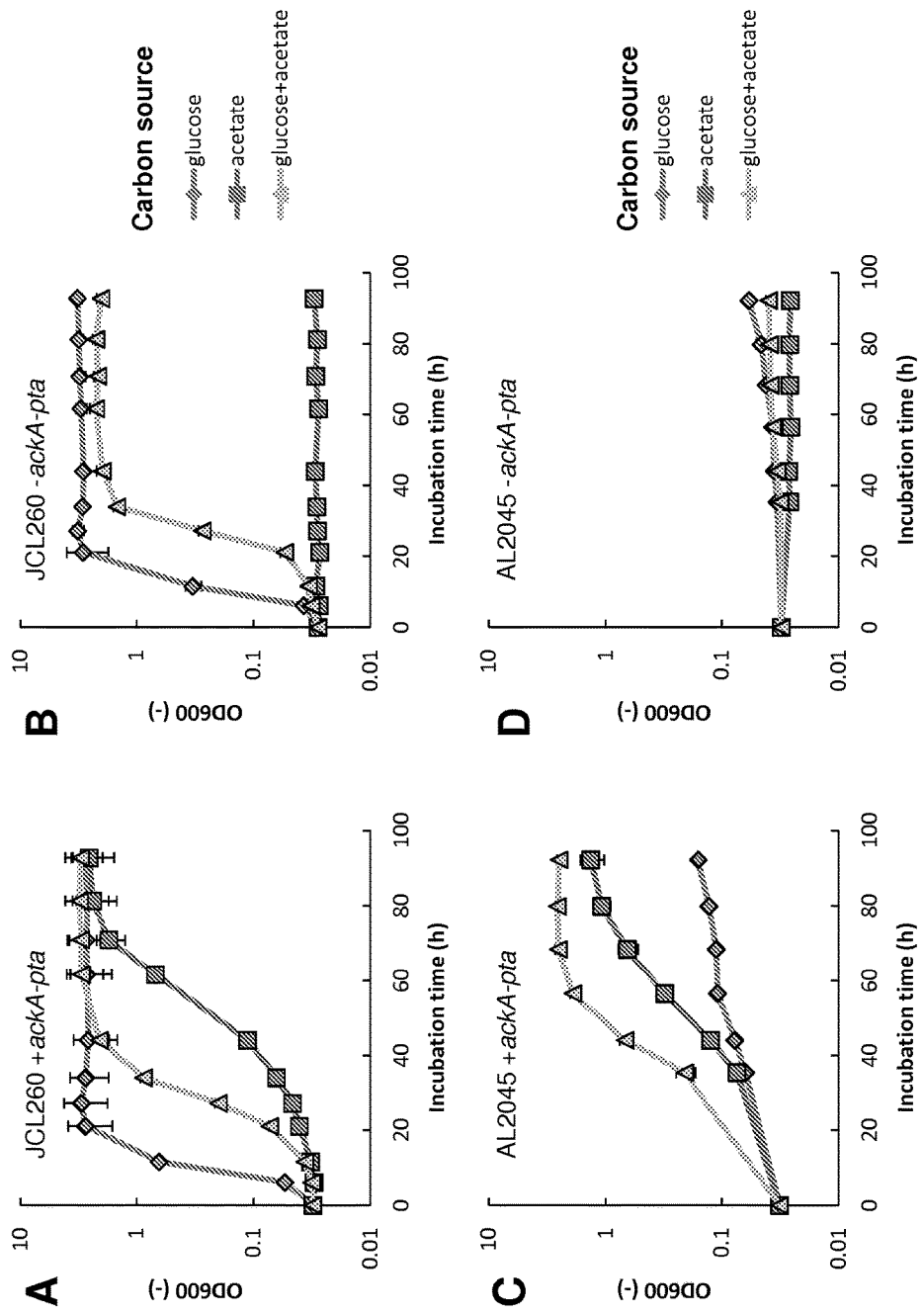
FIG. 21A-D shows the growth of recombinant bacteria in the presence (JCL260) or absence of aceEF (AL2045), and in the presence or absence of an acetate assimilating pathway (ackA-pta). Growth of strains in culture medium containing 10 g/L glucose, 10 g/L acetate, or 10 g/L glucose and 10 g/L acetate was compared. Cells were grown at 37° C. on a rotary shaker (250 rpm). Overnight cultures were grown in 3 mL Luria Broth containing appropriate antibiotics. The overnight cultures were inoculated 1% in 5 mL M9 minimal media (containing appropriate antibiotics and 1 mM IPTG) and labeled carbon source in 15-ml screw-cap tubes.

Next, the growth of JCL260 and AL2045, which contains ΔaceEF with and without the acetate assimilating pathway (ackA-pta), was compared (FIG. 21). AL2045 did not grow without the acetate assimilating pathway (FIG. 21*d*), but acetate enhanced the growth of AL2045 with the acetate assimilating pathway (FIG. 21*c*). Acetate inhibited the growth of JCL260 without the acetate assimilating pathway (FIG. 21*b*).

Figure 22:
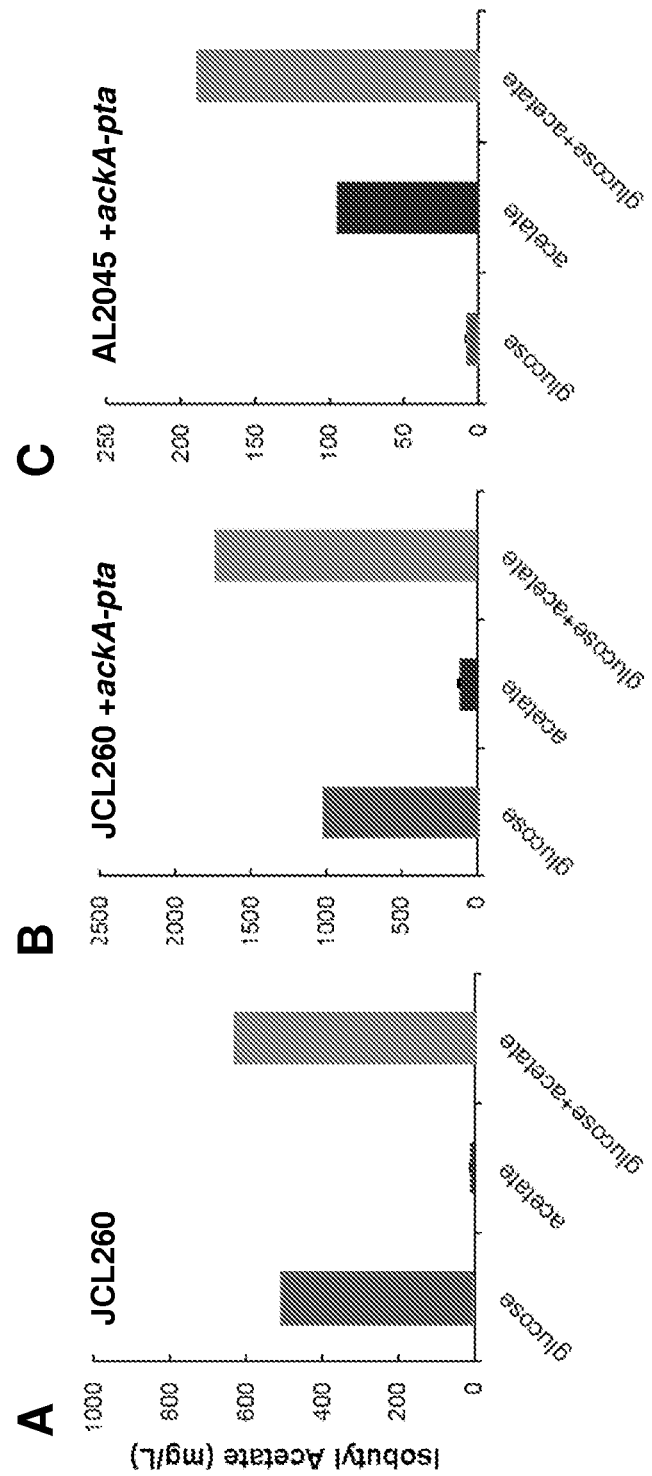
FIG. 22A-C shows isobutyl acetate production from glucose and acetate by recombinant bacteria in the presence or absence of an acetate assimilating pathway (ackA-pta), in the presence (JCL260) or absence of aceEF (AL2045). Overnight cultures were grown in 3 mL Luria Broth containing appropriate antibiotics. The overnight cultures were inoculated 1% in 3 mL M9 production media (containing 5 g/L yeast extract and appropriate antibiotics) with 10 g/L glucose, 10 g/L acetate, and 10 g/L glucose and 10 g/L acetate (as labeled) in 15-ml screw-cap tubes. Cells were grown to an $OD_{600}$ of 0.4 at 37° C., followed by adding 1 mM IPTG and 3 mL hexadecane. The cultures were allowed to produce at 30° C. on a rotary shaker (250 rpm) for 24 h.

IBA production was tested by incubation of these strains for 24 h in M9 production medium (containing 5 g/L yeast extract) with 10 g/L glucose, 10 g/L acetate or both 10 g/L glucose and 10 g/L acetate. Acetate improved IBA production in JCL260 with the acetate assimilating pathway in the presence of glucose (FIG. 22*b*), but acetate did not significantly improve IBA production in JCL260 without the acetate assimilating pathway (FIG. 22*a*). These results indicate that JCL260 with the acetate assimilating pathway was capable of producing IBA from glucose and acetate without the deletion of aceEF. AL2045 cannot produce IBA well with either glucose or acetate, but co-feeding of both glucose and acetate enhanced IBA production (FIG. 22*c*).

We claim:

1. An *Escherichia coli* bacterium comprising at least one recombinant polynucleotide encoding a plurality of enzymes, wherein the plurality of enzymes comprise an acetolactate synthase (ALS), an acetohydroxy acid isomer-oreductase (AHIR) and a dihydroxy acid dehydratase (DHAD), either a 2-keto acid decarboxylase (KDC) or a 2-ketoisovalerate dehydrogenase enzyme complex (KIVDH), an alcohol dehydrogenase (ADH), an alcohol transferase (ATF), an acetate kinase A (AckA), and a phosphate acetyltransferase (Pta), and wherein expression of the plurality of enzymes permits the bacterium to grow in culture medium comprising acetate and glucose, and results in an increase in production of an ester as compared to a corresponding bacterium lacking the at least one recombinant polynucleotide.

2. The bacterium of claim 1, wherein the recombinant polynucleotide comprises one, two or three recombinant polynucleotides.

3. The bacterium of claim 2, wherein the ATF is ATF1.

4. The bacterium of claim 3, wherein the ester comprises an acetate ester.

5. The bacterium of claim 4, wherein the acetate ester comprises one or more of ethyl acetate, isobutyl acetate, isoamyl acetate, propyl acetate, amyl acetate, and 2-pheneethyl acetate.

6. The bacterium of claim 2, wherein the ATF is EHT1.

7. The bacterium of claim 6, wherein the ester comprises an isobutyrate ester.

8. The bacterium of claim 7, wherein the isobutyrate ester comprises one or more of ethyl isobutyrate, isobutyl isobutyrate, 3-methylbutyl isobutyrate, and phenethyl isobutyrate.

9. The bacterium of claim 2, wherein the KDC is Kivd.

10. The bacterium of claim 2, wherein the KIVDH is Kivdh.

11. The bacterium of claim 2, wherein the ALS is AlsS encoded by alsS of *B. subtilis*, the AHIR is IlvC encoded by ilvC of *E. coli*, and the DHAD is IlvD encoded by ilvD of *E. coli*.

12. The bacterium of claim 2, wherein the bacterium further comprises a mutation in an endogenous alcohol dehydrogenase gene, wherein said mutation reduces alcohol dehydrogenase (ADH) activity of a product of said gene.

13. The bacterium of claim 12, wherein the alcohol dehydrogenase gene comprises adhE.

14. The bacterium of claim 2, wherein the bacterium further comprises a mutation in an endogenous isobutyraldehyde reductase gene, wherein said mutation reduces isobutyraldehyde reductase (IBR) activity of the product of said gene.

15. The bacterium of claim 14, wherein said isobutryaldehyde reductase gene comprises one or any combination of the group consisting of yqhD, adhP, eutG, yjgB, and fucO genes.

16. The bacterium of claim 12, wherein the mutation is a functional deletion of each of adhE, yqhD, adhP, eutG, yiaY, yjgB, betA, and fucO genes.

17. The bacterium of claim 12, wherein the bacterium further comprises a functional deletion in each of lnr, ldhA, frdBC, pflB, and pta endogenous genes, or a functional deletion in each of eutE, yahK, ybbO, gldA, dkgA/yqhE, and yghA genes.

18. The bacterium of claim 2, wherein the recombinant polynucleotides are stably integrated into the genome of the bacterium.

19. A method for producing an ester, the method comprising:
(a) providing the bacterium of claim 2; and
(b) culturing the bacterium of (a) in culture medium comprising a substrate under conditions suitable for the conversion of the substrate to an ester.

20. The method of claim 19, further comprising step (c) purifying the ester.

21. The method of claim 20, wherein the ester is purified by a technique selected from the group consisting of gas stripping, siphoning, and organic extraction.

22. The method of claim 21, wherein the ester comprises one or both of an acetate ester and an isobutyrate ester.

23. The method of claim 22, wherein the substrate comprises one or more of the group consisting of glucose, a 2-keto acid and a C2-C10 straight chain alcohol.

24. The method of claim 22, wherein the ester is an acetate ester comprising isobutyl acetate, and step (b) comprises use of hexadecane to remove the isobutyl acetate produced by the bacterium.

* * * * *